US010864031B2

(12) United States Patent
Mazor et al.

(10) Patent No.: US 10,864,031 B2
(45) Date of Patent: Dec. 15, 2020

(54) ABLATION METHOD FOR CREATING ELONGATE CONTINUOUS LESIONS ENCLOSING MULTIPLE VESSEL ENTRIES

(71) Applicant: ADAGIO MEDICAL, INC., Laguna Hills, CA (US)

(72) Inventors: Meital Mazor, Laguna Hills, CA (US); James L. Cox, Denver, CO (US); Alexei Babkin, Dana Point, CA (US); Steven W. Kovalcheck, San Diego, CA (US); Thomas Chien, Laguna Hills, CA (US); Nicolei King, Laguna Hills, CA (US)

(73) Assignee: Adagio Medical, Inc., Laguna Hills, CA (US)

( * ) Notice: Subject to any disclaimer, the term of this patent is extended or adjusted under 35 U.S.C. 154(b) by 785 days.

(21) Appl. No.: 15/362,670

(22) Filed: Nov. 28, 2016

(65) Prior Publication Data

US 2017/0151008 A1 Jun. 1, 2017

Related U.S. Application Data

(60) Provisional application No. 62/260,825, filed on Nov. 30, 2015.

(51) Int. Cl.
*A61B 18/02* (2006.01)
*A61B 18/00* (2006.01)
*A61M 25/01* (2006.01)

(52) U.S. Cl.
CPC .... *A61B 18/02* (2013.01); *A61B 2018/00023* (2013.01); *A61B 2018/00029* (2013.01);
(Continued)

(58) Field of Classification Search
CPC .......... A61B 18/02; A61B 2018/00023; A61B 2018/00029; A61B 2018/00041;
(Continued)

(56) References Cited

U.S. PATENT DOCUMENTS 3,062,017 A 11/1962 Balcar
3,613,689 A 10/1971 Crump
(Continued)

FOREIGN PATENT DOCUMENTS

GB 1422535 1/1976
GB 2283678 6/1996
(Continued)

OTHER PUBLICATIONS

Office Action dated Jul. 26, 2018 for U.S. Appl. No. 14/915,631.
(Continued)

*Primary Examiner* — Lee S Cohen
*Assistant Examiner* — Tigist S Demie
(74) *Attorney, Agent, or Firm* — Richard Batt

(57) ABSTRACT

A method of creating a lesion in cardiac tissue where the method includes deploying a distal treatment section of an ablation catheter into a heart chamber and manipulating the distal treatment section against the cardiac tissue and into a curved shape that encloses a plurality of vessel entries in the heart chamber. The method further includes commencing a first application of ablation energy from the distal treatment section to the cardiac tissue and halting the first application of ablation energy to the cardiac tissue. The first application of ablation energy causes formation of a first continuous lesion in the cardiac tissue that encloses the plurality of vessel entries.

22 Claims, 32 Drawing Sheets

(52) U.S. Cl.
CPC ........... *A61B 2018/00041* (2013.01); *A61B 2018/00285* (2013.01); *A61B 2018/00351* (2013.01); *A61B 2018/00357* (2013.01); *A61B 2018/00375* (2013.01); *A61B 2018/00577* (2013.01); *A61B 2018/00821* (2013.01); *A61B 2018/00839* (2013.01); *A61B 2018/00863* (2013.01); *A61B 2018/00904* (2013.01); *A61B 2018/0212* (2013.01); *A61B 2018/0268* (2013.01); *A61M 25/0147* (2013.01)

(58) Field of Classification Search
CPC .......... A61B 2018/00285; A61B 2018/00351; A61B 2018/00357; A61B 2018/00375; A61B 2018/00577; A61B 2018/00821; A61B 2018/00839; A61B 2018/00863; A61B 2018/00904; A61B 2018/0212; A61B 2018/0268; A61M 25/0147
See application file for complete search history.

(56) References Cited

U.S. PATENT DOCUMENTS

| | | | |
|---|---|---|---|
| 3,889,680 A | 6/1975 | Armao | |
| 3,942,010 A | 3/1976 | Peterson | |
| 3,993,123 A | 11/1976 | Chu | |
| 4,034,251 A | 7/1977 | Haas | |
| 4,167,771 A | 9/1979 | Simons | |
| 4,226,281 A | 10/1980 | Chu | |
| 4,281,268 A | 7/1981 | Sawa | |
| 4,384,360 A | 5/1983 | Kitadate | |
| 4,418,421 A | 11/1983 | Kitadate | |
| 4,519,389 A | 5/1985 | Gudkin | |
| 4,548,045 A | 10/1985 | Aitares | |
| 4,802,475 A | 2/1989 | Weshahy | |
| 4,838,041 A | 6/1989 | Bellows | |
| 4,843,446 A | 6/1989 | Nishino | |
| 4,945,562 A | 7/1990 | Staub | |
| 4,946,460 A | 8/1990 | Merry | |
| 4,982,080 A | 1/1991 | Wilson | |
| 5,012,505 A | 4/1991 | Zupancic | |
| 5,037,395 A | 8/1991 | Spencer | |
| 5,108,390 A | 4/1992 | Potocky | |
| 5,147,355 A | 9/1992 | Friedman | |
| 5,147,538 A | 9/1992 | Wright | |
| 5,155,093 A | 10/1992 | Den | |
| 5,173,606 A | 12/1992 | Weinberger | |
| 5,211,646 A | 5/1993 | Alperovich | |
| 5,212,626 A | 5/1993 | Bell | |
| 5,214,925 A | 6/1993 | Hoy | |
| 5,237,824 A | 8/1993 | Pawliszyn | |
| 5,254,116 A | 10/1993 | Baust | |
| 5,274,237 A | 12/1993 | Gallagher | |
| RE34,502 E | 1/1994 | Webster | |
| 5,275,595 A | 1/1994 | Dobak, III | |
| 5,324,286 A | 6/1994 | Fowler | |
| 5,334,181 A | 8/1994 | Rubinsky | |
| 5,369,384 A | 11/1994 | Woods | |
| 5,400,602 A | 3/1995 | Chang | |
| 5,405,533 A | 4/1995 | Hazleback | |
| 5,417,072 A | 5/1995 | Silver | |
| 5,433,717 A | 7/1995 | Rubinsky | |
| 5,452,582 A | 9/1995 | Longsworth | |
| 5,471,844 A | 12/1995 | Levi | |
| 5,494,039 A | 2/1996 | Onki | |
| 5,504,924 A | 4/1996 | Ohashi | |
| 5,520,682 A | 5/1996 | Baust | |
| 5,531,742 A | 7/1996 | Barken | |
| 5,573,532 A | 11/1996 | Chang | |
| 5,603,221 A | 2/1997 | Maytal | |
| 5,661,980 A | 9/1997 | Gallivan | |
| 5,702,435 A | 12/1997 | Maytal | |
| 5,716,353 A | 2/1998 | Matsura | |
| 5,733,280 A | 3/1998 | Avitall | |
| 5,741,248 A | 4/1998 | Stern | |
| 5,757,885 A | 5/1998 | Yao | |
| 5,800,487 A | 9/1998 | Mikus | |
| 5,800,488 A | 9/1998 | Crockett | |
| 5,816,052 A | 10/1998 | Foote | |
| 5,885,276 A | 3/1999 | Ammar | |
| 5,899,897 A | 5/1999 | Rabin | |
| 5,899,898 A | 5/1999 | Arless | |
| 5,899,899 A | 5/1999 | Arless | |
| 5,901,783 A | 5/1999 | Dobak, III | |
| 5,910,104 A | 6/1999 | Dobak, III | |
| 5,910,129 A * | 6/1999 | Koblish | A61B 18/1492 604/159 |
| 5,916,212 A | 6/1999 | Baust | |
| 5,924,975 A | 7/1999 | Goldowsky | |
| 5,947,960 A | 9/1999 | Griswold | |
| 5,950,444 A | 9/1999 | Matsunaga | |
| 5,957,963 A | 9/1999 | Dobak | |
| 5,978,697 A | 11/1999 | Maytal | |
| 5,993,444 A | 11/1999 | Ammar | |
| 5,997,781 A | 12/1999 | Nishikawa | |
| 6,039,730 A | 3/2000 | Rabin | |
| 6,074,412 A | 6/2000 | Mikus | |
| 6,096,068 A | 8/2000 | Dobak | |
| 6,106,518 A | 8/2000 | Wittenberger | |
| 6,139,544 A | 10/2000 | Mikus | |
| 6,142,991 A | 11/2000 | Schatzberger | |
| 6,161,543 A | 12/2000 | Cox | |
| 6,171,277 B1 | 1/2001 | Ponzi | |
| 6,179,831 B1 | 1/2001 | Bilweis | |
| 6,182,666 B1 | 2/2001 | Dobak, III | |
| 6,190,378 B1 | 2/2001 | Jarvinen | |
| 6,193,644 B1 | 2/2001 | Dobak, III | |
| 6,198,974 B1 | 3/2001 | Webster | |
| 6,235,018 B1 | 5/2001 | Lepivert | |
| 6,237,355 B1 | 5/2001 | Li | |
| 6,241,722 B1 | 6/2001 | Dobak | |
| 6,251,105 B1 | 6/2001 | Mikus | |
| 6,263,046 B1 | 7/2001 | Rogers | |
| 6,270,493 B1 | 8/2001 | Lalonde | |
| 6,307,916 B1 | 10/2001 | Rogers | |
| 6,324,852 B1 | 12/2001 | Cheng | |
| 6,341,629 B1 | 1/2002 | Clark | |
| 6,347,675 B1 | 2/2002 | Kolle | |
| 6,355,029 B1 | 3/2002 | Joye | |
| 6,368,304 B1 | 4/2002 | Aliberto | |
| 6,377,659 B1 | 4/2002 | Snyder | |
| 6,396,901 B1 | 5/2002 | Heil | |
| 6,432,174 B1 | 8/2002 | Heung | |
| 6,440,126 B1 | 8/2002 | Abboud | |
| 6,451,011 B2 | 9/2002 | Tu | |
| 6,471,694 B1 | 10/2002 | Kudaravalli | |
| 6,475,212 B2 | 11/2002 | Dobak | |
| 6,477,231 B2 | 11/2002 | Snyder | |
| 6,486,078 B1 | 11/2002 | Rangarajan | |
| 6,520,933 B1 | 2/2003 | Evans | |
| 6,527,765 B2 | 3/2003 | Kelman | |
| 6,530,420 B1 | 3/2003 | Takada | |
| 6,537,271 B1 | 3/2003 | Murray | |
| 6,544,176 B2 | 4/2003 | Mikus | |
| 6,551,309 B1 | 4/2003 | LePivert | |
| 6,554,797 B1 | 4/2003 | Worthen | |
| 6,572,610 B2 | 6/2003 | Kovalcheck | |
| 6,584,332 B2 | 6/2003 | Yoshitake | |
| 6,602,276 B2 | 8/2003 | Dobak, III | |
| 6,622,494 B1 | 9/2003 | Pourrahimi | |
| 6,622,507 B2 | 9/2003 | Cotte | |
| 6,628,002 B2 | 9/2003 | Ritz | |
| 6,648,879 B2 | 11/2003 | Joye | |
| 6,685,720 B1 | 2/2004 | Wu | |
| 6,706,037 B2 | 3/2004 | Zvuloni | |
| 6,726,653 B2 | 4/2004 | Noda | |
| 6,737,225 B2 | 5/2004 | Miller | |
| 6,746,445 B2 | 6/2004 | Abboud | |
| 6,767,346 B2 | 7/2004 | Damasco | |
| 6,812,464 B1 | 11/2004 | Sobolewski | |
| 6,848,502 B2 | 1/2005 | Bishop | |
| 6,848,458 B1 | 2/2005 | Shrinivasan | |
| 6,893,419 B2 | 5/2005 | Noda | |
| 6,893,433 B2 | 5/2005 | Lentz | |

(56) References Cited

U.S. PATENT DOCUMENTS

| | | | |
|---|---|---|---|
| 6,905,492 B2 | 6/2005 | Zvuloni | |
| 6,936,045 B2 | 8/2005 | Yu | |
| 6,989,009 B2 | 1/2006 | Lafontaine | |
| 7,004,937 B2 | 2/2006 | Lentz | |
| 7,022,120 B2 | 4/2006 | Lafontaine | |
| 7,083,612 B2 | 8/2006 | Littrup | |
| 7,110,506 B2 | 9/2006 | Radley | |
| 7,160,290 B2 | 1/2007 | Eberl | |
| 7,220,252 B2 | 5/2007 | Shah | |
| 7,220,257 B1 | 5/2007 | Lafontaine | |
| 7,195,625 B2 | 7/2007 | Lentz | |
| 7,258,161 B2 | 8/2007 | Cosley | |
| 7,273,479 B2 | 9/2007 | Littrup | |
| 7,410,484 B2 | 8/2008 | Littrup | |
| 7,507,233 B2 | 3/2009 | Littrup | |
| 7,648,497 B2 | 1/2010 | Lane | |
| 7,740,627 B2 | 6/2010 | Gammie | |
| 7,842,031 B2 | 11/2010 | Abboud | |
| 7,921,657 B2 | 4/2011 | Littrup | |
| 8,012,147 B2 | 9/2011 | Lafontaine | |
| 8,080,005 B1 | 12/2011 | Berzak | |
| 8,298,217 B2 | 10/2012 | Lane | |
| 8,382,747 B2 | 2/2013 | Abboud | |
| 8,387,402 B2 | 3/2013 | Littrup | |
| 8,475,441 B2 | 7/2013 | Babkin | |
| 8,591,503 B2 | 11/2013 | Littrup | |
| 8,641,704 B2 | 2/2014 | Werneth | |
| 8,685,014 B2 | 4/2014 | Babkin | |
| 8,740,891 B2 | 6/2014 | Babkin | |
| 8,740,892 B2 | 6/2014 | Babkin | |
| 8,845,628 B2 | 9/2014 | Babkin | |
| 8,888,768 B2 | 11/2014 | Babkin | |
| 8,945,106 B2 | 2/2015 | Arless | |
| 9,095,320 B2 | 8/2015 | Littrup | |
| 9,408,656 B2 | 8/2016 | Littrup | |
| 2001/0024485 A1 | 9/2001 | Rogers | |
| 2001/0047134 A1 | 11/2001 | Holdaway | |
| 2002/0049409 A1 | 4/2002 | Noda | |
| 2002/0062831 A1 | 5/2002 | Beyar | |
| 2002/0072741 A1 | 6/2002 | Sliwa | |
| 2002/0087152 A1 | 7/2002 | Mikus | |
| 2002/0151331 A1 | 10/2002 | Abdelmonem | |
| 2003/0040740 A1 | 2/2003 | Kovalcheck | |
| 2003/0055415 A1 | 3/2003 | Yu | |
| 2003/0195605 A1 | 10/2003 | Kovalcheck | |
| 2003/0199817 A1 | 10/2003 | Thompson | |
| 2004/0027462 A1 | 2/2004 | Hing | |
| 2004/0054363 A1* | 3/2004 | Vaska | A61B 17/2251 606/27 |
| 2004/0118144 A1 | 6/2004 | Hsu | |
| 2004/0148004 A1 | 7/2004 | Wallsten | |
| 2004/0215295 A1 | 10/2004 | Littrup | |
| 2005/0027289 A1 | 2/2005 | Castellano | |
| 2005/0119647 A1* | 6/2005 | He | A61B 18/1492 606/41 |
| 2005/0198972 A1 | 9/2005 | Lentz | |
| 2005/0209587 A1 | 9/2005 | Joye | |
| 2005/0261573 A1 | 11/2005 | Littrup | |
| 2006/0235375 A1 | 6/2006 | Littrup | |
| 2006/0212028 A1 | 9/2006 | Joye | |
| 2006/0235357 A1 | 10/2006 | Littrup | |
| 2006/0247611 A1 | 11/2006 | Abboud | |
| 2006/0253114 A1 | 11/2006 | Saadat | |
| 2008/0045935 A1* | 2/2008 | Cox | A61B 17/00234 606/21 |
| 2008/0119836 A1 | 5/2008 | Littrup | |
| 2008/0312644 A1 | 12/2008 | Fourkas | |
| 2009/0118723 A1 | 5/2009 | Lalonde | |
| 2009/0171335 A1* | 7/2009 | Cox | A61B 17/0218 606/21 |
| 2010/0057063 A1 | 3/2010 | Arless | |
| 2010/0256621 A1 | 10/2010 | Babkin | |
| 2011/0009854 A1 | 1/2011 | Babkin | |
| 2011/0054453 A1 | 3/2011 | Lalonde | |
| 2011/0162390 A1 | 7/2011 | Littrup | |
| 2011/0184399 A1 | 7/2011 | Wittenberger | |
| 2012/0053575 A1 | 3/2012 | Babkin | |
| 2012/0059364 A1 | 3/2012 | Baust | |
| 2012/0109118 A1 | 5/2012 | Lalonde | |
| 2012/0184953 A1* | 7/2012 | Spence | A61B 18/1492 606/41 |
| 2012/0209257 A1 | 8/2012 | Van Dew Weide | |
| 2012/0253336 A1 | 10/2012 | Littrup | |
| 2013/0073014 A1 | 3/2013 | Lim | |
| 2013/0204241 A1 | 8/2013 | Baust | |
| 2013/0324987 A1 | 12/2013 | Leung | |
| 2013/0331829 A1 | 12/2013 | Babkin | |
| 2013/0345688 A1 | 12/2013 | Babkin | |
| 2014/0364848 A1 | 12/2014 | Heimbecher | |
| 2015/0018809 A1 | 1/2015 | Mihalik | |
| 2015/0250524 A1 | 9/2015 | Moriarty | |
| 2016/0227600 A1 | 8/2016 | Babkin | |
| 2016/0249859 A1 | 9/2016 | Babkin | |
| 2016/0249970 A1* | 9/2016 | Yu | A61B 18/02 606/23 |

FOREIGN PATENT DOCUMENTS

| | | |
|---|---|---|
| JP | 7-136180 | 5/1995 |
| JP | 2008-515469 | 5/2008 |
| WO | WO1993008751 | 5/1993 |
| WO | WO1997049344 | 12/1997 |
| WO | WO2002058576 | 8/2002 |
| WO | WO2002096270 | 12/2002 |
| WO | WO2002011638 | 4/2003 |
| WO | 2004/064914 | 8/2004 |
| WO | WO2004064914 | 3/2005 |
| WO | 2006137887 | 12/2006 |
| WO | 2009/009398 | 1/2009 |
| WO | WO2009067497 | 5/2009 |
| WO | WO2013013098 | 1/2013 |
| WO | WO2013013099 | 1/2013 |
| WO | 2015057450 | 4/2015 |
| WO | WO2015160574 | 10/2015 |

OTHER PUBLICATIONS

Office Action dated Jul. 13, 2018 for U.S. Appl. No. 15/028,925.

Supplemental European Search Report dated Apr. 23, 2018 for EP15858716.

Australian Examination Report no. 1, dated Jul. 31, 2018 for 2014327045.

Arai, Y., et al., "Supercritical Fluids," pp. 161 and 199, ISBN 3540412484, Springer 2002.

Barron, Randall F., "Cryogenic Heat Transfer," pp. 97, 129 and 130, Taylor & Francis, 1999.

Bunch TJ, Cutler MJ. Is pulmonary vein isolation still the cornerstone in atrial fibrillation ablation? J Thorac Dis. Feb. 2015;7(2):132-41.

Callans DJ, Gerstenfeld EP, Dixit S, et al. Efficacy of repeat pulmonary vein isolation procedures in patients with recurrent atrial fibrillation. J Cardiovasc Electrophysiol 2004;15:1050-5.

Kim et al. Linear ablation in addition to circumferential pulmonary vein isolation (Dallas lesion set) does not improve clinical outcome in patients with paroxysmal atrial fibrillation: a prospective randomized study. Europace. Mar. 2015;17(3):388-95.

Kowalski M, Grimes MM, Perez FJ, et al. Histopathologic characterization of chronic radiofrequency ablation lesions for pulmonary vein isolation. J Am Coll Cardiol 2012;59:930-8.

Lide, D.R. and Keihiaian, H.V., "CRC Handbook of Thermophysical and Thermochemical Data," p. 375, CRC Press 1994.

McGann CJ, Kholmovski EG, Oakes RS, et al. New magnetic resonance imaging-based method for defining the extent of left atrial wall injury after the ablation of atrial fibrillation. J Am Coll Cardiol 2008;52:1263-71.

Ranjan R, Kato R, Zviman MM, et al. Gaps in the ablation line as a potential cause of recovery from electrical isolation and their visualization using MRI. Circ Arrhythm Electrophysiol 2011;4:279-86.

(56) References Cited

OTHER PUBLICATIONS

Ouyang F, Tilz R, Chun J, et al. Long-term results of catheter ablation in paroxysmal atrial fibrillation: lessons from a 5-year follow-up. Circulation 2010;122:2368-77.
Sawhney N, Anousheh R, Chen WC, et al. Five-year outcomes after segmental pulmonary vein isolation for paroxysmal atrial fibrillation. Am J Cardiol 2009;104:366-72.
Sun, Ya-ping, Supercritical Fluid Technology in Materials Science and Engineering, pp. 1 and 26, CRC Press 2002.
Thakore, S.B. and Bhatt, B.I., "Introduction to Process Engineering and Design," Chemical Engineering Series, pp. 27-28, McGraw-Hill 2008.
Verma A, Kilicaslan F, Pisano E, et al. Response of atrial fibrillation to pulmonary vein antrum isolation is directly related to resumption and delay of pulmonary vein conduction. Circulation 2005;112:627-35.
International Patent Application No. PCT/US2016/51954 entitled "Tissue Contact Verification System," filed Sep. 15, 2016.
International Search Report dated Feb. 2, 2017 for PCT/US2016/063882.
International Search Report dated Jan. 31, 2017 for PCT/US2016/051954.
International Search Report dated Jan. 15, 2017 for PCT/US2015/056780.
International Search Report dated Mar. 18, 2015 for PCT/US14/56839.
International Search Report dated Jan. 21, 2015 for PCT/US2014/059684.
International Search Report dated Oct. 1, 2012 for PCT/US2012/047487.
Written Opinion dated Jan. 14, 2009 for PCT/US2008/084004.
European Search Report for EP04702597 dated Sep. 18, 2007.
European Search Report for EP08852254 dated Nov. 19, 2010.
European Search Report for EP05858178.6 dated Nov. 5, 2010.
European Search Report for EP10184565 dated Feb. 21, 2011.
Stuehlinger, M., et al., "CoolLoop First: A First in Man Study to Test a Novel Circular Cryoablation System in Paroxysmal Artial Fibrillation," Journal of Artial Fibrillation, vol. 81, Issue 3, Oct.-Nov. 2015.
Skanes, Allan C., et al., "Cryoblation: Potentials and Pitfalls," doi:10.1046/j.1540-8167.2004.15106.x, Jul. 6, 2004.
Lemola, Kristina, MD, et al., "Pulmonary Vein Isolation as an End Point for Left Atrial Circumferential Ablation of Atrial Fibrillation," Journal of American College of Cardiology, vol. 46, No. 6, 2005.
Rolf, Sascha, MD, et al., "Electroanatomical Mapping of Atrial Fibrillation: Review of the Current Techniques and Advances," Journal of Artrial Fibrillation, vol. 7, Issue 4, Dec. 2014-Jan. 2015.
International Search Report dated Dec. 28, 2016 for PCT/US2016/033833.
International Search Report dated Jan. 15, 2016 for PCT/US2015/056780.

\* cited by examiner

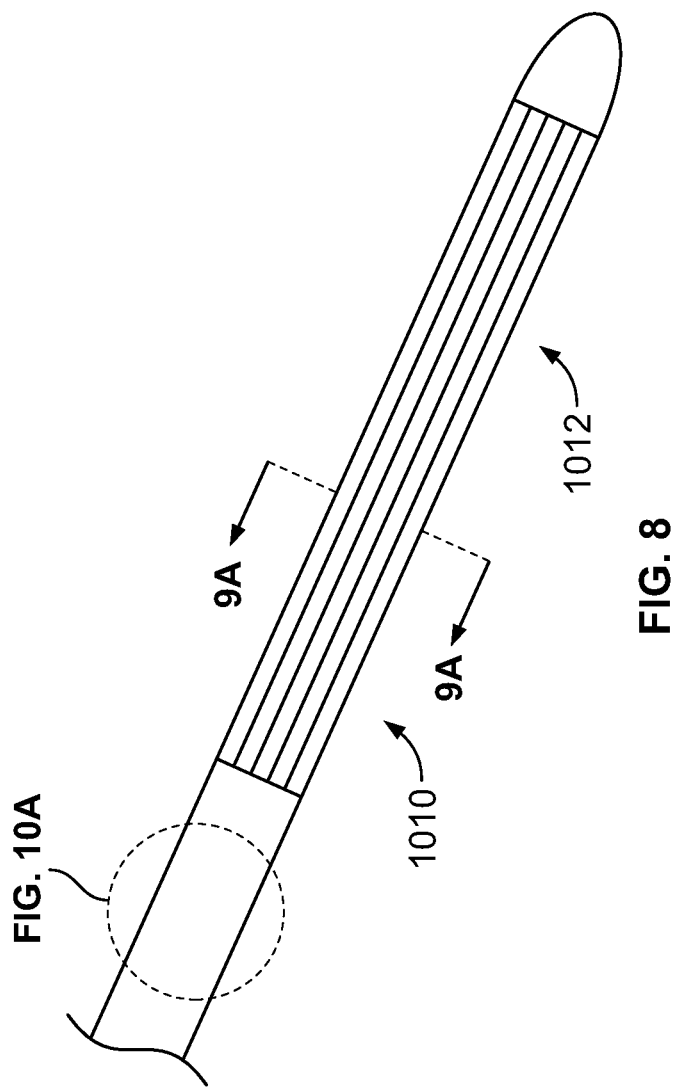

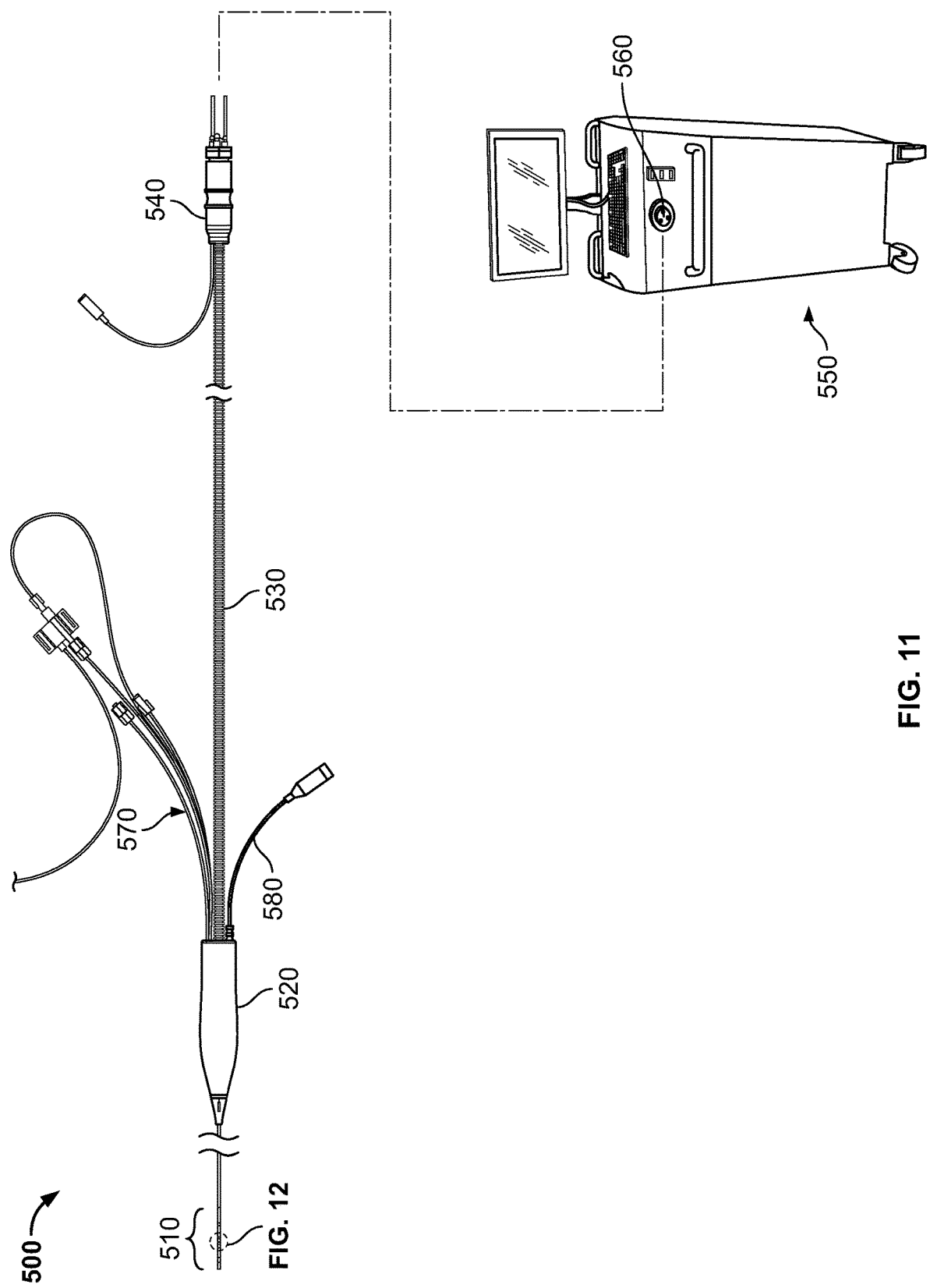

ABLATION METHOD FOR CREATING ELONGATE CONTINUOUS LESIONS ENCLOSING MULTIPLE VESSEL ENTRIES

CROSS-REFERENCE TO RELATED APPLICATIONS

This application claims the benefit of U.S. Provisional Application No. 62/260,825, filed Nov. 30, 2015, the entire contents of which are incorporated herein by reference in their entirety for all purposes.

BACKGROUND

1. Field of the Invention

Embodiments of the invention relate to cryosurgery and more particularly to cryoablation systems for the treatment of heart disease.

2. Description of the Related Art

One of the more prevalent types of heart disease or conditions is atrial fibrillation (AF). Atrial fibrillation is an irregular and often rapid heart rate. The heart's electrical signals fail to travel normally, and spread throughout the atria of the heart in a rapid, disorganized way. Failing to treat atrial fibrillation can lead to a number of undesirable consequences including heart palpitations, shortness of breath, weakness and generally poor blood flow to the body.

Various techniques are practiced to treat atrial fibrillation. One technique to treat AF is pulmonary vein isolation (PVI). PVI is performed by creating lesions circumscribing the pulmonary veins. The PVI serves to block the errant or abnormal electrical signals.

A challenge in performing PVI, however, is to obtain a lasting or permanent isolation of the pulmonary veins. This shortcoming is highlighted in various studies. In one long-term follow-up study that investigated the rate of pulmonary vein reconnection after initial isolation, 53% of 161 patients were free of AF. In 66 patients, a repeat ablation was performed for repeat arrhythmia. The rate of pulmonary vein reconnection was high at 94% (62 of 66 patients). (Ouyang F, Tilz R, Chun J, et al. Long-term results of catheter ablation in paroxysmal atrial fibrillation: lessons from a 5-year follow-up. Circulation 2010; 122:2368-77.)

One reason that some PVI treatments are not durable is because of the phenomena of pulmonary vein (or electrical) reconnection. (Sawhney N, Anousheh R, Chen W C, et al. Five-year outcomes after segmental pulmonary vein isolation for paroxysmal atrial fibrillation. Am J Cardiol 2009; 104:366-72)(Callans D J, Gerstenfeld E P, Dixit S, et al. Efficacy of repeat pulmonary vein isolation procedures in patients with recurrent atrial fibrillation. J Cardiovasc Electrophysiol 2004; 15:1050-5) (Verma A, Kilicaslan F, Pisano E, et al. Response of atrial fibrillation to pulmonary vein antrum isolation is directly related to resumption and delay of pulmonary vein conduction. Circulation 2005; 112:627-35)

Pulmonary vein reconnection may be attributed to gaps and incomplete or discontinuous isolation of the veins. (Bunch T J, Cutler M J. Is pulmonary vein isolation still the cornerstone in atrial fibrillation ablation? J Thorac Dis. 2015 February; 7 (2):132-41). Incomplete isolation is a result of residual gap(s) within the encircling lesion or lack of transmural lesions. (McGann O, Kholmovski E G, Oakes R S, et al. New magnetic resonance imaging-based method for defining the extent of left atrial wall injury after the ablation of atrial fibrillation. J Am Coll Cardiol 2008; 52:1263-71.) (Ranjan R, Kato R, Zviman M M, et al. Gaps in the ablation line as a potential cause of recovery from electrical isolation and their visualization using MRI. Circ Arrhythm Electrophysiol 2011; 4:279-86.)

Additionally, early recurrence of AF post ablation may be an early marker of incomplete pulmonary vein isolation. This is supported by a study of 12 patients that underwent a maze procedure after a failed radiofrequency ablation. Notably, myocardial biopsies showed anatomic gaps and/or non-transmural lesions in pulmonary veins that had reconnected. (Kowalski M, Grimes M M, Perez F J, et al. Histopathologic characterization of chronic radiofrequency ablation lesions for pulmonary vein isolation. J Am Coll Cardiol 2012; 59:930-8.)

This is further supported in a canine study in which endocardial conduction block was demonstrated and post procedural gaps were identified using MRI within the line of ablation. Long-term follow up data demonstrated that those pulmonary veins with the MRI-identified gaps were more likely to become electrically reconnected with symptomatic recurrences. (Ranjan R, Kato R, Zviman M M, et al. Gaps in the ablation line as potential cause of recovery from electrical isolation and their visualization using MRI. Circ Arrhythm Electrophysiol 2011; 4:279-86.)

Various attempts to solve the above referenced problem include making linear ablations in combination with circumferential pulmonary vein isolation (CPVI). One study, for example, compared clinical outcomes of CPVI with additional linear ablations and CPVI in a prospective randomized controlled study among patients with paroxysmal AF. The study enrolled 100 paroxysmal AF patients (male 75.0%, 56.4±11.6 years old) who underwent radio frequency circumferential ablation (RFCA) and were randomly assigned to the CPVI group (n=50) or the catheter Dallas lesion group (CPVI, posterior box lesion, and anterior linear ablation, n=50). The catheter Dallas lesion group required longer procedure (190.3±46.3 vs. 161.1±30.3 min, P<0.001) and ablation times (5345.4±1676.4 vs. 4027.2±878.0 s, P<0.001) than the CPVI group. Complete bidirectional conduction block rate was 68.0% in the catheter Dallas lesion group and 100% in the CPVI group. Procedure-related complication rates were not significantly different between the catheter Dallas lesion (0%) and CPVI groups (4%, P=0.157). During the 16.3±4.0 months of follow-up, the clinical recurrence rates were not significantly different between the two groups, regardless of complete bidirectional conduction block achievement after linear ablation. (Kim et al. Linear ablation in addition to circumferential pulmonary vein isolation (Dallas lesion set) does not improve clinical outcome in patients with paroxysmal atrial fibrillation: a prospective randomized study. Europace. 2015 March; 17 (3):388-95.)

Thus, in view of the above referenced study, adding more ablation points around the vein entries, and/or attempting to add a linear lesion by using point by point ablation, does not appear to be an optimal solution to prevent gap(s) along the encircling lesion. Additionally, adding multiple points and lines undesirably increases the procedure time.

Cryoballoon ablation is another technique for trying to create circumferentially shaped lesions.

U.S. Pat. No. 8,382,747 to Abboud, for example, describes a system and method for controlling the inflation, ablation, and deflation of a cryoballoon catheter. The system includes a balloon catheter, a console, a pressurized gas or liquid inflation source, and an umbilical system to deliver pressurized coolant to the balloon catheter.

Another cryoballoon catheter is the Arctic Front Advance™ Cardiac CryoAblation Catheter (manufactured by Medtronic, Minneapolis, Minn. USA).

The use of cryoballoon catheters, however, has a number of shortcomings not the least of which is that the balloon completely occludes the vein in which it is placed.

Another shortcoming is ensuring that the pressurized coolant is uniformly distributed throughout the inside of the balloon. Failure to do so may lead to incomplete isolation.

Another shortcoming is that during the inflation phase coolant may seep out of the inflatable balloon and get into the bloodstream, causing significant harm. If the balloon develops a crack, leak, rupture, or other critical structural integrity failure, coolant may quickly flow out of the catheter.

Another shortcoming that may occur during the balloon deflation phase is that the balloon may adhere to the ablated tissue causing severe damage.

Accordingly, there is a need for an improved apparatus and method to form continuous circumferential shaped lesions.

There is a need for an improved apparatus and method to treat AF and to achieve more complete, durable, and safe pulmonary vein isolation.

SUMMARY

A method for treating atrial fibrillation includes advancing an ablation catheter into the left atrium and creating a continuous circular lesion enclosing all pulmonary veins to achieve complete pulmonary vein isolation.

In embodiments, a method ablates the atrium tissue forming a box-shaped lesion enveloping and isolating all pulmonary veins. The box-shaped lesion may be formed by combining a plurality of smaller geometric closed loop shapes, each loop being an elongate continuous circular-type lesion and not a mere series of spots or point-type ablations.

In embodiments, a method isolates multiple left pulmonary veins by creating a continuous transmural circular lesion enclosing all left pulmonary veins. In a preferred embodiment, a method comprises the step of isolating multiple left pulmonary veins with a single freeze. In one method, the step of isolating comprises isolating all pulmonary veins on one side of the left atrium with a single freeze.

In embodiments, a method further comprises using the catheter to isolate the right pulmonary veins by applying a single lesion enclosing all right pulmonary veins.

In embodiments, the method further includes preventing the thermal activity arising from the ablation from damaging the inner layer of cells of the esophagus. An endoesophageal balloon (EEB) is inserted into the patient prior to the step of ablation.

In embodiments, a method creates a posterior wall lesion in the left atrium which overlaps with the first two lesions (e.g., the left and right lesions). The posterior wall lesion connects the first two lesions, and creates a floor and a roof line for isolating all the PVs. In embodiments, the EBB is placed in the patient prior to creating the posterior wall lesion to prevent collateral damage to tissues.

In embodiments, a method further comprises reading PV potentials and pacing activity to verify exit and entrance blocks. The measuring is performed using electrodes disposed along the freezing element of the catheter. In embodiments, the invention diagnoses as well as treats conditions.

The method may further comprise performing an additional or backup ablation. Subsequent to applying one of the above described first freezes enclosing the PVs, the catheter may be adjusted to perform an ancillary or backup ablation around the PVs. Applying a redundant ablation can be beneficial especially if the distance between the PVs is unusually big, presenting a challenge to complete isolation with only one circular lesion. For example, in a sub population of patients with unusually enlarged hearts, applying an ancillary or redundant lesion increases the chance of obtaining a complete and durable PVI.

In embodiments, the method further comprises performing a single vein isolation around the ostium of the single vein. The diameter of the catheter loop is reduced from the relatively large size for isolating multiple veins to the applicable size of the single vein. In embodiments, the single vein isolation is performed subsequent to ablating the larger multiple vein isolation.

Another embodiment is directed to a method of creating a lesion in cardiac tissue where the method comprises deploying a distal treatment section of an ablation catheter into a heart chamber. The method also comprises manipulating the distal treatment section against the cardiac tissue and into a curved shape that encloses a plurality of vessel entries in the heart chamber; commencing a first application of ablation energy from the distal treatment section to the cardiac tissue; and halting the first application of ablation energy to the cardiac tissue. The first application of ablation energy causes formation of a first continuous lesion in the cardiac tissue that encloses the plurality of vessel entries.

A further embodiment of the present invention is directed to a method of performing an ablation procedure in a heart cavity where the method comprises the steps of advancing an ablation catheter into the heart cavity; navigating the treatment section of the ablation catheter to a first area of interest in the heart cavity; manipulating the treatment section to form a loop-like shape to encircle cardiac tissue in the first area of interest in the heart cavity and to contact the cardiac tissue in the first area of interest in the heart cavity; performing at least one ablation cycle to create a first continuous lesion that encircles the cardiac tissue in the first area of interest in the heart cavity; navigating the treatment section of the ablation catheter to a second area of interest in the heart cavity; manipulating the treatment section to encircle and contact cardiac tissue in the second area of interest in the heart cavity; and performing at least one ablation cycle to create a second continuous lesion that encircles the cardiac tissue in the second area of interest in the heart cavity. In some embodiments, the method further comprises navigating the treatment section of the ablation catheter to a third area of interest in the heart cavity; manipulating the treatment section to encircle and contact cardiac tissue in the third area of interest in the heart cavity; and performing at least one ablation cycle to create a third continuous lesion that encircles the cardiac tissue in the third area of interest in the heart cavity. Additionally, in some embodiments, the method further comprises navigating the treatment section of the ablation catheter to a fourth area of interest in the heart cavity; manipulating the treatment section to encircle and contact cardiac tissue in the fourth area of interest in the heart cavity; and performing at least one ablation cycle to create a fourth continuous lesion that encircles the cardiac tissue in the fourth area of interest in the heart cavity.

In another embodiment, the present invention is directed to a method of performing an ablation procedure in the left atrium of the heart. The method comprises advancing an ablation catheter into the left atrium; navigating the treatment section of the ablation catheter to a first side of the left atrium to the antrum of the first side superior pulmonary vein entry and the first side inferior pulmonary vein entry; manipulating the treatment section to form a loop-like shape to encircle the first side superior pulmonary vein entry and the first side inferior pulmonary vein entry and to contact cardiac tissue surrounding the first side superior pulmonary vein entry and the first side inferior pulmonary vein entry; performing at least one ablation cycle to create a first continuous lesion that encircles the first side superior pulmonary vein entry and the first side inferior pulmonary vein entry; navigating the treatment section of the ablation catheter to a second side of the left atrium to an antrum of the second side superior pulmonary vein entry and the second side inferior pulmonary vein entry; manipulating the treatment section to encircle the second side superior pulmonary vein entry and the second side inferior pulmonary vein entry and to contact cardiac tissue surrounding the second side superior pulmonary vein entry and the second side inferior pulmonary vein entry; performing at least one ablation cycle to create a second continuous lesion that encircles the second side superior pulmonary vein entry and the second side inferior pulmonary vein entry; navigating the treatment section of the ablation catheter to a posterior wall of the left atrium; manipulating the treatment section to form a loop that overlaps the first continuous lesion and the second continuous lesion and that contacts cardiac tissue at the posterior wall; and performing at least one ablation cycle to create a third continuous lesion that overlaps the first continuous lesion and the second continuous lesion. The first continuous lesion, the second continuous lesion and the third continuous lesion form a composite continuous lesion that encircles the first side superior pulmonary vein entry, the first side inferior pulmonary vein entry, the second side superior pulmonary vein entry and the second side inferior pulmonary vein entry. In some embodiments, the method further comprises creating a lesion that extends from an area adjacent to the mitral valve annulus and intersects at least a portion of the composite continuous lesion. In some embodiments, the method further comprises navigating the treatment section of the ablation catheter to the right atrium and creating a lesion that connects the entrance of the Inferior Vena Cava and the annulus of the Tricuspid Valve and extends through the Cava Tricuspid Isthmus.

In another embodiment, the present invention is directed to a method of performing an ablation procedure in the heart. The method comprises advancing an ablation catheter into the left atrium; navigating the treatment section of the ablation catheter to a first side of the left atrium to the antrum of the first side superior pulmonary vein entry and the first side inferior pulmonary vein entry; manipulating the treatment section to form a loop-like shape to encircle the first side superior pulmonary vein entry and the first side inferior pulmonary vein entry and to contact cardiac tissue surrounding the first side superior pulmonary vein entry and the first side inferior pulmonary vein entry; performing at least one ablation cycle to create a first continuous lesion that encircles the first side superior pulmonary vein entry and the first side inferior pulmonary vein entry; navigating the treatment section of the ablation catheter to a second side of the left atrium to an antrum of the second side superior pulmonary vein entry and the second side inferior pulmonary vein entry; manipulating the treatment section to encircle the second side superior pulmonary vein entry and the second side inferior pulmonary vein entry and to contact cardiac tissue surrounding the second side superior pulmonary vein entry and the second side inferior pulmonary vein entry; performing at least one ablation cycle to create a second continuous lesion that encircles the second side superior pulmonary vein entry and the second side inferior pulmonary vein entry; navigating the treatment section of the ablation catheter to a posterior wall of the left atrium; manipulating the treatment section to form a loop that overlaps the first continuous lesion and the second continuous lesion and that contacts cardiac tissue at the posterior wall; and performing at least one ablation cycle to create a third continuous lesion that overlaps the first continuous lesion and the second continuous lesion. The first continuous lesion, the second continuous lesion and the third continuous lesion form a composite continuous lesion that encircles the first side superior pulmonary vein entry, the first side inferior pulmonary vein entry, the second side superior pulmonary vein entry and the second side inferior pulmonary vein entry. In some embodiments, the method further comprises creating a lesion that extends from an area adjacent to the mitral valve annulus and intersects at least a portion of the composite continuous lesion.

A near critical fluid based cryoablation catheter includes a distal treatment section for delivering energy to the target tissue. The shape of the distal treatment section is preset and adjustable to make continuous contact with curved anatomies such as the antrum surrounding all the pulmonary veins on the left or right side of the left atrium.

In embodiments, an outer sheath coaxially surrounds the distal treatment section. The outer sheath serves to constrain the distal section in a first substantially linear configuration as the catheter is advanced into position. Once the catheter is in position, the distal treatment section is deployed from the outer sheath. In an embodiment, the distal treatment section is deployed by axial movement of the inner treatment section relative to the outer sheath.

In embodiments, the distal treatment section comprises a bundle of flexible energy delivering elements and a mechanical core assembly. The bundle of tubular elements circulates a near critical fluid there through, freezing the target tissue.

The mechanical core extends through the distal treatment section and causes the treatment section to assume a preset shape when not constrained by the outer sheath. In embodiments, the unconstrained shape is a ring or loop configuration suitable for enclosing a plurality of pulmonary vein entries.

In embodiments, the mechanical core includes one or more control members and spine elements. The spine elements may have preset shapes and may bias the catheter in one direction or another. Movement of a pull wire causes the distal treatment section to articulate or adjust shape.

In embodiments, movement of the pull wire reduces the diameter of a preset ring shape.

Additional structures, layers, and materials such as springs and coils may be incorporated into sections of the catheter to reduce or modify the flexibility and bend during the procedure. In embodiments, the intermediate section comprises a coil thereby reducing the flexibility in the intermediate section relative to the distal section.

In embodiments, electrodes are disposed along the distal treatment section. The electrodes allow the catheter to diagnose electrical activity in the tissue. In embodiments, the electrodes read PV potentials and pacing to verify exit and entrance blocks. Consequently, the catheter operates as a two-in-one device to both treat and diagnose the heart condition with a single device.

In embodiments, the catheter includes an ergonomic handle. The handle includes one or more buttons, levers, knobs, and hubs which cooperate with the pull wires and other functional elements to allow an operator to turn, rotate, articulate, and shape the distal treatment section. Extending proximally from the handle is an umbilical cord. The umbilical cord fluidly couples the handle to a cryogen source or generator.

An endovascular near critical fluid based cryoablation system for creating a lesion in tissue comprises a near critical fluid pressure source or generator, a near critical fluid cooler for cooling the near critical fluid, a near critical fluid based cryoablation catheter in fluid communication with the generator, and a controller operable to control the cooling power delivered from a distal treatment section of the catheter to the tissue to cool the tissue.

In embodiments, the distal treatment section is adjustable to make a ring or elliptical shape. The ring-shaped distal treatment section creates a lesion having a matching ring or elliptical shape. The ring-shaped treatment section is large enough to enclose or circumscribe multiple pulmonary vein entries (e.g., both superior and inferior pulmonary vein entries).

The distal treatment section is preferably elongate and continuous. Application of the cooling energy creates a continuous lesion, and not a series of spots such as in some prior art point-ablation techniques.

In embodiments, the distal treatment section comprises a bundle/plurality of energy delivering tubular elements.

In embodiments, the catheter comprises a protective barrier and a liquid-filled annular gap surrounding the bundle of energy delivering elements.

In some embodiments, the invention is directed to a cryoablation catheter for performing an ablation procedure in a heart cavity where the cryoablation catheter comprises a distal treatment section including at least one fluid delivery tube and at least one fluid return tube. The distal treatment section is configured: for delivery into the heart cavity to a first area of interest in the heart cavity; to be manipulated to form a loop-like shape to encircle cardiac tissue in the first area of interest in the heart cavity and to contact the cardiac tissue in the first area of interest in the heart cavity; to flow a cryogen through the at least one fluid delivery tube and at least one fluid return tube to create a first continuous lesion that encircles the cardiac tissue in the first area of interest in the heart cavity; for delivery to a second area of interest in the heart cavity; to be manipulated to encircle and contact cardiac tissue in the second area of interest in the heart cavity; and to flow a cryogen through the at least one fluid delivery tube and at least one fluid return tube to create a second continuous lesion that encircles the cardiac tissue in the second area of interest in the heart cavity. In some embodiments, the distal treatment section is further configured: for delivery to a third area of interest in the heart cavity; to be manipulated to encircle and contact cardiac tissue in the third area of interest in the heart cavity; and to flow a cryogen through the at least one fluid delivery tube and at least one fluid return tube to create a third continuous lesion that encircles the cardiac tissue in the third area of interest in the heart cavity. In some embodiments, the distal treatment section is further configured: for delivery to a fourth area of interest in the heart cavity; to be manipulated to encircle and contact cardiac tissue in the fourth area of interest in the heart cavity; and to flow a cryogen through the at least one fluid delivery tube and at least one fluid return tube to create a fourth continuous lesion that encircles the cardiac tissue in the fourth area of interest in the heart cavity.

In embodiments, the controller comprises a processor programmed to monitor pressure of the liquid filled annular gap, and to halt delivery of the cooling energy based on the pressure.

In embodiments, a system further includes an endoesophageal balloon (EBB). The EEB is advanced into the esophagus in the vicinity of the heart. A warming liquid is delivered through the EBB, serving to prevent the cold temperature from reaching the inner layer of cells of the esophagus, and to prevent formation of an atrio-esophageal fistula. The EBB is particularly useful when creating posterior wall lesions in the left atrium.

Cryoablation systems described herein are capable of freezing tissue during the treatment of AF to significantly lower temperature. The cryoablation systems described herein have significantly shorter freezing durations. For example, in embodiments of the subject invention, an elongate circular continuous lesion for a complete isolation of all left or right PVs could be performed within one minute.

Additionally, unlike the above mentioned cryoballoon apparatus', embodiments of the subject invention effectively create continuous lesions without occluding blood flow.

Additionally, the length of lesions are continuous and not a series of spots or point ablations. In embodiments, the lesions have a circumferential length ranging from 6-16 cm, and more preferably between 8-10 cm.

Additionally, a method is described herein to create a box-shaped lesion in the left atrium for complete PVI using only one catheter during a short and easy procedure.

In embodiments, the box-shaped lesion is formed in combination with use of an EBB. The EBB serves to limit the risk of forming an atrio-esophageal fistula during treatment of the posterior wall of the left atrium.

In embodiments, the catheter systems achieve cooling power without vapor lock by transporting the cooling fluid near its critical point in the phase diagram. In embodiments, the distal treatment section designs described herein create elongate continuous lesions spanning the full thickness of the heart wall.

In embodiments, the catheter systems include protective barriers to contain leaks and to eliminate the dangers arising there from.

The description, objects and advantages of embodiments of the present invention will become apparent from the detailed description to follow, together with the accompanying drawings.

BRIEF DESCRIPTION OF THE DRAWINGS

FIG. 8 is a perspective view of another embodiment of a cryoablation catheter having a flexible distal treatment section;

FIG. 11 is a perspective view of another embodiment of a cryoablation catheter having a flexible distal treatment section;

DETAILED DESCRIPTION

Figure 1:
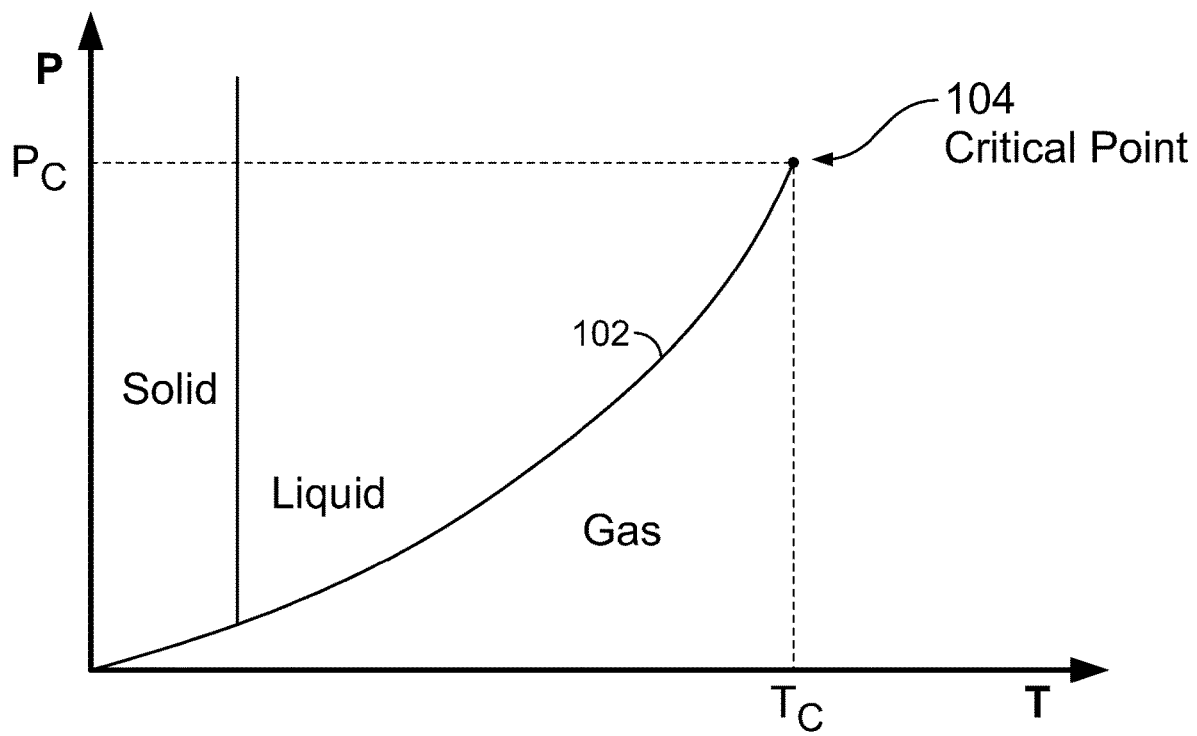
FIG. 1 illustrates a typical cryogen phase diagram.

It is to be understood that the embodiments of the invention described herein are not limited to particular variations set forth herein as various changes or modifications may be made to the embodiments of the invention described and equivalents may be substituted without departing from the spirit and scope of the embodiments of the invention. As will be apparent to those of skill in the art upon reading this disclosure, each of the individual embodiments described and illustrated herein has discrete components and features that may be readily separated from or combined with the features of any of the other several embodiments without departing from the scope or spirit of the embodiments of the present invention. In addition, many modifications may be made to adapt a particular situation, material, composition of matter, process, process act(s) or step(s) to the objective(s), spirit or scope of the embodiments of the present invention. All such modifications are intended to be within the scope of the claims made herein.

Moreover, while methods may be depicted in the drawings or described in the specification in a particular order, such methods need not be performed in the particular order shown or in sequential order, and that all methods need not be performed, to achieve desirable results. Other methods that are not depicted or described can be incorporated in the example methods and processes. For example, one or more additional methods can be performed before, after, simultaneously, or between any of the described methods. Further, the methods may be rearranged or reordered in other implementations. Also, the separation of various system components in the implementations described above should not be understood as requiring such separation in all implementations, and it should be understood that the described components and systems can generally be integrated together in a single product or packaged into multiple products. Additionally, other implementations are within the scope of this disclosure.

Conditional language, such as "can," "could," "might," or "may," unless specifically stated otherwise, or otherwise understood within the context as used, is generally intended to convey that certain embodiments include or do not include, certain features, elements, and/or steps. Thus, such conditional language is not generally intended to imply that features, elements, and/or steps are in any way required for one or more embodiments.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It will be understood that when an element is referred to as being "connected" or "coupled" to another element, it can be directly connected or coupled to the other element or intervening elements may be present. In contrast, if an element is referred to as being "directly connected" or "directly coupled" to another element, there are no intervening elements present.

It will also be understood that, although the terms first, second, etc. may be used herein to describe various elements, these elements should not be limited by these terms. These terms are only used to distinguish one element from another. Thus, a first element could be termed a second element without departing from the teachings of the present invention.

Language of degree used herein, such as the terms "approximately," "about," "generally," and "substantially," represent a value, amount, or characteristic close to the stated value, amount, or characteristic that still performs a desired function or achieves a desired result. For example, the terms "approximately," "about," "generally," and "substantially" may refer to an amount that is within less than or equal to 10% of, within less than or equal to 5% of, within less than or equal to 1% of, within less than or equal to 0.1% of, and within less than or equal to 0.01% of the stated amount. If the stated amount is 0 (e.g., none, having no), the above recited ranges can be specific ranges, and not within a particular % of the value. Additionally, numeric ranges are inclusive of the numbers defining the range, and any individual value provided herein can serve as an endpoint for a range that includes other individual values provided herein. For example, a set of values such as 1, 2, 3, 8, 9, and 10 is also a disclosure of a range of numbers from 1-10, from 1-8, from 3-9, and so forth.

Some embodiments have been described in connection with the accompanying drawings. The figures are drawn to scale, but such scale should not be limiting, since dimensions and proportions other than what are shown are contemplated and are within the scope of the disclosed inventions. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

While a number of embodiments and variations thereof have been described in detail, other modifications and methods of using the same will be apparent to those of skill in the art. Accordingly, it should be understood that various applications, modifications, materials, and substitutions can be made of equivalents without departing from the unique and inventive disclosure herein or the scope of the claims.

All existing subject matter mentioned herein (e.g., publications, patents, patent applications and hardware) is incorporated by reference herein in its entirety except insofar as the subject matter may conflict with that of the present invention (in which case what is present herein shall prevail).

Embodiments of the invention make use of thermodynamic processes using cryogens that provide cooling without encountering the phenomenon of vapor lock.

Cryogen Phase Diagram and Near Critical Point

This application uses phase diagrams to illustrate various thermodynamic processes. An example phase diagram is shown in FIG. 1. The phase diagram includes axes that correspond to pressure P and temperature T, and a phase line 102 that delineates the locus of all (P, T) points where liquid and gas coexist. For (P, T) values to the left of the phase line 102, the cryogen is in a liquid state, generally achieved with higher pressures and lower temperatures, while (P, T) values to the right of the phase line 102 define regions where the cryogen is in a gaseous state, generally achieved with lower pressures and higher temperatures. The phase line 102 ends abruptly in a single point known as the critical point 104. In the case of nitrogen $N_2$, the critical point is at $P_c$=3.396 MPa and $T_c$=−147.15° C.

When a fluid has both liquid and gas phases present during a gradual increase in pressure, the system moves up along the liquid-gas phase line 102. In the case of $N_2$, the liquid at low pressures is up to two hundred times more dense than the gas phase. A continual increase in pressure causes the density of the liquid to decrease and the density of the gas phase to increase, until they are equal only at the critical point 104. The distinction between liquid and gas disappears at the critical point 104. The blockage of forward flow by gas expanding ahead of the liquid cryogen ("vapor lock") is thus avoided when a cryogen flows at conditions surrounding the critical point, defined herein as "near-critical conditions." Factors that allow greater departure from the critical point while maintaining a functional flow include greater speed of cryogen flow, larger diameter of the flow lumen and lower heat load upon the thermal exchanger, or cryo-treatment region.

As the critical point is approached from below, the vapor phase density increases and the liquid phase density decreases until right at the critical point, where the densities of these two phases are exactly equal. Above the critical point, the distinction of liquid and vapor phases vanishes, leaving only a single, supercritical phase, where the fluid has the properties of both a liquid and a gas (i.e., a dense fluid without surface tension capable of frictionless flow).

Van der Waals thermodynamic equation of state is a well-established equation for describing gases and liquids:

$$(p+3/v^2)(3v-1)=8t \qquad [\text{Eq. 1}]$$

where $p=P/P_c$, $v=V/V_c$, and $t=T/T_c$, and $P_c$, $V_c$, and $T_c$ are the critical pressure, critical molar volume, and the critical temperature respectively.

The variables v, p, and t are often referred to as the "reduced molar volume," the "reduced pressure," and the "reduced temperature," respectively. Hence, any two substances with the same values of p, v, and t are in the same thermodynamic state of fluid near its critical point. Eq. 1 is thus referred to as embodying the "Law of Corresponding States." This is described more fully in H. E. Stanley,

*Introduction to Phase Transitions and Critical Phenomena* (Oxford Science Publications, 1971), the entire disclosure of which is incorporated herein by reference in its entirety for all purposes.

In embodiments of the present invention, the reduced pressure p is fixed at a constant value of approximately one, and hence at a fixed physical pressure near the critical pressure, while the reduced temperature t varies with the heat load applied to the device. If the reduced pressure p is a constant set by the engineering of the system, then the reduced molar volume v is an exact function of the reduced temperature t.

In other embodiments of the present invention, the operating pressure p may be adjusted so that over the course of variations in the temperature t of the device, v is maintained below some maximum value at which the vapor lock condition will result. It is generally desirable to maintain p at the lowest value at which this is true because boosting the pressure to achieve higher values of p may involve use of a more complex and more expensive compressor, resulting in more expensive procurement and maintenance of the entire apparatus support system and lower overall cooling efficiency.

The conditions for v depend in a complex way on the volume flow rate dV/dt, the heat capacity of the liquid and vapor phases, and the transport properties such as the thermal conductivity, viscosity, etc., in both the liquid and the vapor. The exact relationship is not derived here in closed form algebraically, but may be determined numerically by integrating the model equations that describe mass and heat transport within the cooling device. Conceptually, vapor lock occurs when the rate of heating of the tip (or other device structure for transporting the cryogen and cooling the tissue) produces the vapor phase. The cooling power of this vapor phase, which is proportional to the flow rate of the vapor multiplied by its heat capacity divided by its molar volume, is not able to keep up with the rate of heating to the tip. When this occurs, more and more of the vapor phase is formed in order to absorb the excess heat through the conversion of the liquid phase to vapor in the cryogen flow. This creates a runaway condition where the liquid converts into vapor phase to fill the tip, and effectively all cryogen flow stops due to the large pressure that results in this vapor phase as the heat flow into the tip increases its temperature and pressure rapidly. This condition is called "vapor lock."

In accordance with one embodiment of the present invention, the liquid and vapor phases are substantially identical in their molar volume. The cooling power is at the critical point, and the cooling system avoids vapor lock. Additionally, at conditions slightly below the critical point, the apparatus may avoid vapor lock as well.

Cryoablation System

Figure 2:
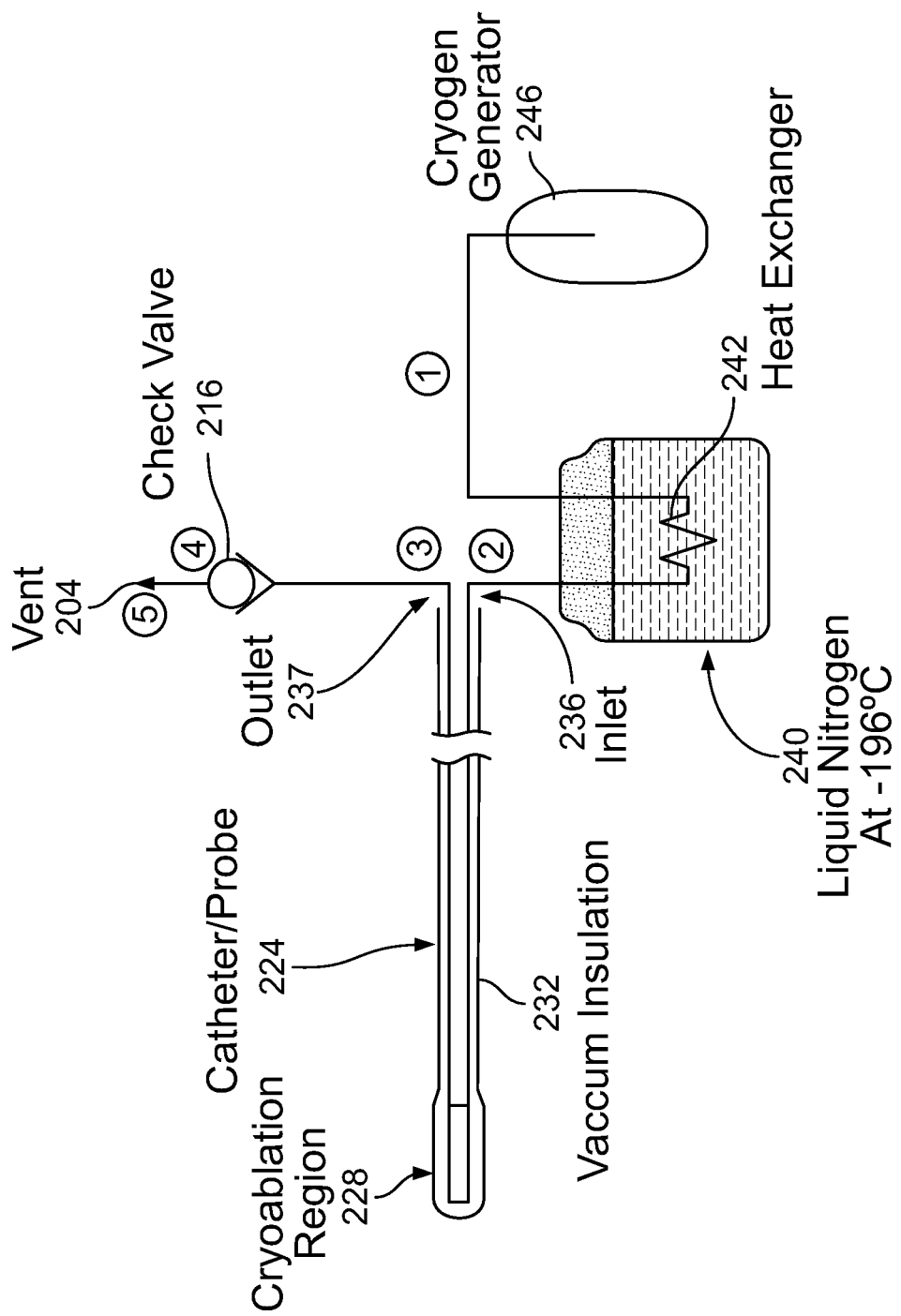
FIG. 2 is a schematic illustration of a cryogenic cooling system.
Figure 3:
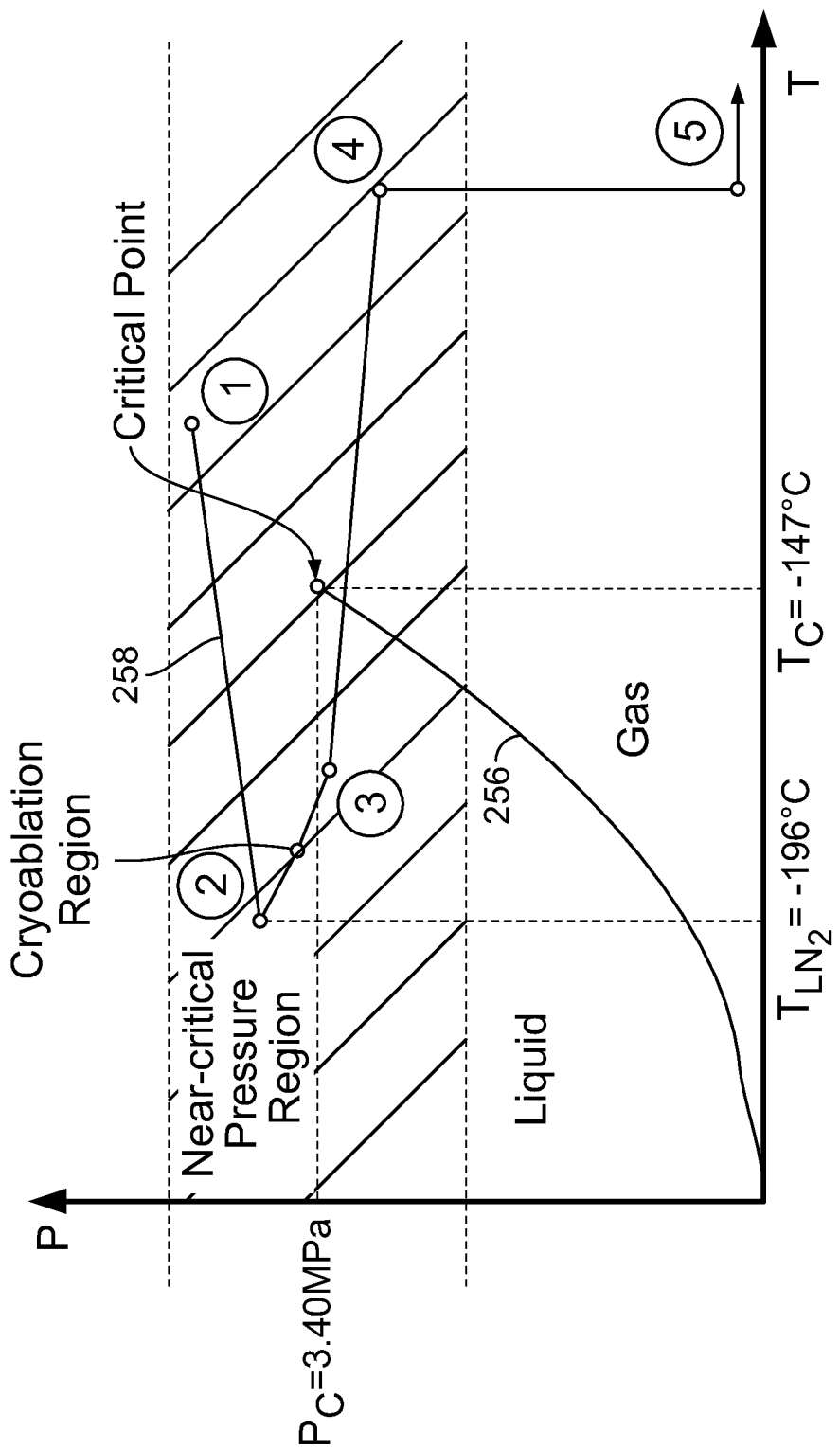
FIG. 3 is a cryogen phase diagram corresponding to the system shown in FIG. 2 where the cryogen is $N_2$.

FIG. 2 provides a schematic illustration of a structural arrangement for a cryogenic system in one embodiment, and FIG. 3 provides a phase diagram that illustrates a thermodynamic path taken by the cryogen when the system of FIG. 2 is operated. The circled numerical identifiers in the two figures correspond so that a physical position is indicated in FIG. 2 where operating points identified along the thermodynamic path are achieved. The following description thus sometimes makes simultaneous reference to both the structural drawing of FIG. 2 and to the phase diagram of FIG. 3 in describing physical and thermodynamic aspects of the cooling flow.

For purposes of illustration, both FIGS. 2 and 3 make specific reference to a nitrogen cryogen, but this is not intended to be limiting. The invention may more generally be used with any suitable cryogen such as, for example, argon, neon, helium, hydrogen, and oxygen.

In FIG. 3, the liquid-gas phase line is identified with reference label 256 and the thermodynamic path followed by the cryogen is identified with reference label 258.

A cryogenic generator 246 is used to supply the cryogen at a pressure that exceeds the critical-point pressure $P_c$ for the cryogen at its outlet, referenced in FIGS. 2 and 3 by label $\hat{1}$. The cooling cycle may generally begin at any point in the phase diagram having a pressure above or slightly below $P_c$, although it is advantageous for the pressure to be near the critical-point pressure $P_c$. The cooling efficiency of the process described herein is generally greater when the initial pressure is near the critical-point pressure $P_c$ so that at higher pressures there may be increased energy requirements to achieve the desired flow. Thus, embodiments may sometimes incorporate various higher upper boundary pressure but generally begin near the critical point, such as between 0.8 and 1.2 times $P_c$, and in one embodiment at about 0.85 times $P_c$.

As used herein, the term "near critical" is meant to refer to near the liquid-vapor critical point. Use of this term is equivalent to "near a critical point" and it is the region where the liquid-vapor system is adequately close to the critical point, where the dynamic viscosity of the fluid is close to that of a normal gas and much less than that of the liquid; yet, at the same time its density is close to that of a normal liquid state. The thermal capacity of the near critical fluid is even greater than that of its liquid phase. The combination of gas-like viscosity, liquid-like density and very large thermal capacity makes it a very efficient cooling agent. Reference to a near critical point refers to the region where the liquid-vapor system is adequately close to the critical point so that the fluctuations of the liquid and vapor phases are large enough to create a large enhancement of the heat capacity over its background value. The near critical temperature is a temperature within ±10% of the critical point temperature. The near critical pressure is between 0.8 and 1.2 times the critical point pressure.

Referring again to FIG. 2, the cryogen is flowed through a tube, at least part of which is surrounded by a reservoir 240 of the cryogen in a liquid state, reducing its temperature without substantially changing its pressure. In FIG. 2, reservoir is shown as liquid $N_2$, with a heat exchanger 242 provided within the reservoir 240 to extract heat from the flowing cryogen. Outside the reservoir 240, thermal insulation may be provided around the tube to prevent unwanted warming of the cryogen as it is flowed from the cryogen generator 246. At point $\hat{2}$, after being cooled by being brought into thermal contact with the liquid cryogen, the cryogen has a lower temperature but is at substantially the initial pressure. In some instances, there may be a pressure change, as is indicated in FIG. 3 in the form of a slight pressure decrease, provided that the pressure does not drop substantially below the critical-point pressure $P_c$, i.e. does not drop below the determined minimum pressure. In the example shown in FIG. 3, the temperature drop as a result of flowing through the liquid cryogen is about 50° C.

The cryogen is then provided to a device for use in cryogenic applications. In the exemplary embodiment shown in FIG. 2, the cryogen is provided to an inlet 236 of a catheter 224, such as may be used in medical cryogenic endovascular applications, but this is not a requirement.

Indeed, the form of the medical device may vary widely and include without limitation: instruments, appliances, catheters, devices, tools, apparatus', and probes regardless of whether such probe is short and rigid, or long and flexible, and regardless of whether it is intended for open, minimal, non-invasive, manual or robotic surgeries.

In embodiments, the cryogen may be introduced through a proximal portion of a catheter, continue along a flexible intermediate section of the catheter, and into the distal treatment section of the catheter. As the cryogen is transported through the catheter, and across the cryoablation treatment region 228, between labels $\hat{2}$ and $\hat{3}$ in FIGS. 2 and 3, there may be a slight change in pressure and/or temperature of the cryogen as it moves through the interface with the device, e.g. cryoablation region 228 in FIG. 2. Such changes may typically show a slight increase in temperature and a slight decrease in pressure. Provided the cryogen pressure remains above the determined minimum pressure (and associated conditions), slight increases in temperature do not significantly affect performance because the cryogen simply moves back towards the critical point without encountering the liquid-gas phase line 256, thereby avoiding vapor lock.

Flow of the cryogen from the cryogen generator 246 through the catheter 224 or other device may be controlled in the illustrated embodiment with an assembly that includes a check valve 216, a flow impedance, and/or a flow controller. The catheter 224 itself may comprise a vacuum insulation 232 (e.g., a cover or jacket) along its length and may have a cold cryoablation region 228 that is used for the cryogenic applications. Unlike a Joule-Thomson probe, where the pressure of the working cryogen changes significantly at the probe tip, these embodiments of the invention provide relatively little change in pressure throughout the apparatus. Thus, at point $\hat{4}$, the temperature of the cryogen has increased approximately to ambient temperature, but the pressure remains elevated. By maintaining the pressure above or near the critical-point pressure $P_c$ as the cryogen is transported through the catheter, vapor lock are avoided.

The cryogen pressure returns to ambient pressure at point $\hat{5}$. The cryogen may then be vented through vent 204 at substantially ambient conditions.

Examples of cryoablation systems, their components, and various arrangements are described in the following commonly-assigned U.S. patents and U.S. patent applications: U.S. patent application Ser. No. 10/757,768, which issued as U.S. Pat. No. 7,410,484, on Aug. 12, 2008 entitled "CRYOTHERAPY PROBE," filed Jan. 14, 2004 by Peter J. Littrup et al.; U.S. patent application Ser. No. 10/757,769, which issued as U.S. Pat. No. 7,083,612 on Aug. 1, 2006, entitled "CRYOTHERAPY SYSTEM," filed Jan. 14, 2004 by Peter J. Littrup et al.; U.S. patent application Ser. No. 10/952,531, which issued as U.S. Pat. No. 7,273,479 on Sep. 25, 2007 entitled "METHODS AND SYSTEMS FOR CRYOGENIC COOLING," filed Sep. 27, 2004 by Peter J. Littrup et al.; U.S. patent application Ser. No. 11/447,356, which issued as U.S. Pat. No. 7,507,233 on Mar. 24, 2009 entitled "CRYOTHERAPY SYSTEM," filed Jun. 6, 2006 by Peter Littrup et al.; U.S. patent application Ser. No. 11/846,226, which issued as U.S. Pat. No. 7,921,657 on Apr. 12, 2011 entitled "METHODS AND SYSTEMS FOR CRYOGENIC COOLING," filed Aug. 28, 2007 by Peter Littrup et al.; U.S. patent application Ser. No. 12/018,403, which issued as U.S. Pat. No. 8,591,503 on Nov. 26, 2013 entitled "CRYOTHERAPY PROBE," filed Jan. 23, 2008 by Peter Littrup et al.; U.S. patent application Ser. No. 13/046,274, which issued as U.S. Pat. No. 8,387,402 on Mar. 5, 2013 entitled "METHODS AND SYSTEMS FOR CRYOGENIC COOLING," filed Mar. 11, 2011 by Peter Littrup et al.; U.S. patent application Ser. No. 14/087,947, which is pending entitled "CRYOTHERAPY PROBE," filed Nov. 22, 2013 by Peter Littrup et al.; U.S. patent application Ser. No. 12/744,001, which issued as U.S. Pat. No. 8,740,891, on Jun. 3, 2014 entitled "FLEXIBLE MULTI-TUBULAR CRYOPROBE," filed Jul. 29, 2010 by Alexei Babkin et al.; U.S. patent application Ser. No. 12/744,033, which issued as U.S. Pat. No. 8,740,892, on Jun. 3, 2014 entitled "EXPANDABLE MULTI-TUBULAR CRYOPROBE," filed Jul. 29, 2010 by Alexei Babkin et al. and U.S. patent application Ser. No. 14/915,632 entitled "ENDOVASCULAR NEAR CRITICAL FLUID BASED CRYOABLATION CATHETER AND RELATED METHODS," filed Sep. 22, 2014 by Alexei Babkin, et al., the contents of each of the above-identified U.S. patents/applications are incorporated herein by reference in their entireties for all purposes.

Figure 4:
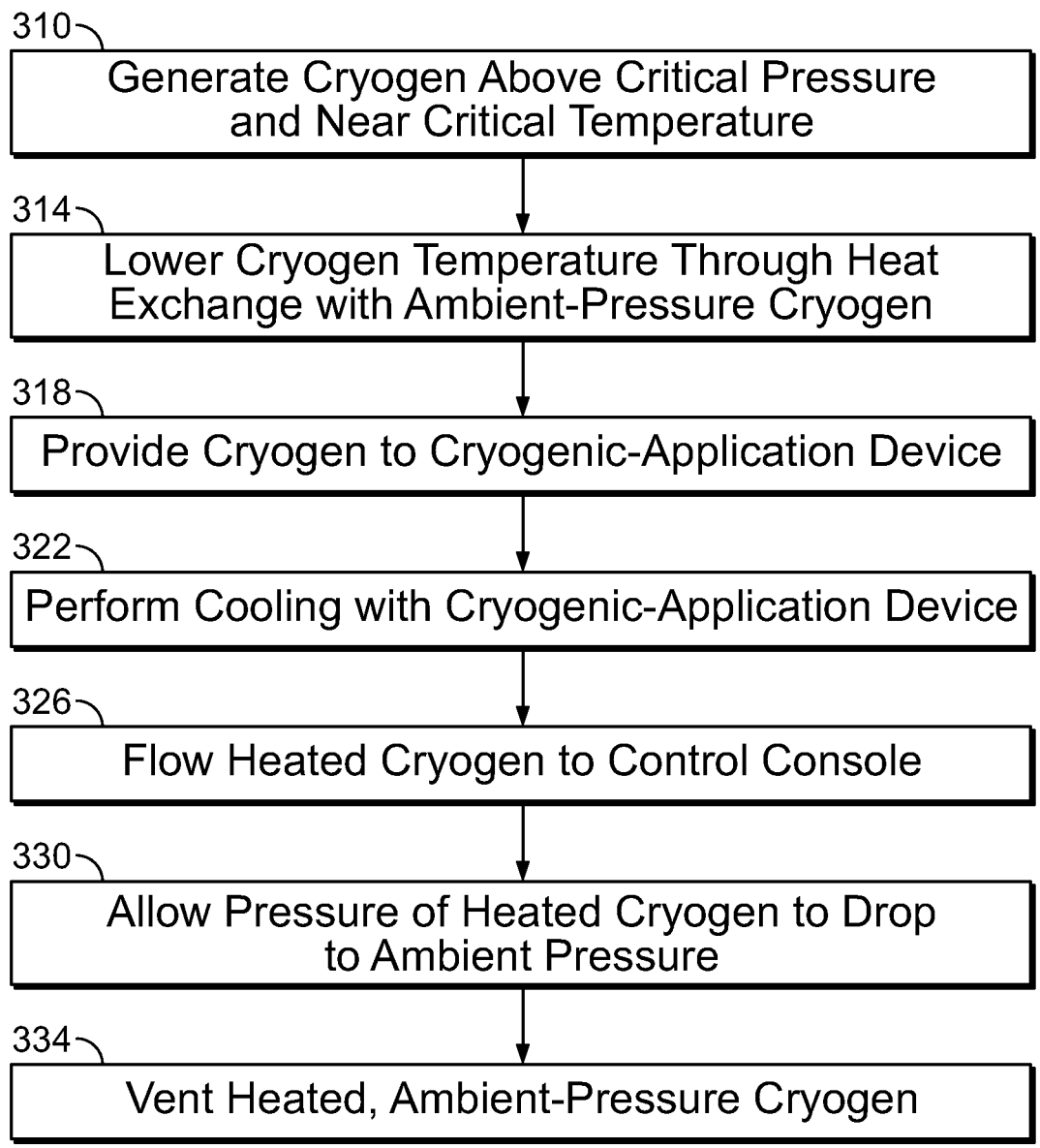
FIG. 4 provides a flow diagram that summarizes aspects of the cooling system of FIG. 2.

A method for cooling a target tissue in which the cryogen follows a thermodynamic path similar to that shown in FIG. 3 is illustrated with the flow diagram of FIG. 4. At block 310, the cryogen is generated with a pressure that exceeds the critical-point pressure and is near the critical-point temperature. The temperature of the generated cryogen is lowered at block 314 through heat exchange with a substance having a lower temperature. In some instances, this may conveniently be performed by using heat exchange with an ambient-pressure liquid state of the cryogen, although the heat exchange may be performed under other conditions in different embodiments. For example, a different cryogen might be used in some embodiments, such as by providing heat exchange with liquid nitrogen when the working fluid is argon. Also, in other alternative embodiments, heat exchange may be performed with a cryogen that is at a pressure that differs from ambient pressure, such as by providing the cryogen at lower pressure to create a colder ambient.

The further cooled cryogen is provided at block 318 to a cryogenic-application device, which may be used for a cooling application at block 322. The cooling application may comprise chilling and/or freezing, depending on whether an object is frozen with the cooling application. The temperature of the cryogen is increased as a result of the cryogen application, and the heated cryogen is flowed to a control console at block 326. While there may be some variation, the cryogen pressure is generally maintained greater than the critical-point pressure throughout blocks 310-326; the principal change in thermodynamic properties of the cryogen at these stages is its temperature. At block 330, the pressure of the heated cryogen is then allowed to drop to ambient pressure so that the cryogen may be vented, or recycled, at block 334. In other embodiments, the remaining pressurized cryogen at block 326 may also return along a path to block 310 to recycle rather than vent the cryogen at ambient pressure.

Cryoablation Catheter

Figure 5:
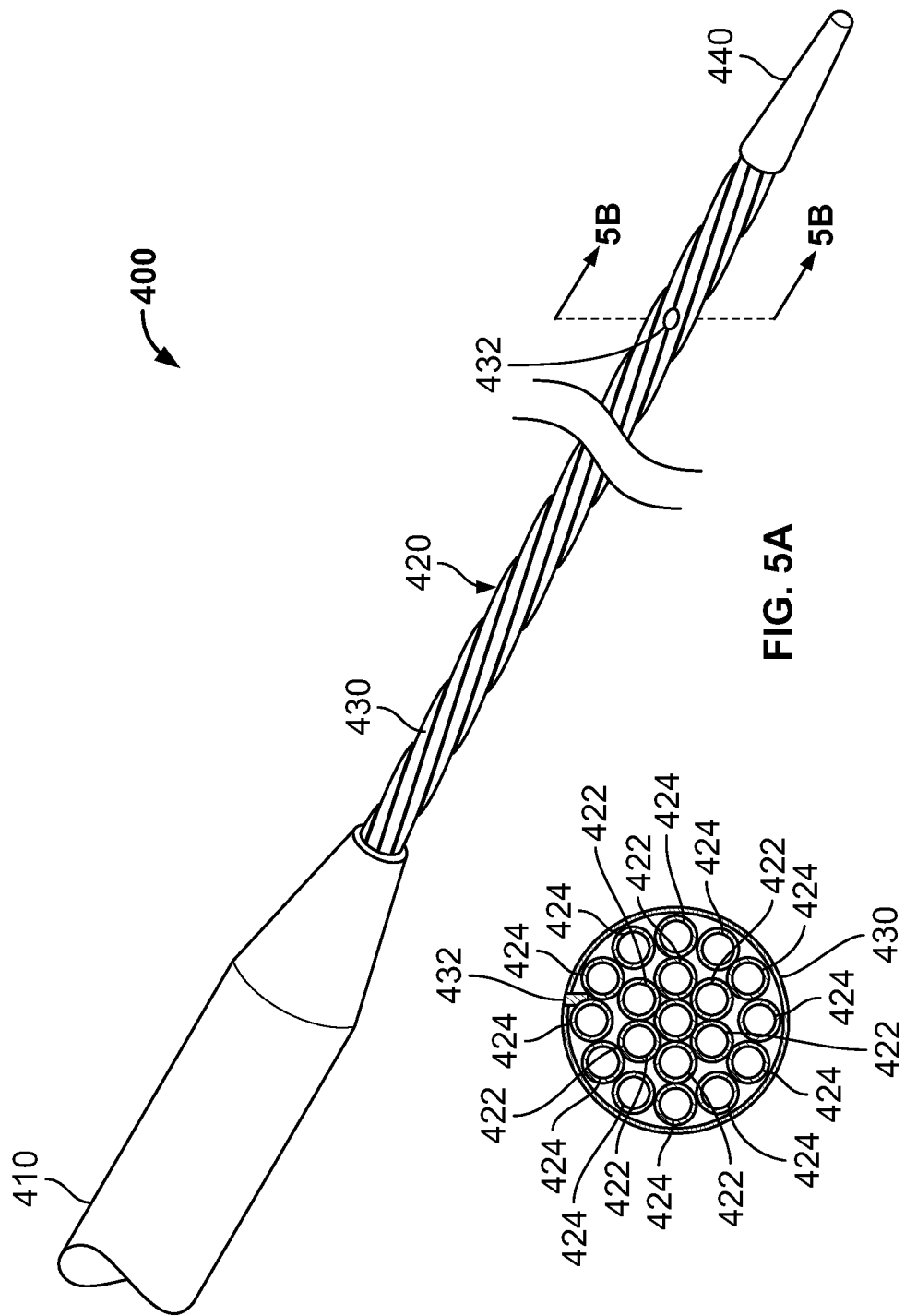
FIG. 5A is a perspective view of a cryoablation catheter, according to an embodiment of the invention.
FIG. 5B is a cross-sectional view taken along line 5B-5B of FIG. 5A.

The cryoablation apparatus of the present invention may have a wide variety of configurations. For example, one embodiment of the present invention is a flexible catheter 400 as shown in FIG. 5A. The catheter 400 includes a proximally disposed housing or connector 410 adapted to fluidly connect to a fluid source (not shown).

A plurality of fluid transfer tubes 420 are shown extending from the connector 410. These tubes include a set of inlet fluid transfer tubes 422 for receiving the inlet flow from the connector and a set of outlet fluid transfer tubes 424 for discharging flow from the connector 410.

In embodiments each of the fluid transfer tubes is formed of material that maintains flexibility in a full range of temperatures from −200° C. to ambient temperature. In embodiments, the fluid transfer tubes 420 are formed of annealed stainless steel or a polymer such as polyimide. In such configurations, the material may maintain flexibility at near critical temperature. In embodiments, each fluid transfer tube has an inside diameter in a range of between about 0.1 mm and 1 mm (preferably between about 0.2 mm and 0.5 mm). Each fluid transfer tube may have a wall thickness in a range of between about 0.01 mm and 0.3 mm (preferably between about 0.02 mm and 0.1 mm).

An end cap 440 is positioned at the ends of the fluid transfer tubes to provide fluid transfer from the inlet fluid transfer tubes to the outlet fluid transfer tubes. The endcap 440 is shown having an atraumatic tip. The endcap 440 may be any suitable element for providing fluid transfer from the inlet fluid transfer tubes to the outlet fluid transfer tubes. For example, endcap 440 may define an internal chamber, cavity, or passage serving to fluidly connect tubes 422,424.

With reference to FIG. 5B, an outer sheath 430 is shown surrounding the tube bundle 420. The outer sheath serves to hold the tubes in a tubular arrangement, and protect the construct from being penetrated or disrupted by foreign objects and obstacles.

A temperature sensor 432 is shown on the surface of the distal section. Temperature sensor may be a thermocouple to sense a temperature corresponding to the adjacent tissue, and sends the signal back through a wire in the tube bundle to the console for processing. Temperature sensor may be placed elsewhere along the shaft or within one or more of the fluid transport tubes to determine a temperature difference between inflow and outflow.

There are many configurations for tube arrangements. In embodiments the fluid transfer tubes are formed of a circular array, wherein the set of inlet fluid transfer tubes comprises at least one inlet fluid transfer tube 422 defining a central region of a circle and wherein the set of outlet fluid transfer tubes 424 comprises a plurality of outlet fluid transfer tubes spaced about the central region in a circular pattern. In the configuration shown in FIG. 5B, the fluid transfer tubes 422,424 fall within this class of embodiments.

During operation the cryogen fluid arrives at the catheter through a supply line from a suitable cryogen source at a temperature close to −200° C. The cryogen is circulated through the multi-tubular freezing zone provided by the exposed fluid transfer tubes, and returns to the connector.

In embodiments, the nitrogen flow does not form gaseous bubbles inside the small diameter tubes under any heat load, so as not to create a vapor lock that limits the flow and the cooling power. By operating at the near critical condition for at least an initial period of energy application, the vapor lock is eliminated as the distinction between the liquid and gaseous phases disappears.

A multi-tube design may be preferably to a single-tube design because the additional tubes can provide a substantial increase in the heat exchange area between the cryogen and tissue. Depending on the number of tubes used, cryoinstruments can increase the contact area several times over previous designs having similarly sized diameters with single shafts. However, the invention is not intended to be limited to a single or multi-tube design except where specifically recited in the appended claims.

Cryoablation Console

Figure 6:
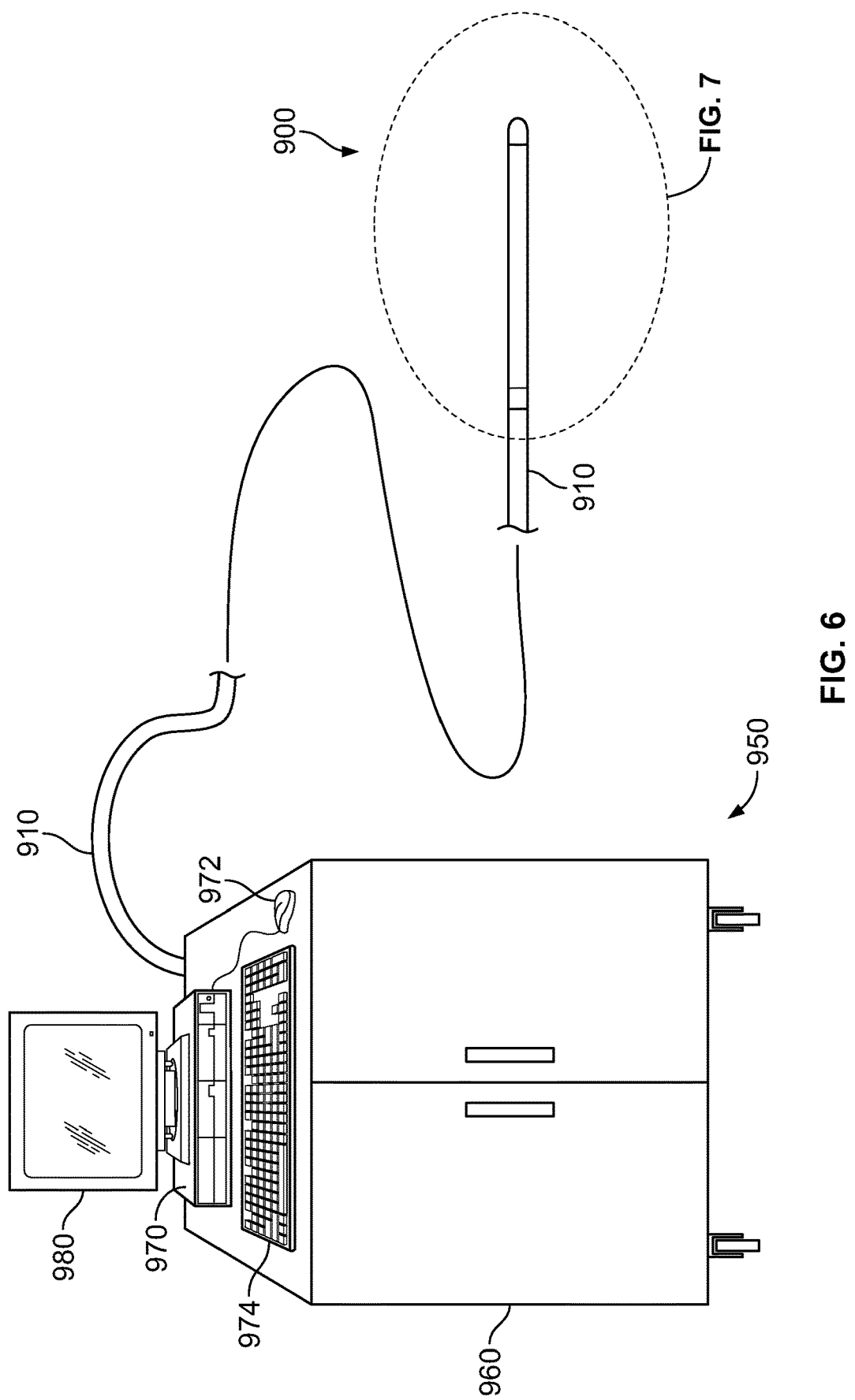
FIG. 6 is an illustration of a cryoablation system including a cryoablation catheter, according to an embodiment of the invention.

FIG. 6 illustrates a cryoablation system 950 having a cart or console 960 and a cryoablation catheter 900 detachably connected to the console via a flexible elongate tube 910. The cryoablation catheter 900, which shall be described in more detail below in connection with FIG. 7, contains one or more fluid transport tubes to remove heat from the tissue.

The console 960 may include or house a variety of components (not shown) such as, for example, a generator, controller, tank, valve, pump, etc. A computer 970 and display 980 are shown in FIG. 6 positioned on top of cart for convenient user operation. Computer may include a controller, timer, or communicate with an external controller to drive components of the cryoablation systems such as a pump, valve or generator. Input devices such as a mouse 972 and a keyboard 974 may be provided to allow the user to input data and control the cryoablation devices.

In embodiments computer 970 is configured or programmed to control cryogen flowrate, pressure, and temperatures as described herein. Target values and real time measurement may be sent to, and shown, on the display 980.

Figure 7:
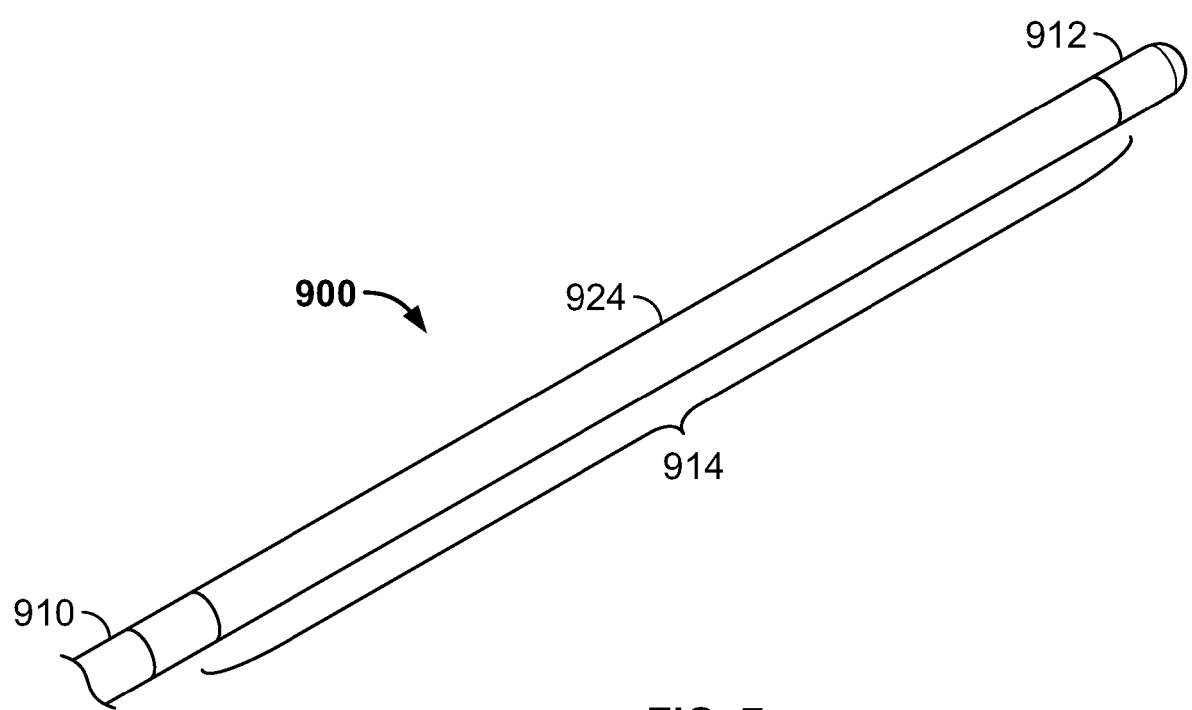
FIG. 7 is an enlarged perspective view of a distal section of the cryoablation catheter shown in FIG. 6.

FIG. 7 shows an enlarged view of distal section of cryoablation apparatus 900. The distal section 900 is similar to designs described above except that treatment region 914 includes a flexible protective cover 924. The cover serves to contain leaks of the cryogen in the event one of the fluid transport tubes is breached. Although a leak is not expected or anticipated in any of the fluid delivery transport tubes, the protective cover provides an extra or redundant barrier that the cryogen would have to penetrate in order to escape the catheter during a procedure. In embodiments the protective cover may be formed of metal.

Additionally, a thermally conducting liquid may be disposed within spaces or gaps between the transport tubes and the inner surface of the cover to enhance the device's thermal cooling efficiency during treatment. In embodiments the thermally conducting liquid is water.

Cover 924 is shown being tubular or cylindrically shaped and terminates at distal tip 912. As described herein, the cooling region 914 contains a plurality of fluid delivery and fluid return tubes to transport a cooling fluid through the treatment region 914 causing heat to be transferred/removed from the target tissue. In embodiments, the cryogen is transported through the tube bundle under physical conditions near the fluid's critical point in the phase diagram. The cover serves to, amongst other things, contain the cooling fluid and prevent it from escaping from the catheter in the event a leak forms in one of the delivery tubes.

Although a cover is shown in FIGS. 6-7, the invention is not intended to be so limited except as where recited in the appended claims. The apparatus may be provided with or without a protective cover and used to cool a target tissue.

Tube Within Tube

FIG. 8 shows a partial view of another cryoablation catheter 1010 having a protective means to mitigate leaks in the event a cooling fluid/cryogen escapes from the cryogen delivery tubes described above. In particular, catheter 1010 comprises a plurality or bundle 1012 of flexible multi-layer cryoenergy transfer tubes, each of which comprises two tubes in a coaxial arrangement, namely a tube within a tube.

Figure 9A:
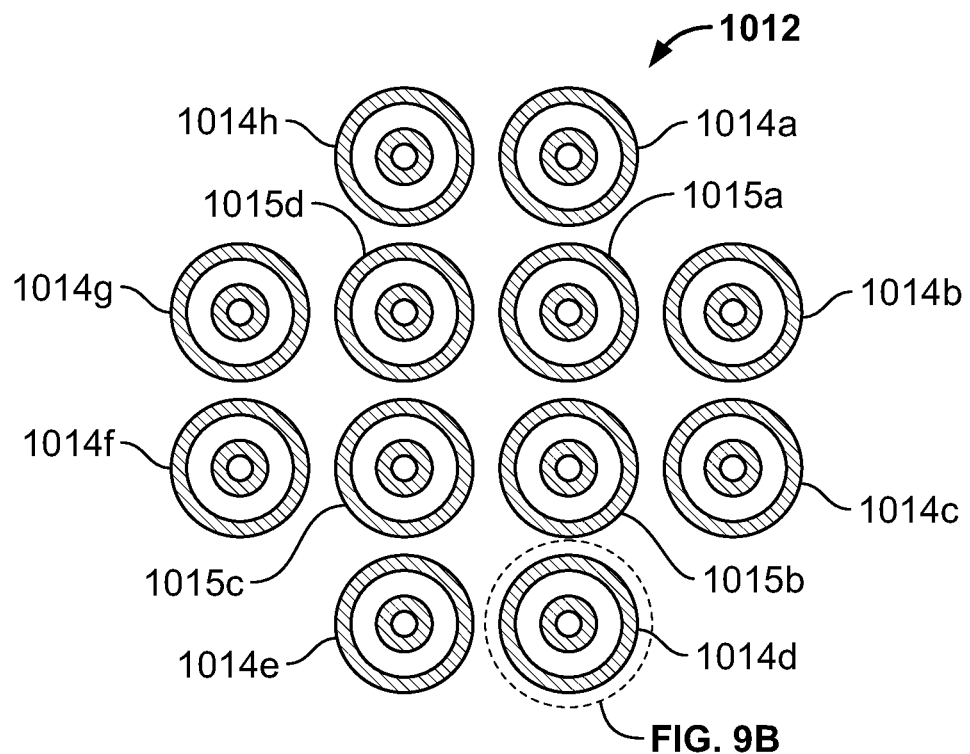
FIG. 9A is a cross-sectional view of an embodiment of a catheter shown in FIG. 8 taken along line 9A-9A in FIG. 9.

FIG. 9A shows a cross-sectional view taken along line 9A-9A of FIG. 8. The bundle of multilayer tubes 1012 is shown with the fluid delivery tubes 1014 and the fluid return tubes 1015 assembled in a parallel arrangement. The tube bundle 1012 is shown having 12 tubes/lines including four (4) fluid return tubes 1015a-1015d and eight (8) fluid delivery tubes 1014a-1014h. The fluid delivery tubes 1014a-1014h form a perimeter around the fluid return tubes 1015a-

1015d. This arrangement ensures that colder delivery fluid/cryogen is adjacent to the tissue to be ablated/frozen and warmer return fluid/cryogen is shielded from the tissue to be ablated/frozen.

Figure 9B:
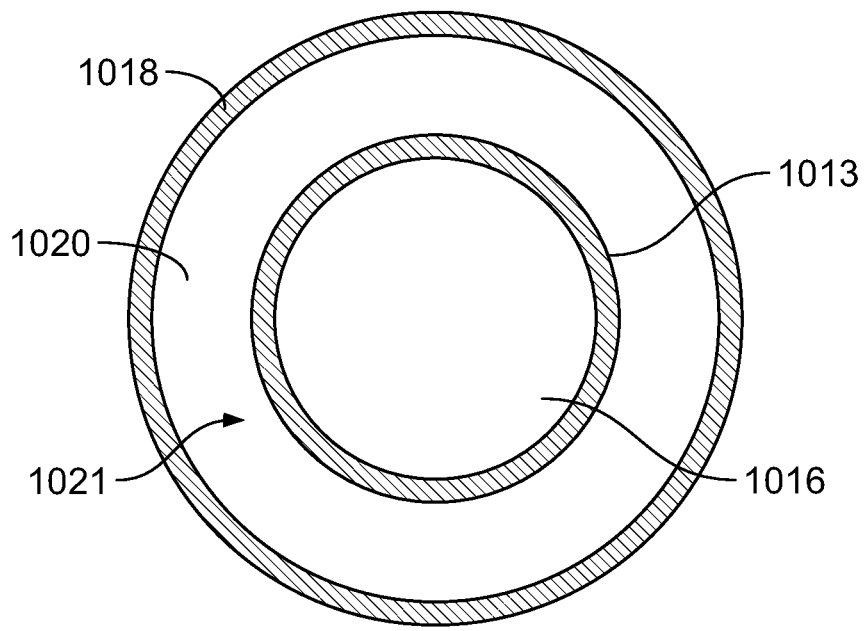
FIG. 9B is an enlarged view of one of the multi-layered tubes shown in FIG. 9A.

FIG. 9B shows an enlarged cross-sectional view of fluid delivery tube 1014d of FIG. 9A. The first or inner tube 1013 is shown coaxially surrounded by a second or outer tube 1018. A space or gap 1020 between the exterior surface of the inner tube 1013 and the interior surface of the outer tube 1018 is filled with a thermally conductive media 1021 as described herein. In embodiments, the gap 1020 has an annular shape. All of the fluid delivery tubes 1014 as well as the fluid return tubes 1015 can have a similar tube within a tube construction.

In the event of a leak of the cooling fluid 1016 or breach of the inner tube 1013, the cooling fluid 1016 is contained within the gap 1020 between the inner tube 1013 and the outer tube 1018. This tube within a tube feature adds an additional safety element to the device as any leaking fluid/cryogen 1016 is contained within the catheter and is prevented from entering the patient. In some embodiments, a pressure sensor/device or gauge may be incorporated to monitor the pressure of the thermally conductive media 1021 in the gap 1020. Therefore, if fluid/cryogen 1016 breaches the inner tube 1013 and leaks into the gap 1020, the pressure in the gap 1020 and hence, the conductive media 1021 will increase. Should a change in pressure occur above a threshold limit, the system can be programmed to halt ablation thereby preventing potential harm to a patient.

The inner tube 1013 may be fabricated and made from materials as described herein in connection with other flexible tubes for transporting the cooling fluid.

The outer tube 1018 material should also be flexible to enable elastic deflection of the distal treatment section to allow the distal treatment section to transform its shape as disclosed herein. In some embodiments, the outer tube is not inflatable, distensible nor expandable such that its size and shape remains substantially unaffected by the presence of the thermally conductive media 1021 contained therein. Non-limiting exemplary materials for the outer tube 1018 include polymers and metals or alloys. An example of an outer tube 1018 material is Nitinol or polyimide.

The number of tubes forming the tubular bundle 1012 may vary widely. In some embodiments, the tubular bundle 1012 includes 5-15 tubes, and more preferably, includes between 8-12 tubes comprising fluid delivery tubes 1014 and fluid return tubes 1015.

Figure 14:
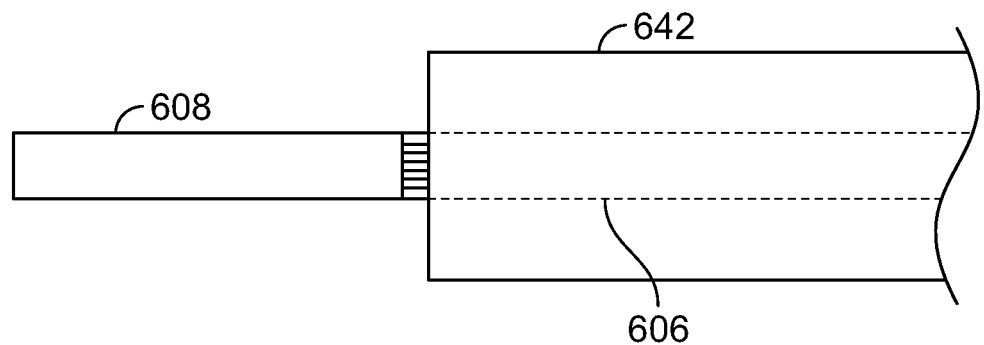
FIGS. 14-15 illustrate sequential deployment of the distal section of catheter shown in FIG. 11 from an outer sheath member.
Figures 16, 17:
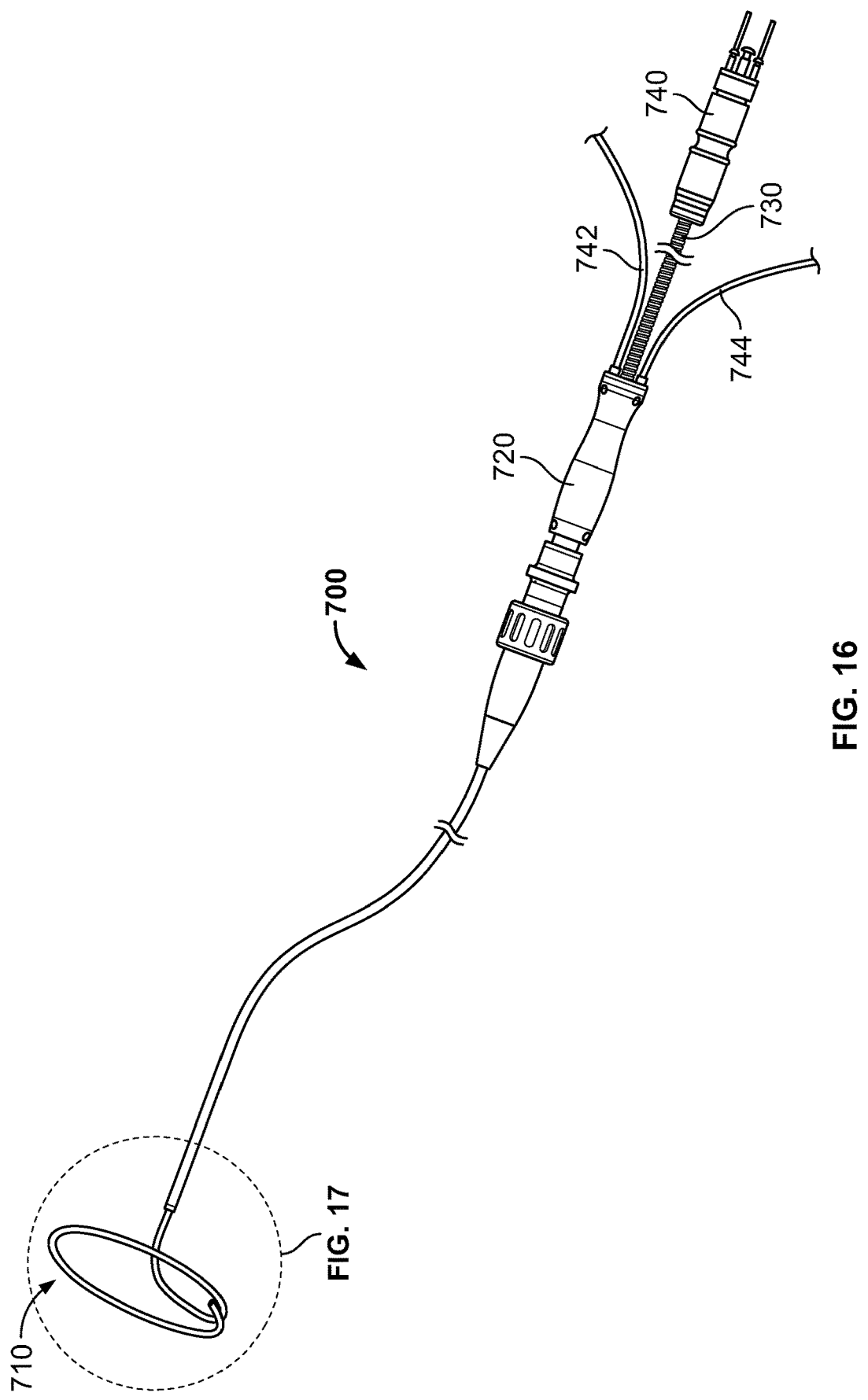
FIG. 16 is a perspective view of another embodiment of a cryoablation catheter having a flexible distal treatment section.
FIG. 17 is an enlarged view of the distal section of the catheter shown in FIG. 16.
Figure 17:
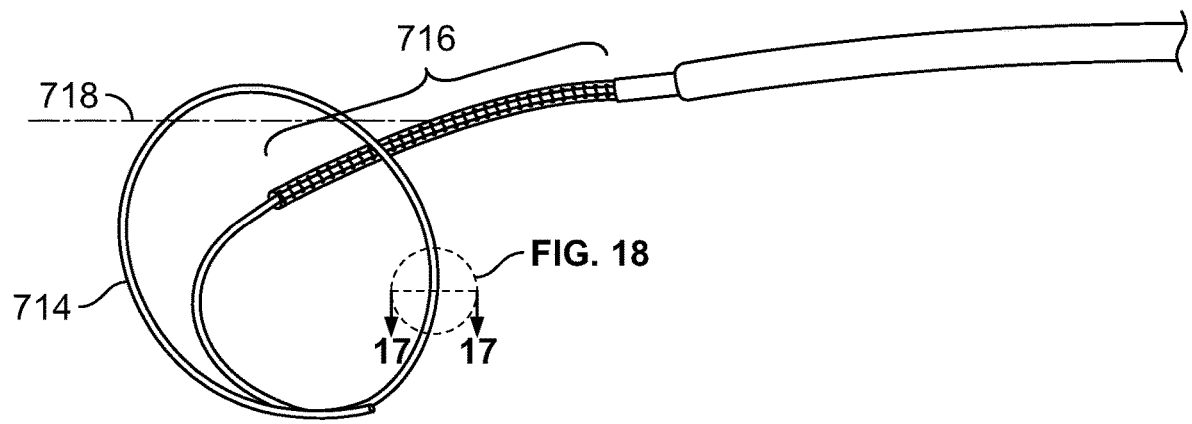

The cross-sectional profile of the tube bundle 1012 may also vary. Although FIG. 9A shows a substantially circular profile, in embodiments, the profile may be rectangular, square, cross or t-shaped, annular or circumferential, or another shape profile, including some of the arrangements described above. The tubes may also be braided, woven, twisted, or otherwise intertwined together, as depicted in FIGS. 9, 14 and 16 of commonly assigned U.S. patent application Ser. No. 14/915,632 entitled "ENDOVASCULAR NEAR CRITICAL FLUID BASED CRYOABLATION CATHETER AND RELATED METHODS," filed Sep. 22, 2014 by Alexei Babkin, et al., the entire contents of which are incorporated herein by reference for all purposes.

The diameter of the freezing section or tubular bundle may vary. In embodiments, the diameter of the bundle ranges from about 1-3 mm, and is preferably about 2 mm.

Figure 9C:
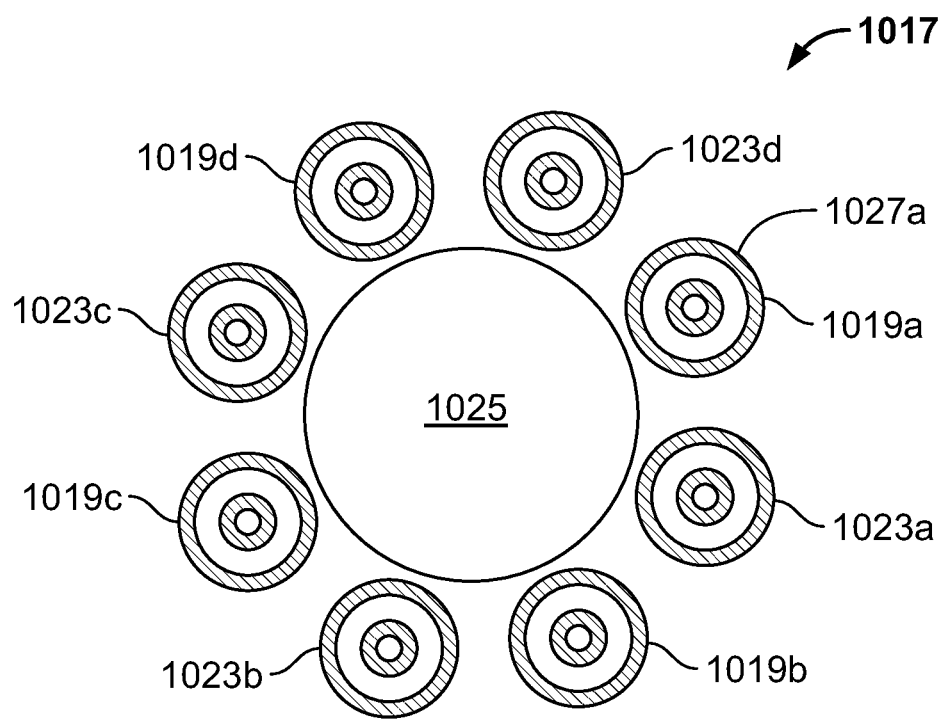
FIG. 9C is a cross sectional view of another embodiment of a cryoablation catheter.

FIG. 9C shows a cross-section of a cryoablation catheter having another tubular arrangement 1017. The eight (8) tubular elements (1019a-1019d and 1023a-1023d) are spaced or distributed circumferentially about a core element 1025. Preferably, as shown, fluid delivery elements/tubes (1019a-1019d) and fluid return elements/tubes (1023a-1023d) alternate along the circumference of the catheter.

Each inner tubular element (e.g., 1019a) includes an outer tubular element (e.g., 1027a) coaxially surrounding the inner tubular element thereby creating a space or gap which can be filled with a thermally conductive media/fluid as described with respect to FIG. 9B.

Steering elements, sensors and other functional elements may be incorporated into the catheter. In embodiments, steering elements are incorporated into a mechanical core such as the mechanical core 1025 shown in FIG. 9C.

Figure 10A:
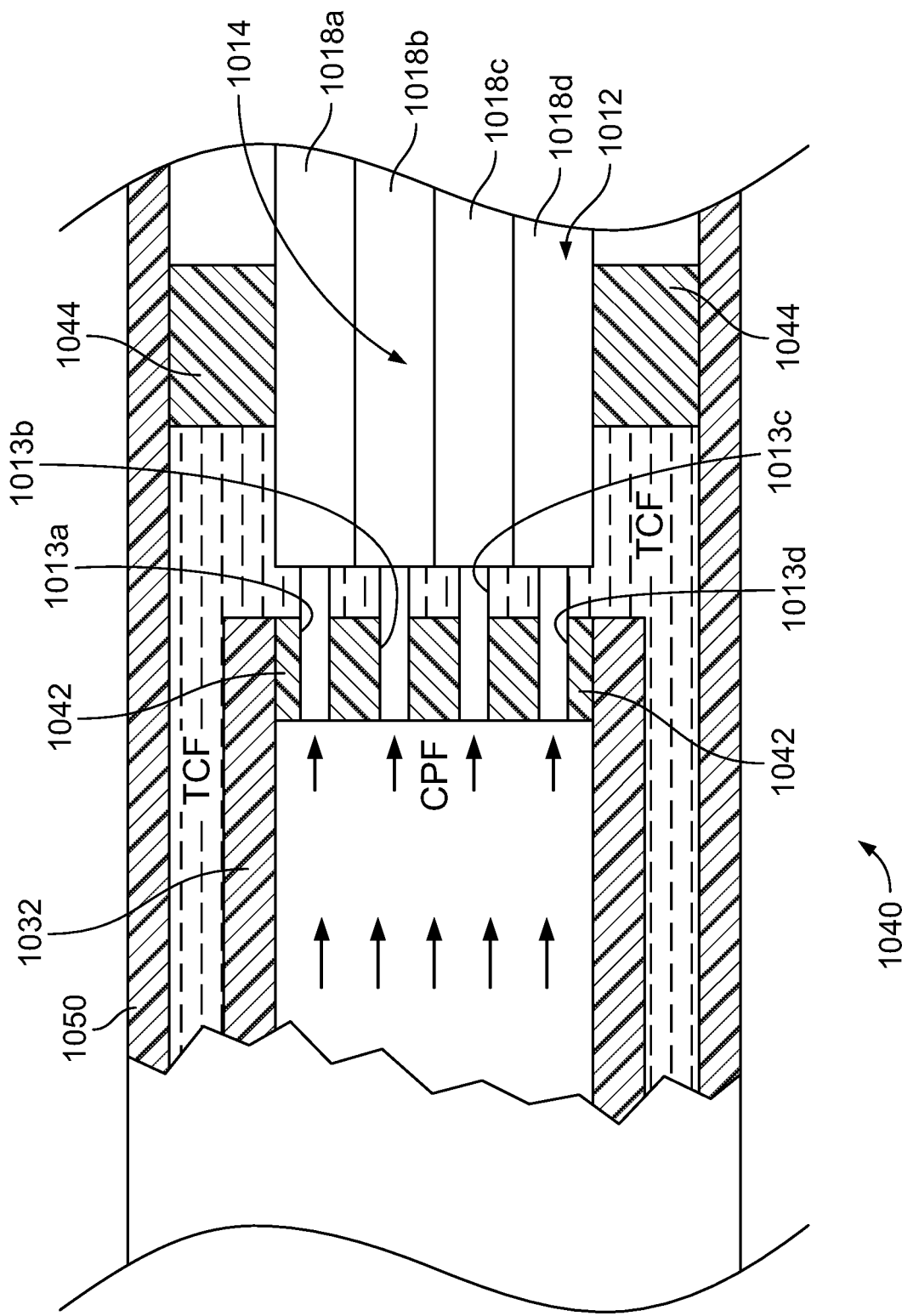
FIG. 10A is a partial sectional view of an embodiment of a catheter shown in FIG. 8.

FIG. 10A shows an enlarged cut-away view of the catheter at detail 10A in FIG. 8, illustrating tube bundle 1012 fluidly connected to the end portion 1040 of an intermediate section of the catheter 1010.

Figure 10B:
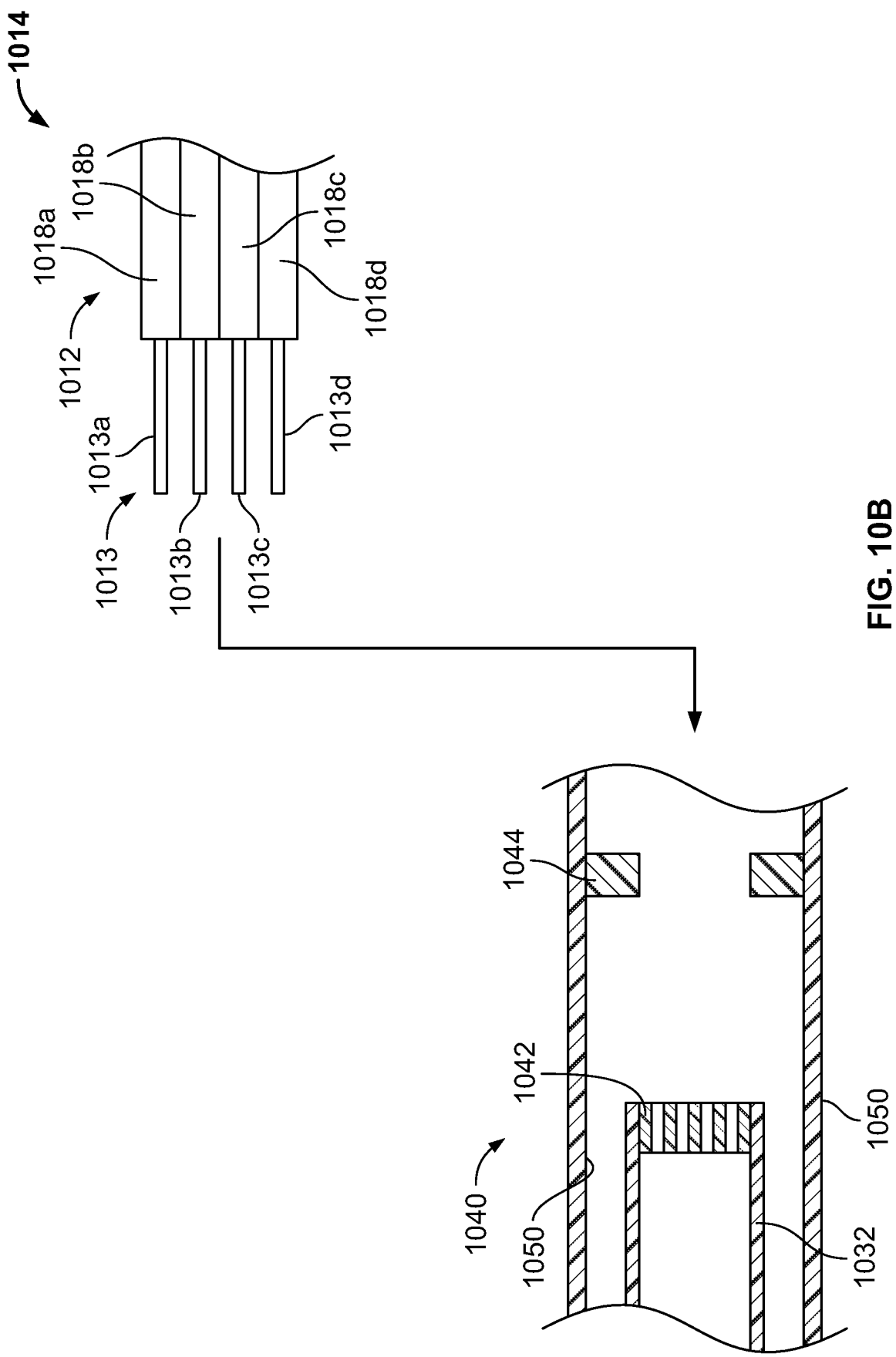
FIG. 10B is a partial exploded view of the proximal ends of the tube elements and the distal end of the intermediate section of an embodiment of a catheter shown in FIG. 8.

FIG. 10B shows an exploded view of a proximal section of the tube bundle 1012 and the intermediate section of catheter 1040. Tube bundle 1012, having inner tubular elements 1013a-1013d extending beyond outer tubular elements/covers 1018a-1018d of fluid delivery lines 1014, can be inserted into intermediate section of catheter 1040.

With reference to FIGS. 10A-10B, fluid delivery lines 1014 are shown bundled together and inserted/joined to main line 1032. An adhesive plug 1042 or seal, gasket, or stopper, etc. may be applied to facilitate and ensure a fluid seal between the tube members. The cooling power fluid (CPF) is transported to the fluid delivery lines 1014 from the fluid delivery main line 1032.

The proximal ends of outer tubular elements/covers 1018a-d, which are offset from proximal ends of inner tubular elements 1013a-d, are shown inserted into intermediate section 1040 of catheter such that the thermally conductive fluid (TCF) within lumen 1050 can fill gaps 1020 (FIG. 9B) of each of the multi-layer cryoenergy tubular elements. An adhesive plug 1044 (weld or bond) may be applied to facilitate a fluid tight and robust connection. Press fits, heat, and other fabrication techniques can be applied to join components as is known to those of skill in the art.

FIG. 11 shows another cryoablation catheter 500 including a distal treatment section 510, a handle 520, and an umbilical cord 530. The proximal end of the umbilical cord 530 terminates in connector 540, which is inserted into receptacle port 560 on console 550.

One or more ancillary connector lines 570 are shown extending proximally from the handle 520. The tubular lines 570 may serve to provide various functionality including without limitation (a) flushing; (b) vacuum; (c) thermally conductive liquid described above; and/or (d) temperature and pressure sensor conductors.

The catheter 500 is also shown having electrical connector 580 extending proximally from the handle 520. Electrical connector 580 may be coupled to an EP recording system for analyzing electrical information detected in the distal treatment section 510. Examples of systems for analyzing the electrical activity include, without limitation, the GE Healthcare CardioLab II EP Recording System, manufactured by GE Healthcare, USA and the LabSystem PRO EP Recording System manufactured by Boston Scientific Inc. (Marlborough, MA). The recorded electrical activity may also be used to evaluate or verify the continuous contact with the target tissue as described in commonly assigned International Patent Application No. PCT/US16/51954, entitled "TISSUE CONTACT VERIFICATION SYSTEM", filed Sep. 15, 2016 by Alexei Babkin, et al., the entire contents of which are incorporated herein by reference for all purposes.

Figure 12:
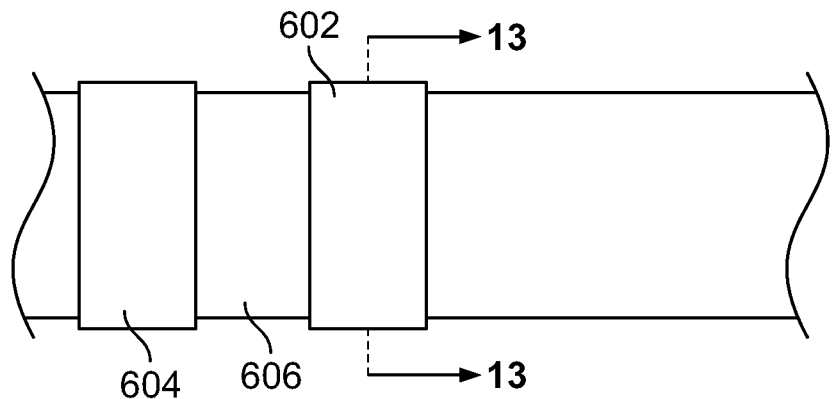
FIG. 12 is an enlarged view of a portion of the distal section shown in FIG. 11.

FIG. 12 shows an enlarged view of a portion of the distal section 510 of the catheter 500. Ring-shaped electrodes 602, 604 are circumferentially disposed about shaft 606. Although two electrodes are shown, more or less electrodes may be present on the shaft for sensing electrical activity. In embodiments, up to 12 electrodes are provided on the shaft. In one embodiment, 8 electrodes are axially spaced along the shaft 606.

Figure 13:
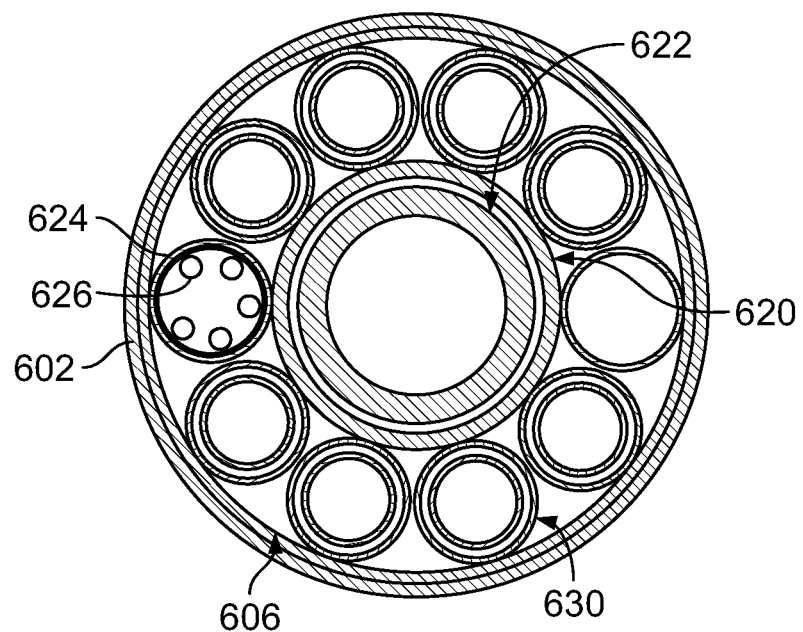
FIG. 13 is a cross sectional view of the catheter shown in FIG. 12 taken along line 13-13 in FIG. 12.

FIG. 13 is a cross section of the catheter shown in FIG. 12 taken along line 13-13. The catheter shaft is shown having a mechanical core 620 extending along the central axis, and a plurality of energy delivering tube constructs 630 extending parallel and circumferentially disposed about the mechanical core.

Each tube construct 630 is shown having dual layers as described above in connection with FIGS. 8-9 and a thermally conductive liquid layer disposed there between.

A tubular line 624 is shown for housing conducting wires 626 for the various sensors described herein.

The mechanical core 620 may be constructed to provide a preset shape to the catheter distal treatment section. With reference to FIG. 13, the mechanical core includes a metal tubular member 622 having a preset shape. The preset shape matches the target anatomy to make continuous contact with the target anatomy. An exemplary material for the preset tubular element 622 is Nitinol. FIG. 13 also shows an exterior layer or cover concentrically surrounding the Nitinol tube. The exterior cover may be a flexible polymer such as, for example, PET. Collectively, the inner PET layer 620 and outer shaft layer 606 form a fluidly-sealed annular chamber to house the plurality of tubular constructs 630.

Figure 15:
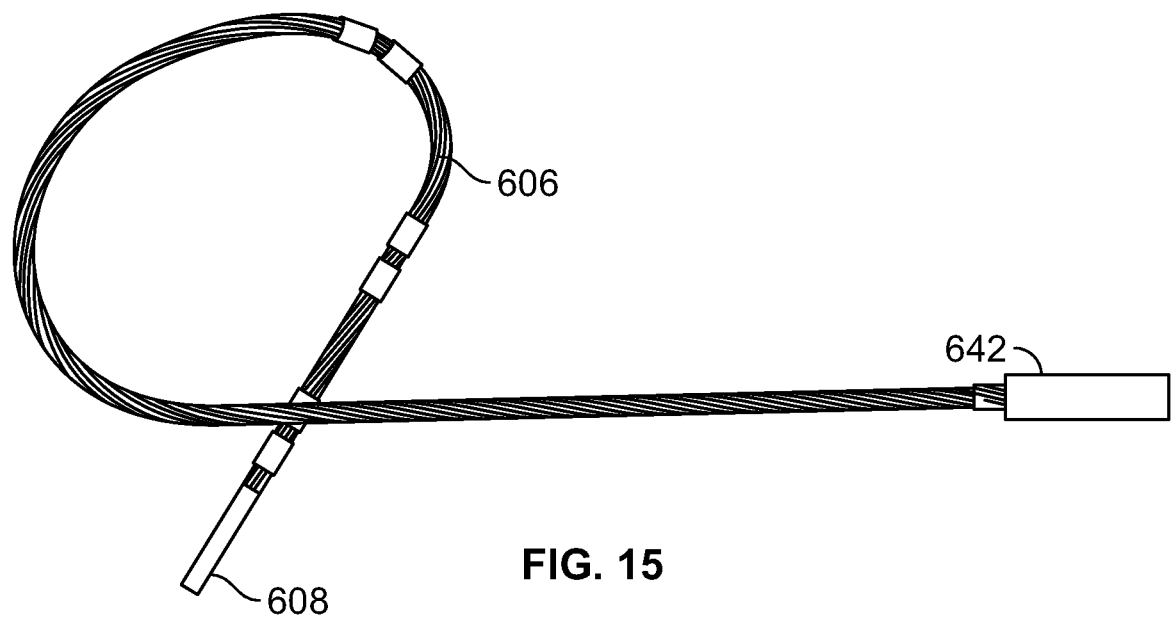

With reference to FIGS. 14-15, a catheter 606 is shown being deployed from an outer sheath 642. Initially, catheter distal section 606 is disposed within a lumen of external sheath 642, and prohibited from assuming its preset shape. The distal section 606 and external sheath 642 are moved axially relative to one another. For example, the catheter may be ejected from the sheath. Once the catheter is free from constraint, it assumes the preset shape as shown in FIG. 15.

Mechanical core assembly biases the shape of the catheter distal section 606, forcing the energy delivering elements into a curvilinear shape. In embodiments, the catheter shape is adapted to create lesions in the right atrium useful in treating atrial flutter. The shape shown in FIG. 15, for example, is a single loop or elliptical shape which has curvature to match target zones of tissue in the right atrium useful in treating atrial flutter. Additional apparatus and methods for treating atrial flutter are described in commonly assigned U.S. Patent Application No. 61/981,110, filed Apr. 17, 2014, now International Patent Application No. PCT/US2015/024778, filed Oct. 21, 2015 entitled "ENDOVASCULAR NEAR CRITICAL FLUID BASED CRYOABLATION CATHETER HAVING PLURALITY OF PREFORMED TREATMENT SHAPES," the contents of both of which are incorporated herein by reference in their entireties for all purposes.

FIG. 16 shows another cryoablation catheter 700 including a distal treatment section 710, a handle 720, and an umbilical cord 730 which terminates in connector 740. Similar to the system described above in connection with FIG. 11, connector 740 may be inserted into a receptacle port on a console.

Additional lines 742, 744 are shown extending proximally from handle. Lines 742, 744 provide various functionalities to the distal treatment section 710 during a procedure. Example functionalities include, without limitation, temperature, EP recording, pressure, fluid flush, source liquids, etc.

FIG. 17 is an enlarged view of the catheter distal section following deployment. The treatment section is shown having a generally looped or elliptical shape 714. An intermediate section 716 is shown providing a bend or articulation from central axis 718. Such functionality aids in positioning the treatment section in continuous direct contact with the tissue. In embodiments, the shape is configured to create complete PVI in the left atrium.

Figure 18:
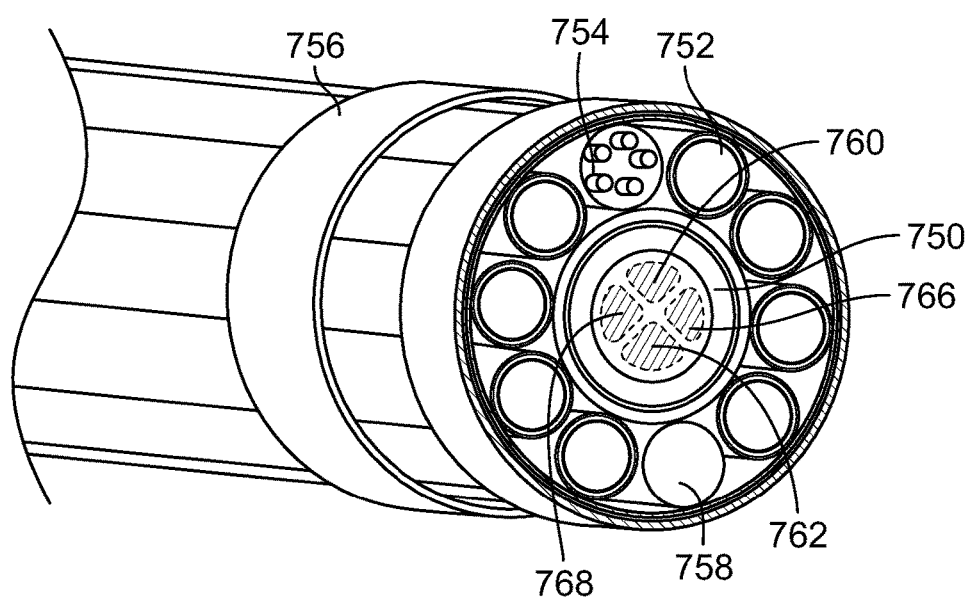
FIG. 18 is a cross sectional view of the catheter shown in FIG. 17 taken along line 17-17 in FIG. 17.

FIG. 18 is an enlarged cross sectional view of a portion of the distal treatment section. The catheter shaft is shown having a mechanical core 750 extending along the central axis, and a plurality of energy delivering tube constructs 752 extending parallel and circumferentially about the mechanical core. One or more spare tubular elements 754,758 can be incorporated into the perimeter space in combination with energy delivery elements. Tubular element 754 holds a plurality of electrical conductors to transmit electrical activity from sensors or ring electrodes 756 present on the distal treatment section. Tubular element 758 may provide vacuum or liquid to the catheter for various functions described herein.

Mechanical core 750 is shown extending axially through the treatment section and comprising a plurality of members 760, 762 which extend through the distal treatment section to bias the distal section into a preset shape such as the loop shape shown in FIG. 17. In particular, in embodiments, the mechanical core can include a biased shape element 760 such as a Nitinol wire, and an axially movable control member 762 connected to a distal tip of the treatment section to adjust the curvature of the preset shape. Core may include additional lumens 766,768 if desired. The mechanical core acts to shape the distal treatment section to a first preset loop shape, and can be further adjusted by the control member to make continuous contact with a target tissue surface.

FIGS. 19A-19D illustrate sequentially deployment of an ablation catheter 810 from a first arcuate shape having a slight bend to a second configuration having a complete ring or circular shape 820. The shape is assumed once the catheter treatment section is not constrained by the outer sheath 812.

Figure 19A:
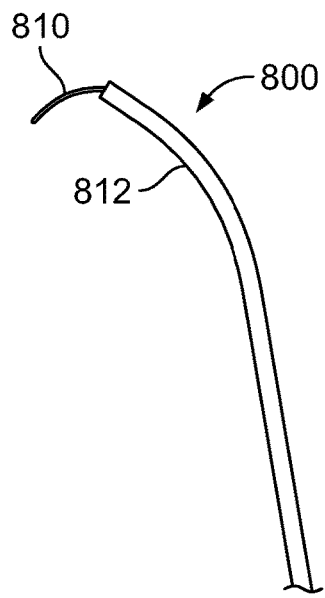
FIGS. 19A-19D show deployment of a distal section of the catheter, according to an embodiment of the invention.
Figure 19B:
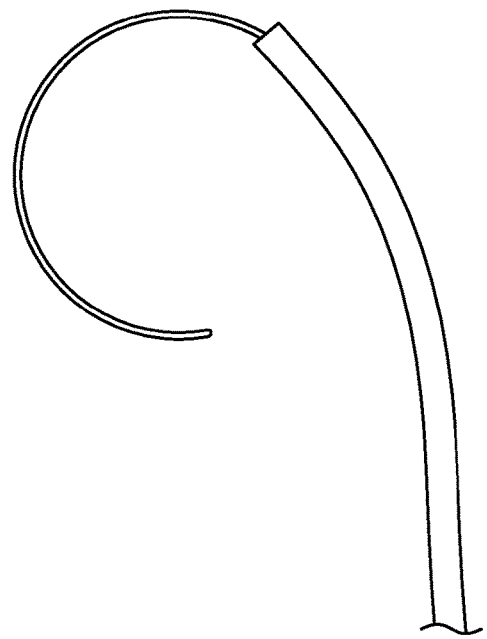
Figure 19C:
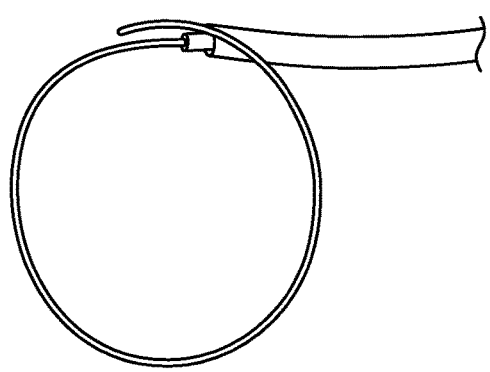
Figure 19D:
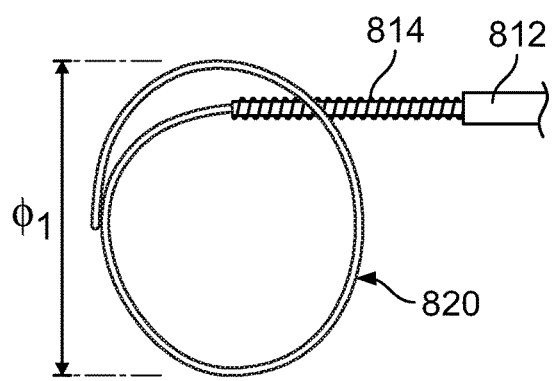
Figure 20A:
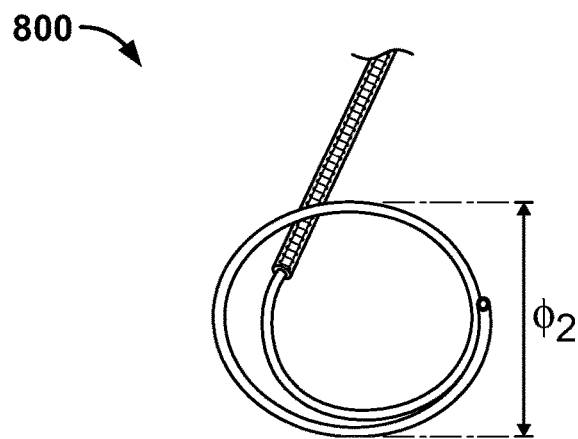
FIGS. 20A-20B show reducing the diameter of the preset loop shape of the catheter shown in FIG. 19D.
Figure 20B:
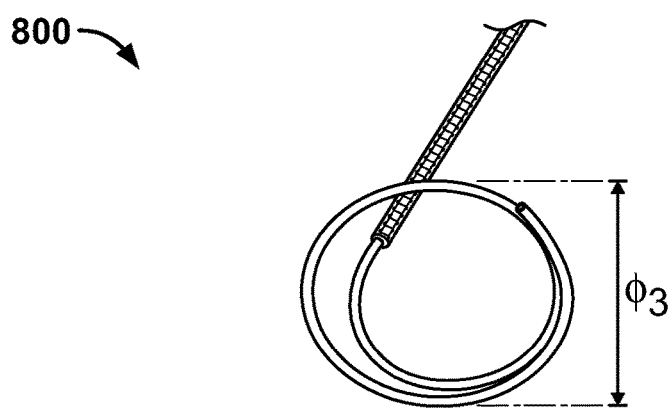

FIGS. 20A-20B show an enlarged view of the catheter 800 of FIG. 19D except that the loop has been adjusted by reducing its diameter $\Phi_1$. As described herein, a control member extending through the shaft of the distal treatment section is pulled to reduce the diameter of the preset loop $\Phi_1$ to diameter $\Phi_2$ as shown in FIG. 20A. FIG. 20B shows the loop adjusted to an even smaller diameter $\Phi_3$ than that shown in FIG. 20A.

The diameter $\Phi$ of the loop may vary. In embodiments, the diameter of the loop is controlled to range from 2 cm to 5 cm, and in embodiments, preferably about 2-3 cm.

Figure 21A:
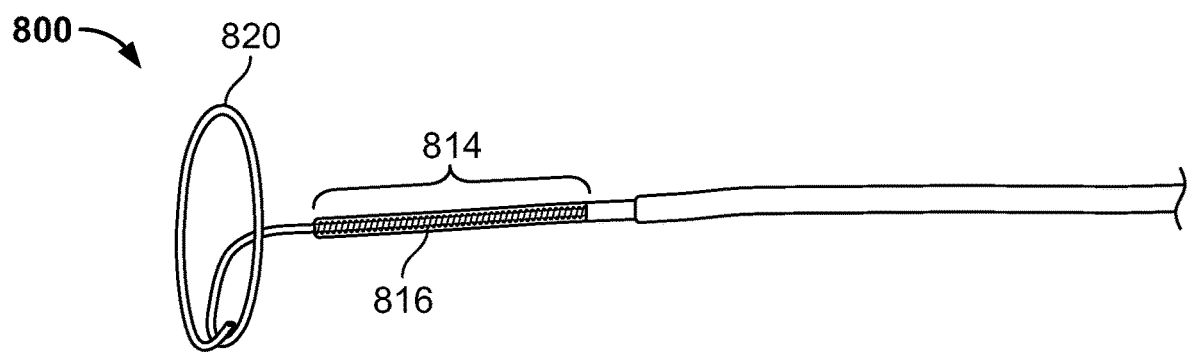
FIGS. 21A-21C show articulation of a catheter shaft, according to an embodiment of the invention.
Figure 21B:
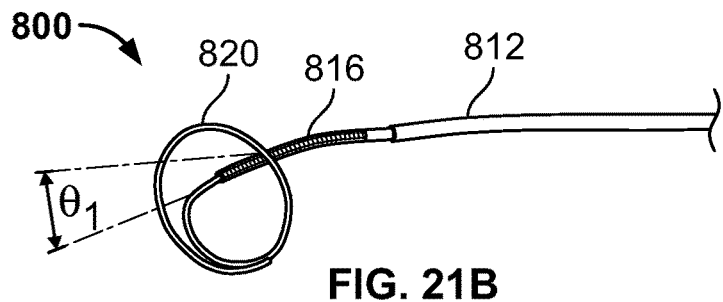
Figure 21C:
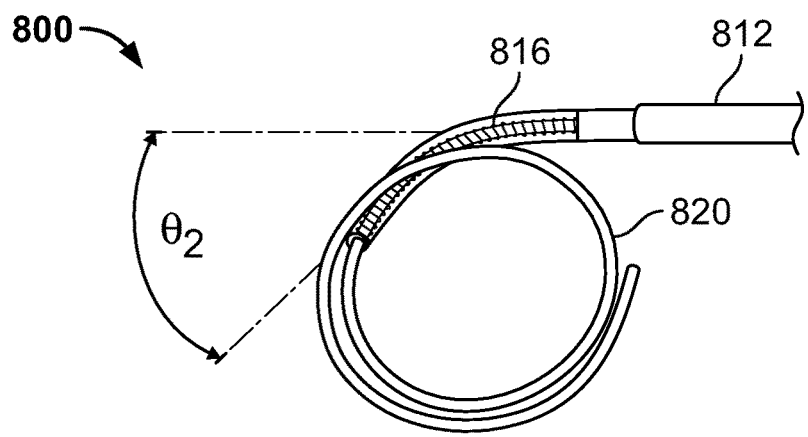

FIGS. 21A-21C show sequentially articulation of the intermediate section 814 of the catheter. The intermediate section 814 is shown having an outer support or reinforcing structure 816. In embodiments, the support layer 816 is a spring or coil.

FIG. 21A shows catheter intermediate section 814 substantially straight or aligned with the shaft axis.

FIG. 21B shows catheter intermediate section having a slight articulation forming angle $\theta_1$ with shaft axis.

FIG. 21C shows catheter intermediate section having further articulation $\theta_2$ with shaft axis. The degree of articulation may vary and be adjusted by the physician as described below. In embodiments, the degree of articulation is up to 120 degrees from the central shaft axis, and more preferably up to about 90 degrees.

Figure 22A:
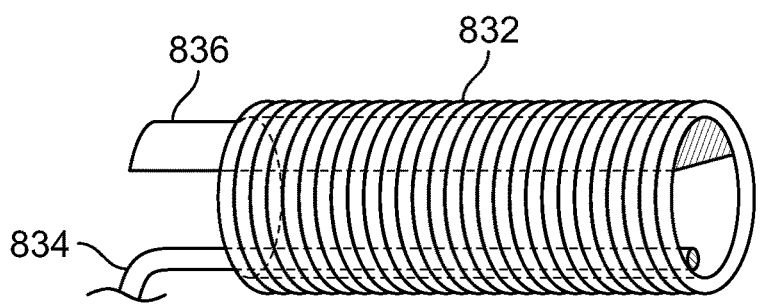
FIGS. 22A-22B show components of an intermediate section of the catheter.
Figure 22B:
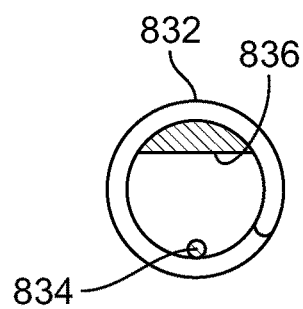

FIGS. 22A-22B show examples of components/structures for articulating the intermediate section. The components include a coil 832, second pull wire 834, and spine 836. The pull wire 834 is fixed to a distal location of the intermediate section. Pulling on the pull wire results in deflecting or articulating the coil 832. Spine 836 is shown diametrically opposite the pull wire. The spine serves to bias the direction that the catheter bends when the pull wire is retracted and serves to return the catheter to its straightened position when the pull wire is released. In particular, when the pull wire is retracted, the catheter bends towards the pull wire along a plane including the pull wire, central coil axis, and the spine.

The various articulating components/structures may be made of a wide variety of materials. Exemplary materials include without limitation Nitinol, stainless steel, or other materials having the functionality described herein. Additionally, the components may be fabricated from wire, tubular elements, or sheets of stock material. In one embodiment, the coil and spring are integrally formed from a sheet of metal alloy. The desired shape may be machined or laser cut to create the spine and rib elements, allowing for biased articulation. See also US Patent Publication No. 2003/0195605, filed May 30, 2003, entitled "Cryogenic Catheter with Deflectable Tip" to Kovalcheck et al. for further details describing catheters comprising a spring, pull wire and spine for controlling deflection.

Figure 23A:
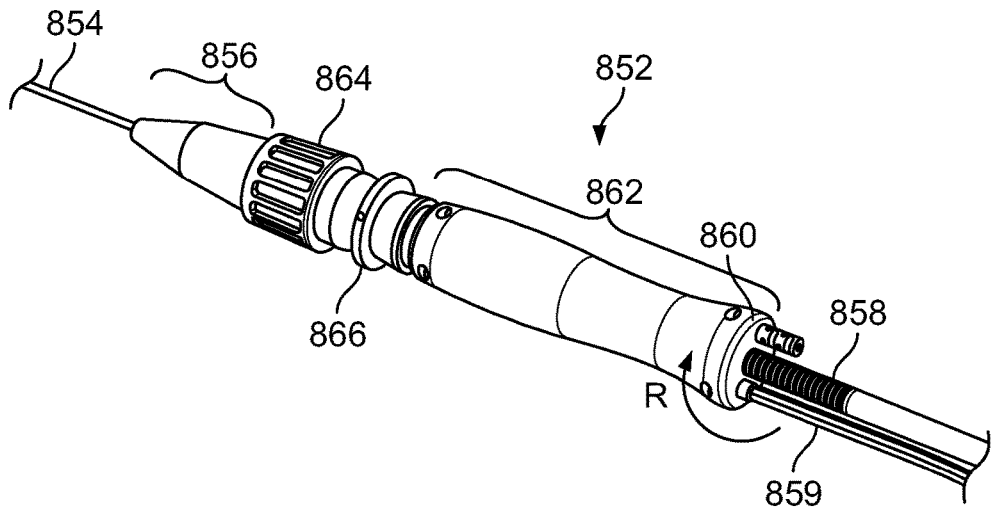
FIG. 23A shows a perspective view of a handle for an ablation catheter, according to an embodiment of the invention.

FIG. 23A shows a perspective view of a handle 852 of an ablation catheter. A flexible catheter shaft 854 extends from a distal section 856 of the handle. Umbilical cord 858 and various other functional lines and connectors 859 are shown extending proximally from a proximal section 860 of handle.

Handle 852 is shown having an ergonomic design including a smooth gently curved intermediate section 862 that allows a user to conveniently hold the handle.

Handle is shown comprising a knob 864 which may be rotated relative to the handle body to control the diameter of the deployed loop as described above. An axially movable hub 866 is shown proximal to the knob. Movement of the hub 866 forward or backwards serves to adjust or articulate the deployed shaft as described above. Additionally, handle may be rotated as a whole to steer the catheter in one direction or another. Collectively, the handle provides a convenient and semi automatic apparatus to turn, articulate, and control the diameter or size of the deployed structure.

Figure 23B:
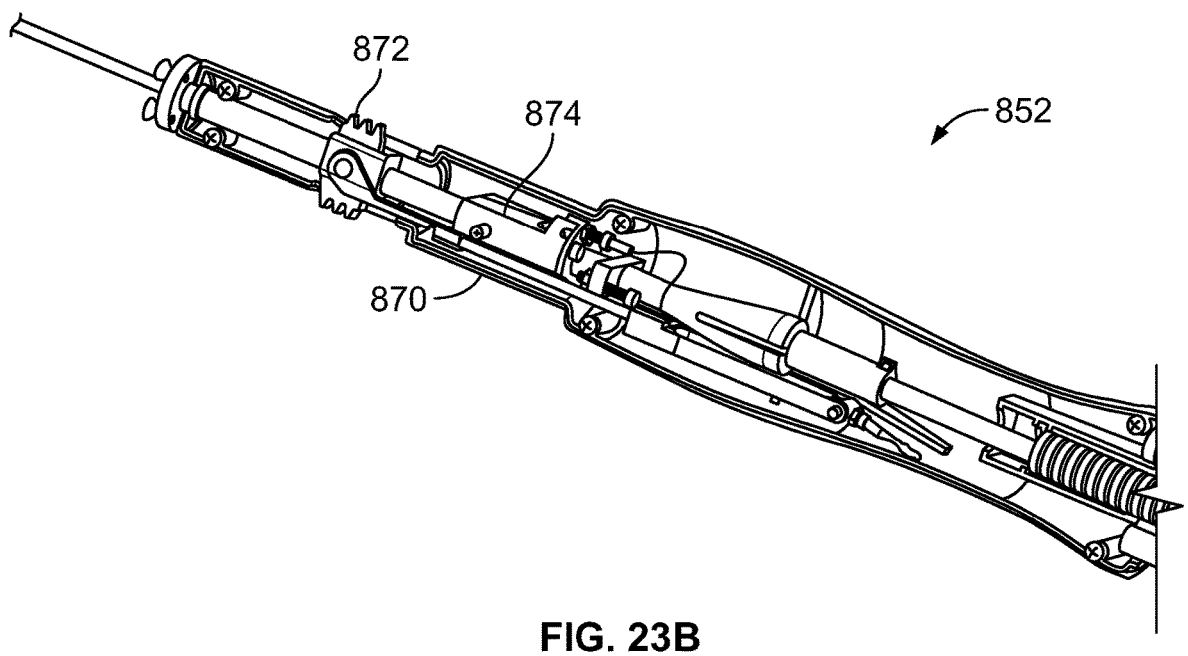
FIG. 23B shows a partial perspective view of the handle shown in FIG. 23A with the exterior removed.

FIG. 23B shows a partial perspective view of the handle shown in FIG. 23A with the exterior removed for clarity. A segment of an external thread or teeth 872 are shown. The teeth 872 mate with grooves or thread in the knob 864. The teeth are linked to a first control member described above for changing the shape or diameter of the loop. As the knob is rotated, the pull wire is moved simultaneously.

Slider 874 is also shown in handle. Slider 874 is joined to hub 866 such that movement of the hub causes the slider to move. Slider is also linked to a second control member as described above for articulating the catheter shaft. When the exterior hub is moved by the physician, the second control member articulates the shaft.

Although the handle is shown having a knob, hub, and slider, the invention is not intended to be so limited. The invention can include other levers, gears, buttons, and means for causing the above described functionality.

Applications

The cryoablation apparatus described herein has a wide range of diagnostic and therapeutic applications including, for example, endovascular-based cardiac ablation and more particularly, the endovascular-based cardiac ablation treatment of atrial fibrillation.

Figure 24:
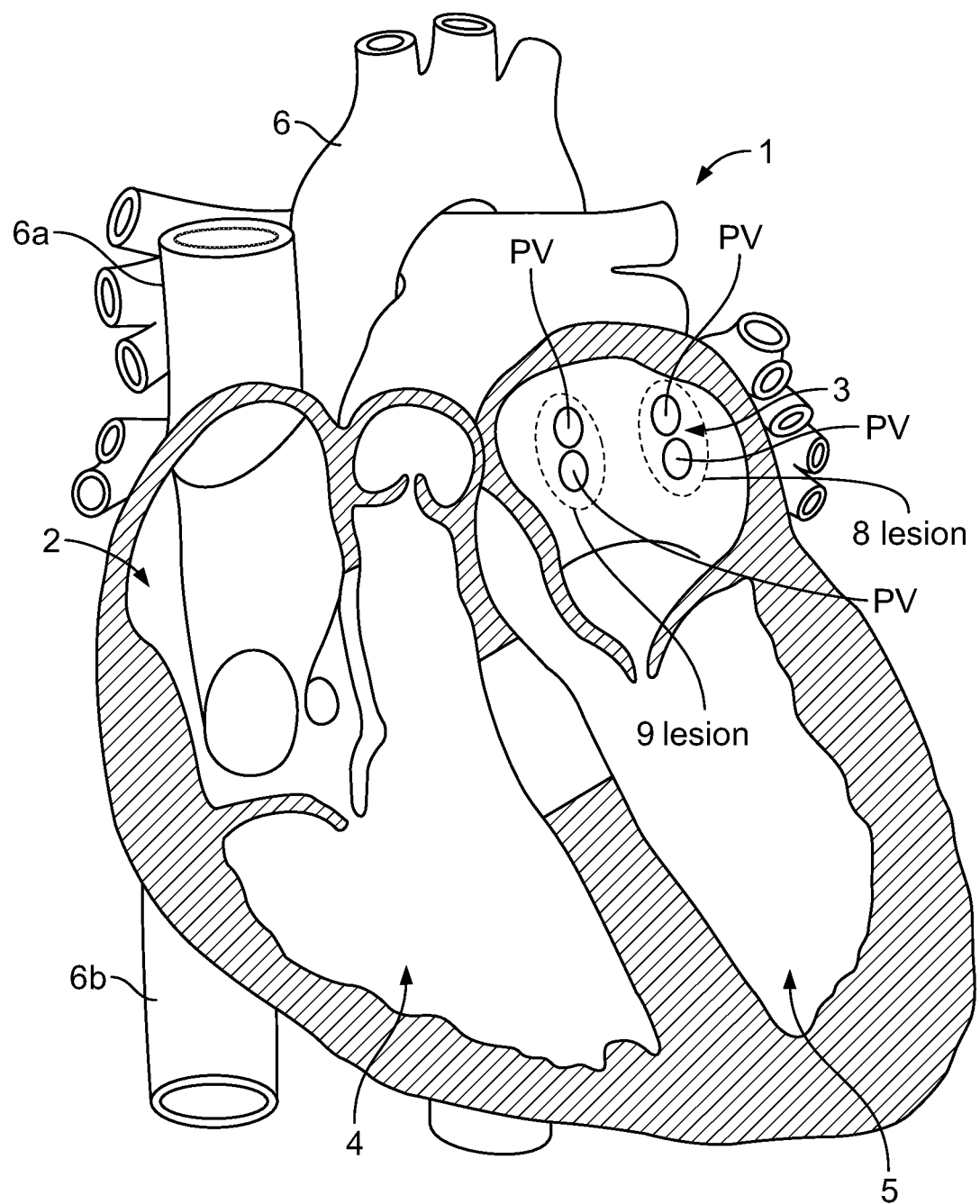
FIG. 24 is an illustration of a heart, and locations of various lesions according to an embodiment of the invention.

FIG. 24 shows examples of target ablation lesions in a pulmonary vein isolation (PVI) procedure for the treatment of atrial fibrillation.

The basic structures of the heart 1 are shown in FIG. 24 including the right atrium 2, the left atrium 3, the right ventricle 4 and the left ventricle 5. The vessels include the aorta 6 (accessed through the femoral artery), the superior vena cava 6a (accessed through the subclavian veins) and the inferior vena cava 6b (accessed through the femoral vein).

Exemplary target lesions for a PVI procedure include lesion 8 which surrounds and isolates all left pulmonary veins (PVs), and lesion 9 which surrounds and isolates all right pulmonary veins (PVs). As described further herein, the invention may include application or creation of additional lesions to increase the effectiveness of the treatment. Also, it is to be understood that although the following discussion primarily focuses on embodiments for performing PVI, the technology and procedure described herein for producing these lesions can be used to create other lesions in an around the heart and other organs such as that described in international patent application nos. PCT/US2012/047484 to Cox et al. and PCT/US2012/047487 to Cox et al. corresponding to International Publication Nos. WO2013/013098 and WO2013/013099 respectively, the contents of each of which is hereby incorporated by reference in their entirety.

Figure 25:
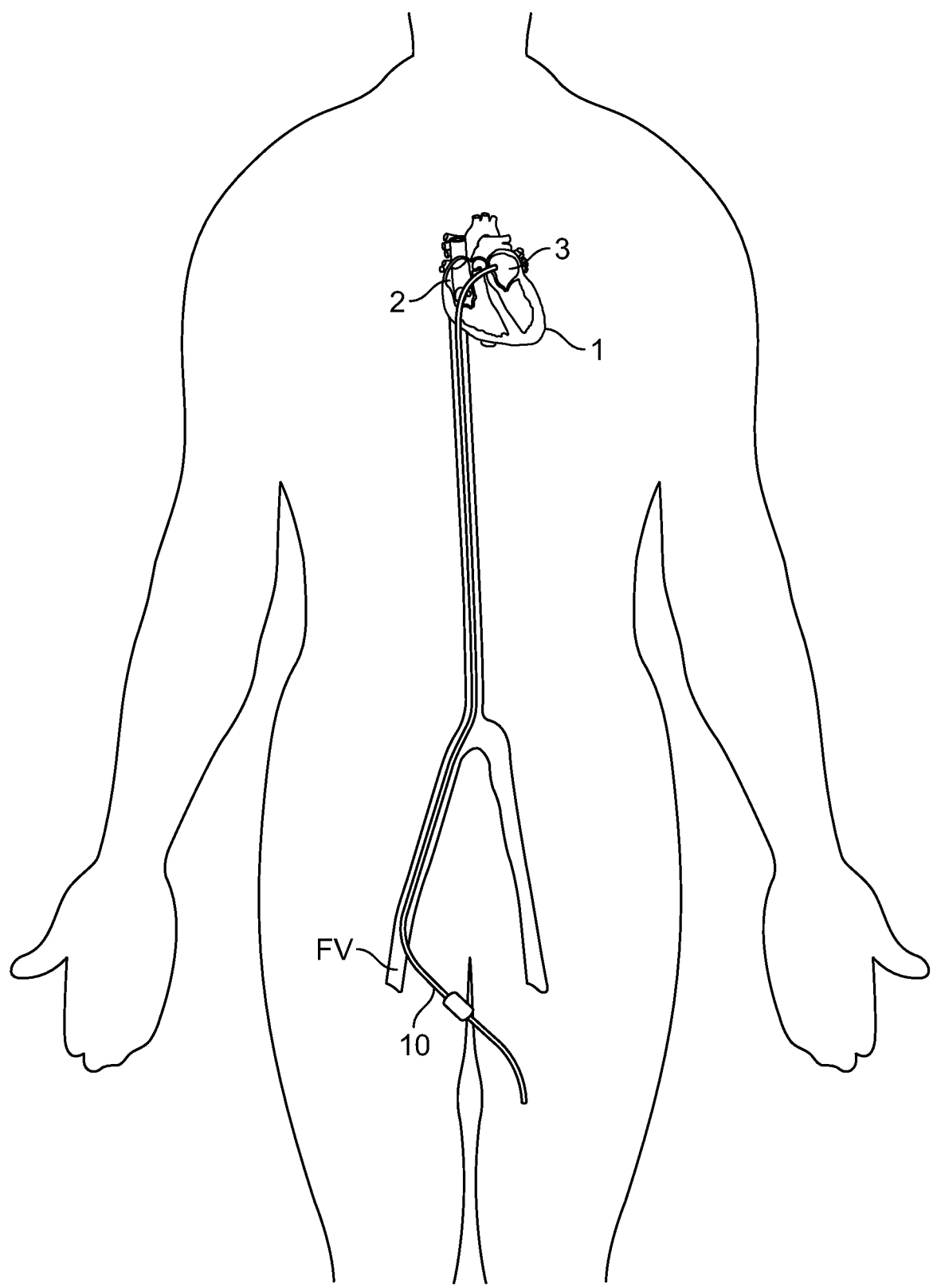
FIG. 25 is an illustration of an embodiment of endovascular catheterization to access the heart.

FIG. 25 illustrates one technique to reach the left atrium with the distal treatment section of a catheter. The procedure may be performed under conscious sedation, or general anesthetic if desired.

A peripheral vein (such as the femoral vein FV) is punctured with a needle. The puncture wound is dilated with a dilator to a size sufficient to accommodate an introducer sheath, and an introducer sheath with at least one hemostatic valve is seated within the dilated puncture wound while maintaining relative hemostasis.

With the introducer sheath in place, the guiding catheter 10 or sheath is introduced through the hemostatic valve of the introducer sheath and is advanced along the peripheral vein, into the target heart region (e.g., the vena cavae, and into the right atrium 2). Fluoroscopic imaging can be used to guide the catheter to the selected site.

Once in the right atrium 2, the distal tip of the guiding catheter is positioned against the fossa ovalis in the intraatrial septal wall. A needle or trocar is then advanced distally through the guide catheter until it punctures the fossa ovalis. A separate dilator may also be advanced with the needle through the fossa ovalis to prepare an access port through the septum for seating the guiding catheter. The guiding catheter thereafter replaces the needle across the septum and is seated in the left atrium through the fossa ovalis, thereby providing access for devices through its own inner lumen and into the left atrium.

Placement of the above tools may be carried out with guidance from one or more of the following: fluoroscopy, intracardiac pressures, transesophageal echocardiography (TEE), and intracardiac echocardiography (ICE).

FIGS. 26-29 illustrate a method for deploying a ring-shaped catheter in the left atrium and around pulmonary vein entries for treating various heart conditions such as atrial fibrillation.

Figure 26:
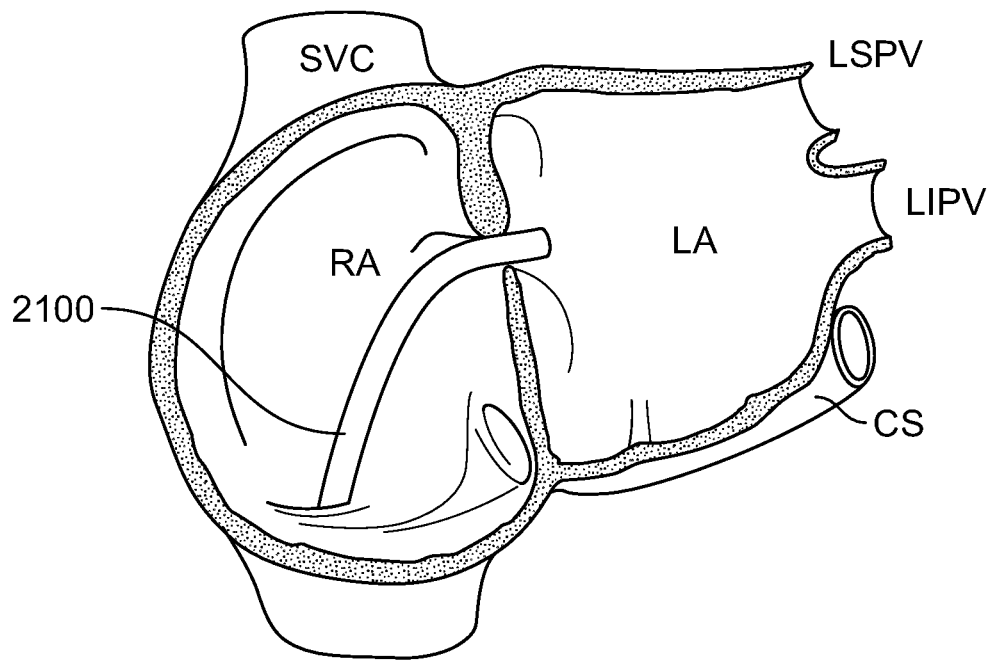
FIGS. 26-27 are illustrations of a procedure to place a distal section of a cryoablation catheter against the endocardial wall in the left atrium, circumscribing the left superior and inferior pulmonary vein entries, according to an embodiment of the invention.

With reference first to FIG. 26, a cross sectional view of the heart includes the right atrium RA 2, left atrium LA 3, left superior pulmonary vein LSPV entry, and left inferior pulmonary vein LIPV entry. Guide catheter 2100 is shown extending through the septum and into the left atrium.

Though not shown, mapping catheters may be positioned in the entry to the LSPV of the left atrium for monitoring electrical signals of the heart. The mapping catheters may be placed in other locations, such as, for example the coronary sinus (CS). Examples of mapping catheters include the WEBSTER® CS Bi-Directional Catheter and the LASSO® Catheter, both of which are manufactured by Biosense Webster Inc. (Diamond Bar, Calif. 91765, USA). Another example of mapping and cryo-treatment system is described in US Patent Publication No. 2015/0018809 to Mihalik.

Optionally, an esophageal warming balloon may be placed in the esophagus to mitigate collateral damage arising from creating the lesions. An esophageal warming balloon prevents the cold temperatures from reaching the inner layer of cells of the esophagus, and can prevent formation of, e.g., an atrio-esophageal fistula. An example of a suitable esophageal warming balloon apparatus that may be used is described in commonly assigned U.S. patent application Ser. No. 15/028,927, entitled "ENDOESOPHAGEAL BALLOON CATHETER, SYSTEM, AND RELATED METHOD," filed Oct. 12, 2014 by Alexei Babkin, et al., the contents of which is incorporated herein by reference in its entirety for all purposes.

Figure 27:
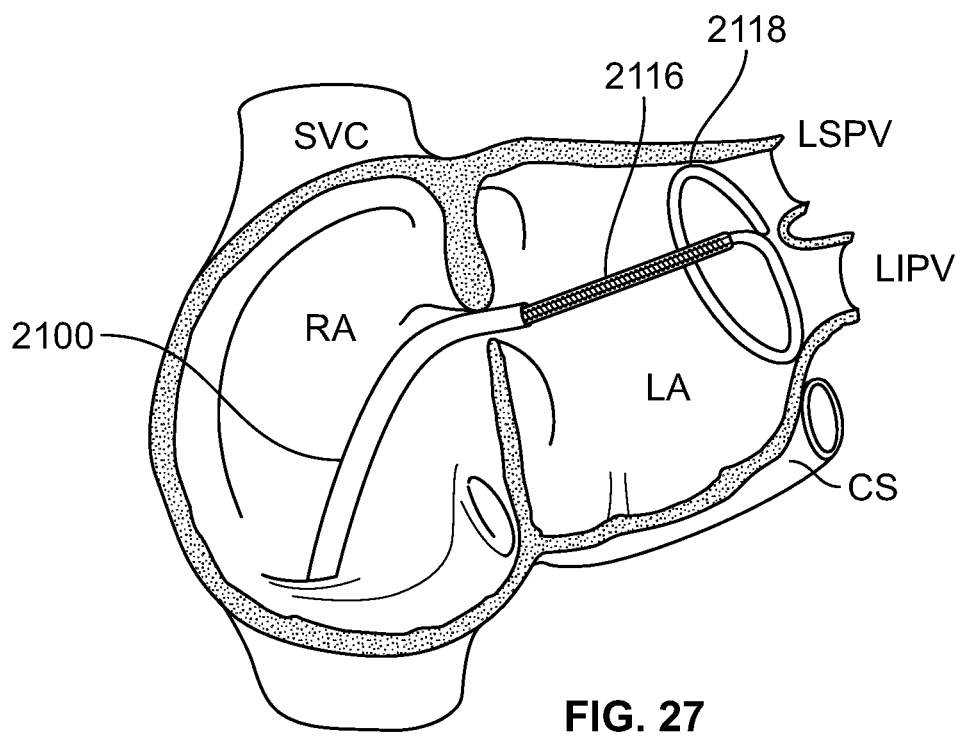

FIG. 27 illustrates a distal section of the cryoablation catheter 2116 advanced through the guide sheath 2100. The energy element 2118 is shown having a circular shape formed as disclosed and described herein and urged against the endocardium. As described herein the shape may be adjusted to make continuous contact with the tissue, and to form an elliptical or circular-shaped continuous lesion (such as lesion 8 shown in FIG. 24) which encloses all the left PV entries.

In embodiments the shape is modified by reducing the diameter of loop, articulating the intermediate section of the shaft, and rotating or steering the catheter distal section. Collectively, the steps of deployment, diameter control, steering and articulation can place the entire circumference of the loop in continuous contact with the endocardium tissue. When energy is applied to the distal treatment section such as, for example, by flowing a cryogen through the distal treatment section, a continuous elongate ring-shaped lesion (frozen tissue) is formed such as the lesion 8 shown in FIG. 24, enclosing all left pulmonary vein entries.

Figure 28:
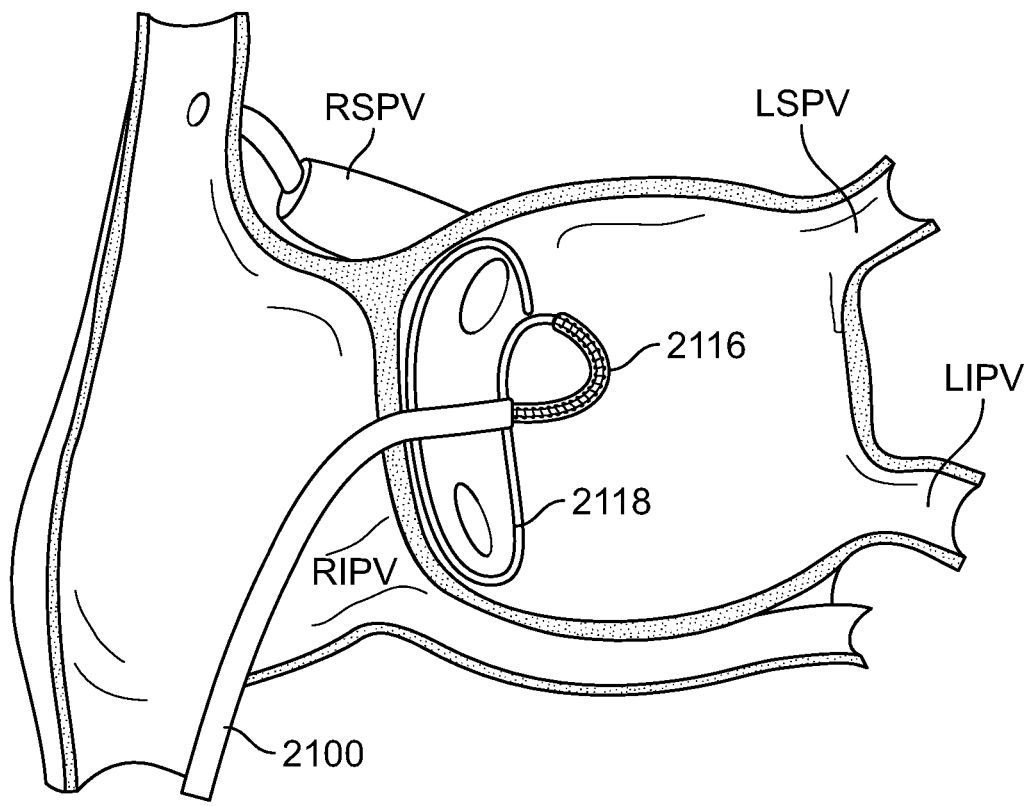
FIGS. 28-29 are illustrations of a procedure to place a distal section of a cryoablation catheter against the endocardial wall in the left atrium, circumscribing the right superior and inferior pulmonary vein entries, according to an embodiment of the invention.

FIG. 28 illustrates formation of a ring-shaped lesion around the right superior pulmonary vein (RSPV) entries and the right inferior pulmonary vein (RIPV) entries such as, for example, lesion 9 shown in FIG. 24. In contrast to the somewhat linear (straight shot) positioning shown in FIGS. 26-27, the catheter neck region 2116 shown in FIG. 28 is deflected nearly 180 degrees to aim towards the right pulmonary veins. Energy element portion 2118 is positioned around the RSPV and RIPV entries.

FIG. 28 shows the energy element 2118 deployed in a circular shape and contacting the endocardium. As described herein the shape may be adjusted to make better contact with the tissue in order to form an elongate ring-shaped, continuous lesion that engulfs or surrounds the RSPV and RIPV entries.

A similar elongate ring-shaped, continuous lesion can be formed to surround the left superior pulmonary vein (LSPV) entries and the left inferior pulmonary vein (LIPV) entries.

Figure 29:
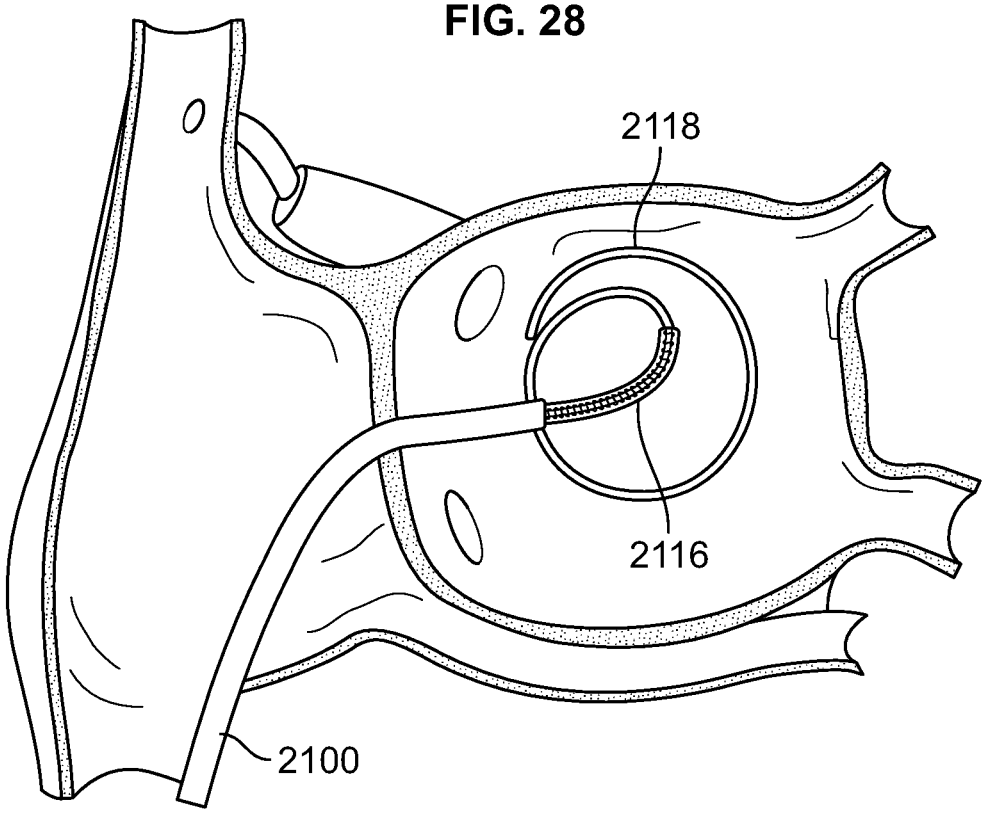

FIG. 29 shows the catheter 2116 deflected to aim towards the posterior wall of the left atrium. Energy element portion 2118 is manipulated to form a loop and urged against the posterior wall, overlapping with previously-formed right and left lesions.

Optionally, and not shown, guidewires can be advanced from the guide sheath and used to navigate the catheter treatment section into position.

The shape of the lesion and pattern may vary. In embodiments, and with reference to FIG. 30, a "box-shaped" lesion 900 is shown surrounding multiple pulmonary vein entries in a PVI procedure. The box-shaped lesion surrounds the pulmonary vein entries on both the left and right sides of the left atrium.

Figure 30:
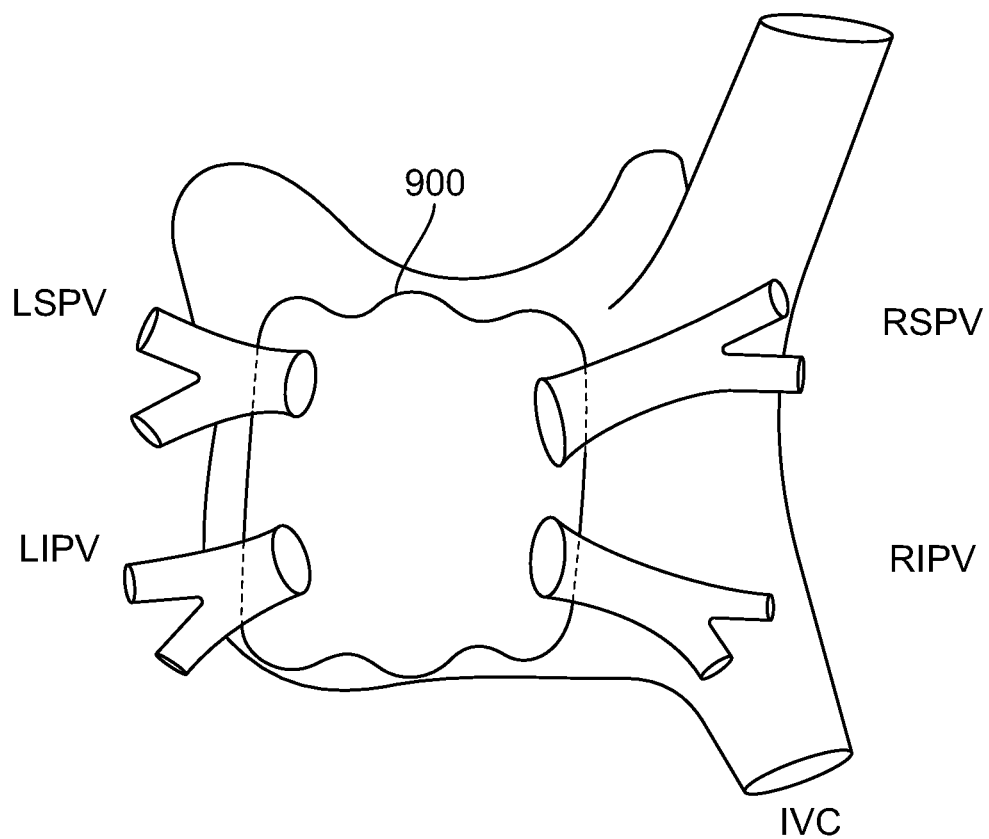
FIGS. 30-31 illustrate a method for creating a box-shaped lesion, according to an embodiment of the invention, where the figures depict the left atrium as viewed from the back of a patient.

The box-shaped lesion 900 may be formed in various ways. In some embodiments, the box-shaped lesion is formed by overlapping a combination of lesions, which can have similar or different shapes (e.g., oval, ellipse, ring, etc.) to form an overall larger continuous lesion, which may have a box-like shape 900 as shown in FIG. 30.

Figure 31:
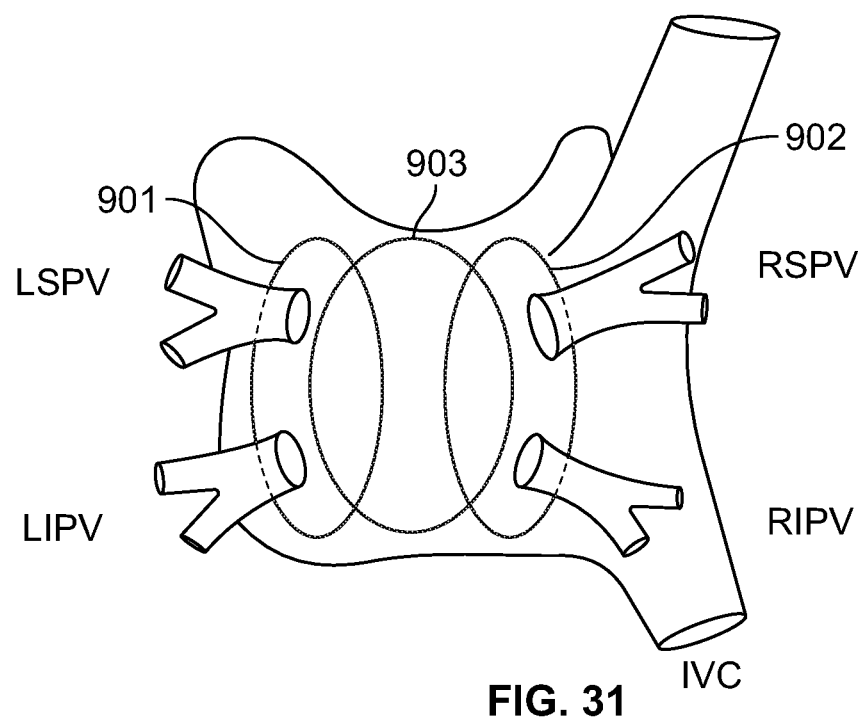
Figure 32:
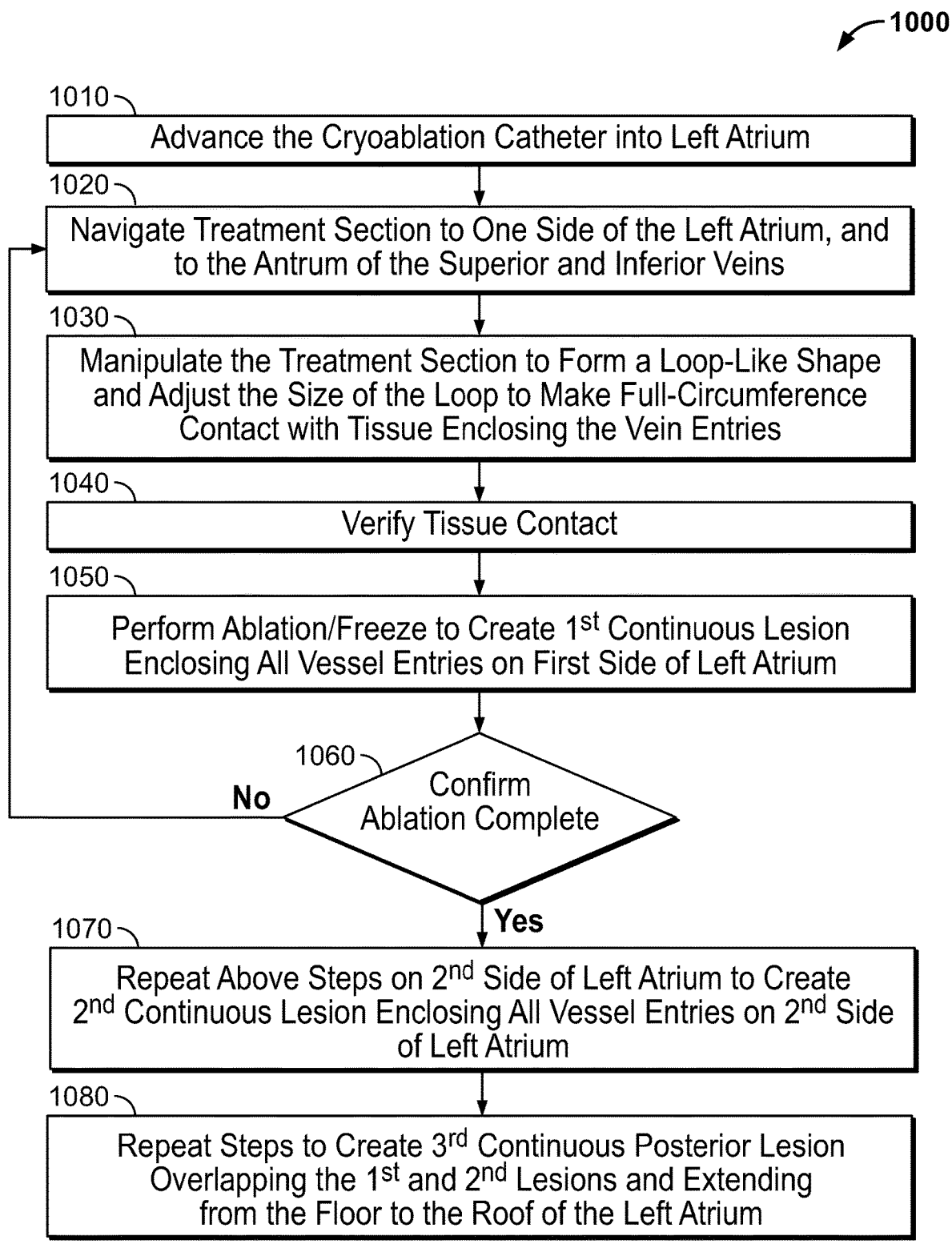
FIG. 32 is flow diagram showing a method of creating a box-shaped lesion to enclose multiple PVs in the left atrium, according to an embodiment of the invention.

With reference to the illustration shown in FIG. 31, and the corresponding flow diagram shown in FIG. 32, a method 1000 for forming a box-shaped lesion in the left atrium that encircles/encloses all pulmonary vein (RSPV, RIPV, LSPV and LIPV) entries, is described.

Step 1010 states to advance the cryoablation catheter into the left atrium, which can be performed using a guide sheath, for example.

Step 1020 states to navigate the treatment section (energy element portion 2118) of the catheter to one side of the left atrium and into the antrum of the superior and inferior pulmonary veins on that side of the atrium.

Step 1030 states to manipulate the treatment section (energy element portion 2118) of the catheter to form a loop-like shape and to adjust the size of the loop to make full circumference tissue contact with tissue to enclose the superior and inferior vein entries on that side of the atrium.

Step 1040 states to verify tissue contact. This step may be performed using, for example, electrodes mounted on the distal treatment section as disclosed and escribed in commonly assigned International Patent Application No. PCT/US16/51954, entitled "TISSUE CONTACT VERIFICATION SYSTEM", filed Sep. 15, 2016 by Alexei Babkin, et al., the entire contents of which are incorporated herein by reference for all purposes. The tissue electrocardiograms (ECGs) may be displayed using an EP recording system.

Optionally, an esophageal balloon (EBB) (as discussed above) is advanced into the esophagus in the vicinity of the heart. The EBB is inflated and a thermally conducting liquid is circulated through the balloon for the duration of the ablation treatment. As described herein, the EEB minimizes collateral damage to tissue adjacent the ablation zone by warming the tissue during the ablation cycle.

Step 1050 states to perform the ablation by freezing the tissue to create a first continuous lesion enclosing/surrounding the pulmonary vein entries on the first side of the left atrium, for example, the left side lesion 901 in FIG. 31. The duration of the tissue freeze may be up to 3 minutes or more, and generally ranges from about 1 to 3 minutes, and preferable is about 2 minutes. In embodiments, the freeze step comprises a single application of uninterrupted ablation energy.

In some embodiments, the duration of the energy application ranges from approximately 10 to 60 seconds, and sometimes is less than or equal to approximately 30 seconds.

The duration of the freeze cycle may vary. A physician or electro physiologist can elect to terminate the freeze cycle as desired (e.g., before or after the anticipated time period has passed). Examples of reasons for early termination include:

a desire to reposition the catheter, a desire to improve catheter-tissue contact, or a safety concern.

Step 1060 states to confirm ablation is complete. Electrical activity from the electrodes on the distal treatment section may be monitored. During freezing, the electrocardiograms (ECG) will present abnormal signals due to freezing of the tissue and blood in contact with the freezing tip. After freezing is completed, however, the ECGs should not show any signal or evidence of a voltage potential in the tissue due to tissue necrosis.

If, however, the ECG signals/signatures reappear after the freezing step indicating that there is still electrical activity in the tissue, this is evidence that the ablation was not complete and that PVI may not have been achieved. In the event PVI was not achieved, the above described applicable steps can be repeated.

In some embodiments, another freeze in the same location can be commenced. Or, the catheter may be repositioned or otherwise adjusted to make better contact with the target tissue. Then, an additional freeze may be performed.

Performing an additional freeze can be beneficial especially if the distance between the pulmonary veins is unusually large. When the distance between the pulmonary veins is unusually large, isolating the pulmonary vein entries with only one continuous lesion is a challenge. In a sub population of patients with unusually enlarged hearts, forming an additional lesion around the pulmonary vein entries increases the likelihood of a complete and durable PVI.

Additionally, in some situations, it may be desirable to narrow the ablation loop to accommodate a single vein. In embodiments, the method comprises performing a single vein isolation around the ostium of the single vein. The diameter of the catheter loop is reduced from the relatively large size for isolating multiple veins to the applicable size of the single vein. In embodiments, the single vein isolation is performed subsequent to the larger multiple vein isolations.

Step 1070 states to repeat the applicable steps for the pulmonary veins on the other side of the left atrium. That is, for example, after the left vein antrum is isolated, the catheter loop will be navigated to the right vein antrum and all relevant steps should be repeated to create a second, right side lesion (e.g., lesion 902 of FIG. 31).

Step 1080 states to repeat the applicable above described steps for the posterior wall lesion (lesion 903 in FIG. 31). Once both the LSPV and LIPV antrum and the RSPV and RIPV vein antrum are isolated, the looped treatment section of the catheter is navigated to the posterior wall of the left atrium.

Optionally, the EBB is inflated in the esophagus and activated prior to ablation of the posterior wall. The other applicable steps for placing the left and right lesions are repeated for the posterior lesion. The posterior lesion 903 is more centrally located, and shown in FIG. 31 overlapping the left and right antrum lesions (901 and 902, respectively). Lesion 903 is also shown extending from the floor to the ceiling of the left atrium.

Although the method describes a particular order to create the left pulmonary vein, right pulmonary vein and posterior wall lesions, embodiments of the invention are not intended to be so limited except where specifically recited in the appended claims. The order that the lesions are created may vary. For example, in embodiments, the right side or posterior lesion may be performed prior to the left side lesion.

As can be seen in FIGS. 30 and 31, collectively, the plurality of independent lesions (901, 902, 903) form a composite box-like shaped continuous lesion 900 (FIG. 30) that encloses all the pulmonary vein entries on all sides (left, right, top and bottom) of the left atrium. In embodiments, the sum of the sub-lesions form an enclosure in the shape of a box, square, or rectangle. Performing the ablations to form this composite, continuous lesion 900 effectively electrically isolates all the pulmonary vein entries in the left atrium.

Figure 33:
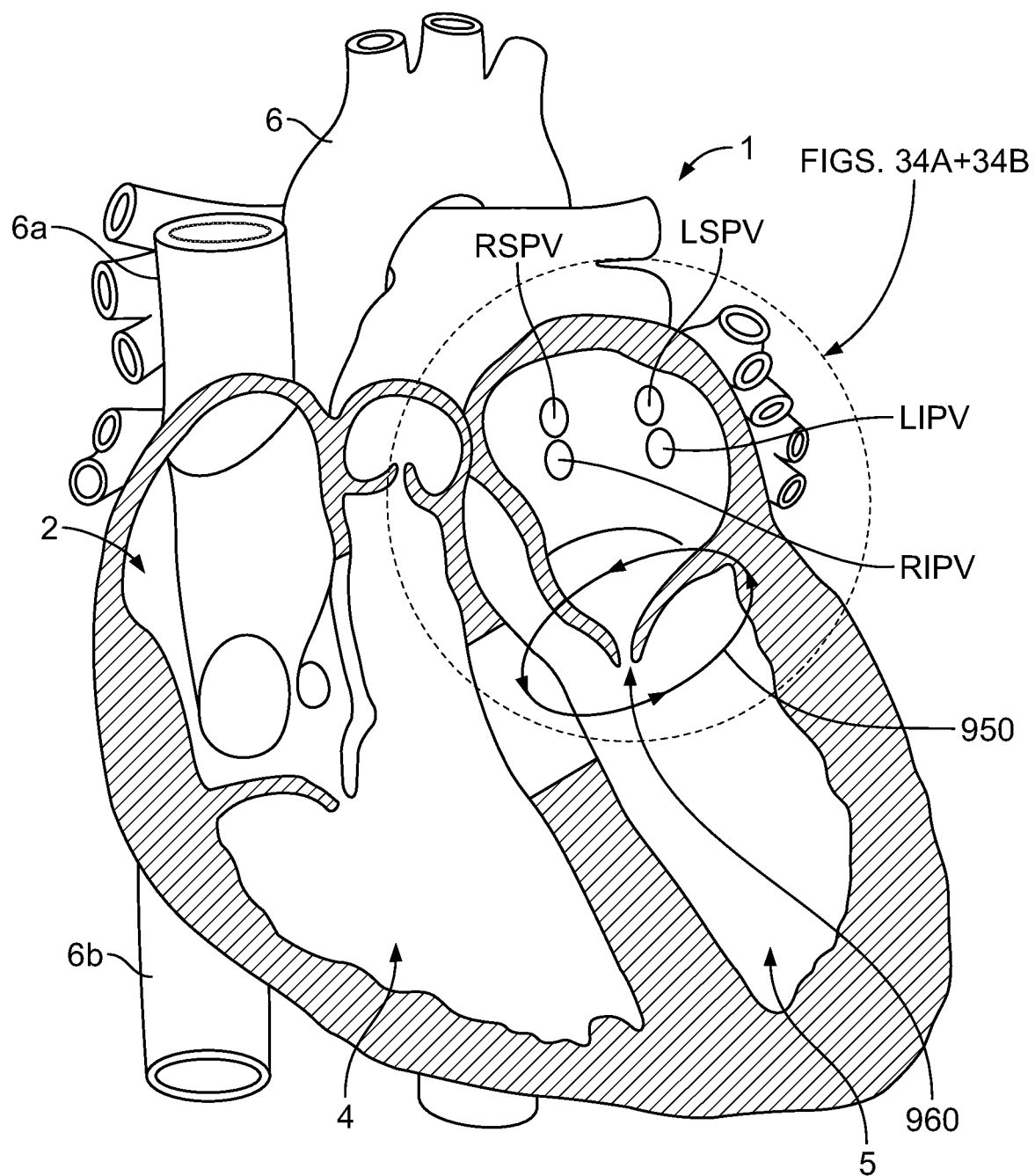
FIG. 33 is an illustration of a heart showing mitral valve electrical activity.
Figure 34A:
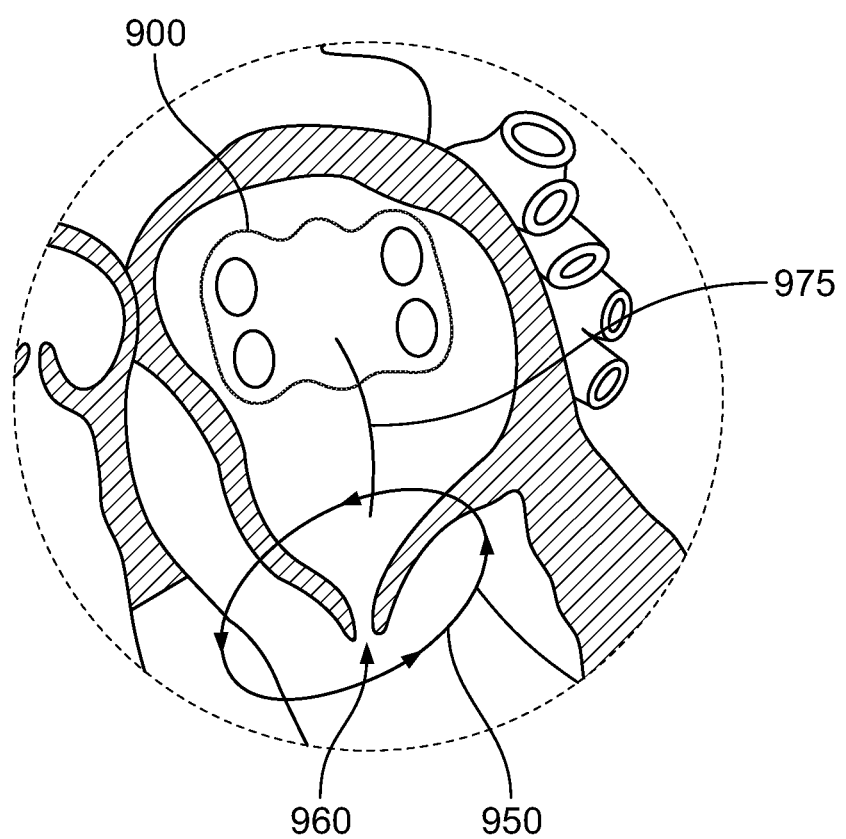
FIG. 34A depicts formation of a lesion to interrupt mitral valve electrical activity, according to an embodiment of the invention.
Figure 34B:
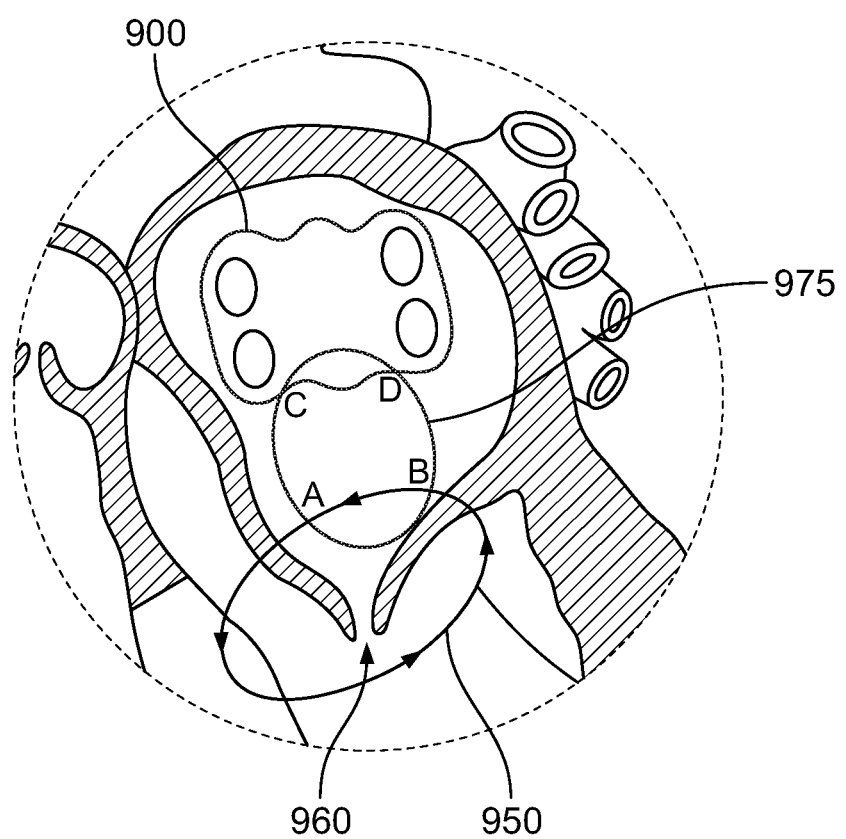
FIG. 34B depicts formation of a lesion to interrupt mitral valve electrical activity, according to an embodiment of the invention.

In patients that have atrial flutter in addition to paroxysmal atrial fibrillation and in patients that have non-paroxysmal atrial fibrillation, in addition to forming the lesions (901, 902, 903) discussed above with reference to FIGS. 30-32, it will be necessary to form an additional lesion to isolate the mitral valve. In these patients, as depicted in FIG. 33, there is electrical activity/current 950 that flows around the mitral valve 960. Therefore, the flow of this electrical activity/current 950, must be interrupted and stopped/prevented in order to treat these patients. Depicted in FIGS. 34A and 34B are embodiments of lesions that can be formed to interrupt the flow of current 950. As can be seen in the figures, this mitral lesion 975 connects to the box-like lesion 900 formed by the left pulmonary vein lesion 901, the right pulmonary vein lesion 902 and the posterior wall lesion 903.

As depicted in FIG. 34A, in one embodiment, the mitral lesion 975 extends from the vicinity of the mitral valve 960 (the mitral valve annulus) and intersects with the flow path of the current 950 and lesion 900. In this and other embodiments, it important that the mitral lesion 975 at least intersects with the flow path of the current 950 and lesion 900. Therefore, the mitral lesion 975 can be formed at various locations within the left atrium as long as it intersects the flow path of the current 950 and connects to lesion 900. This type of lesion can be formed by modifying the shape of the treatment section of the catheter.

In the embodiment depicted in FIG. 34B, the same loop-like treatment section of the catheter used to create the left pulmonary vein lesion 901, the right pulmonary vein lesion 902 and the posterior wall lesion 903 can be used to create the mitral lesion 975. As can be seen in FIG. 34B, creating a loop-like or circular mitral lesion 975 cause the lesion 975 to intersect the flow path of the current 950 and lesion 900 at multiple points (A, B, C, D) thereby increasing the likelihood of a successful procedure.

Figure 35:
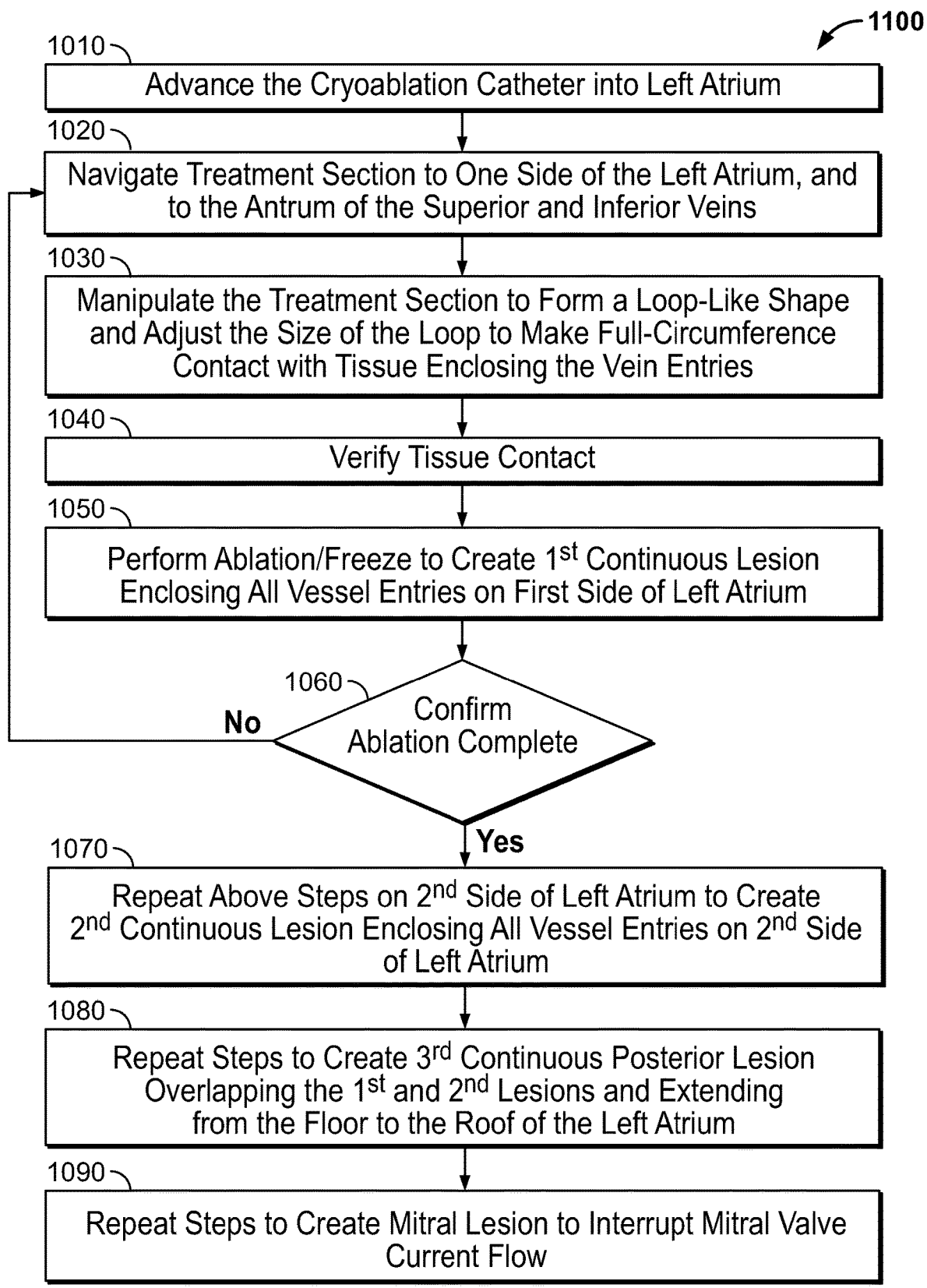
FIG. 35 is flow diagram showing a method of creating a box-shaped lesion to enclose multiple PVs in the left atrium and a lesion to interrupt mitral valve electrical activity, according to an embodiment of the invention.

If necessary, the mitral lesion 975 can be created after the box-like lesion 900 described above with respect to FIG. 32 is formed. A method 1100 for performing a procedure that includes forming the mitral lesion 975 as step 1090 after the box-like lesion 900 is formed is set forth in the flow diagram shown in FIG. 35. It will be readily apparent to those skilled in the art that the steps used in the procedure for forming the left pulmonary vein lesion 901, the right pulmonary vein lesion 902, the posterior wall lesion 903 and the mitral lesion 975 can be performed in any order as long as following the procedure, all the pulmonary vein entries are isolated and the flow path of current 950 is interrupted.

Figure 36:
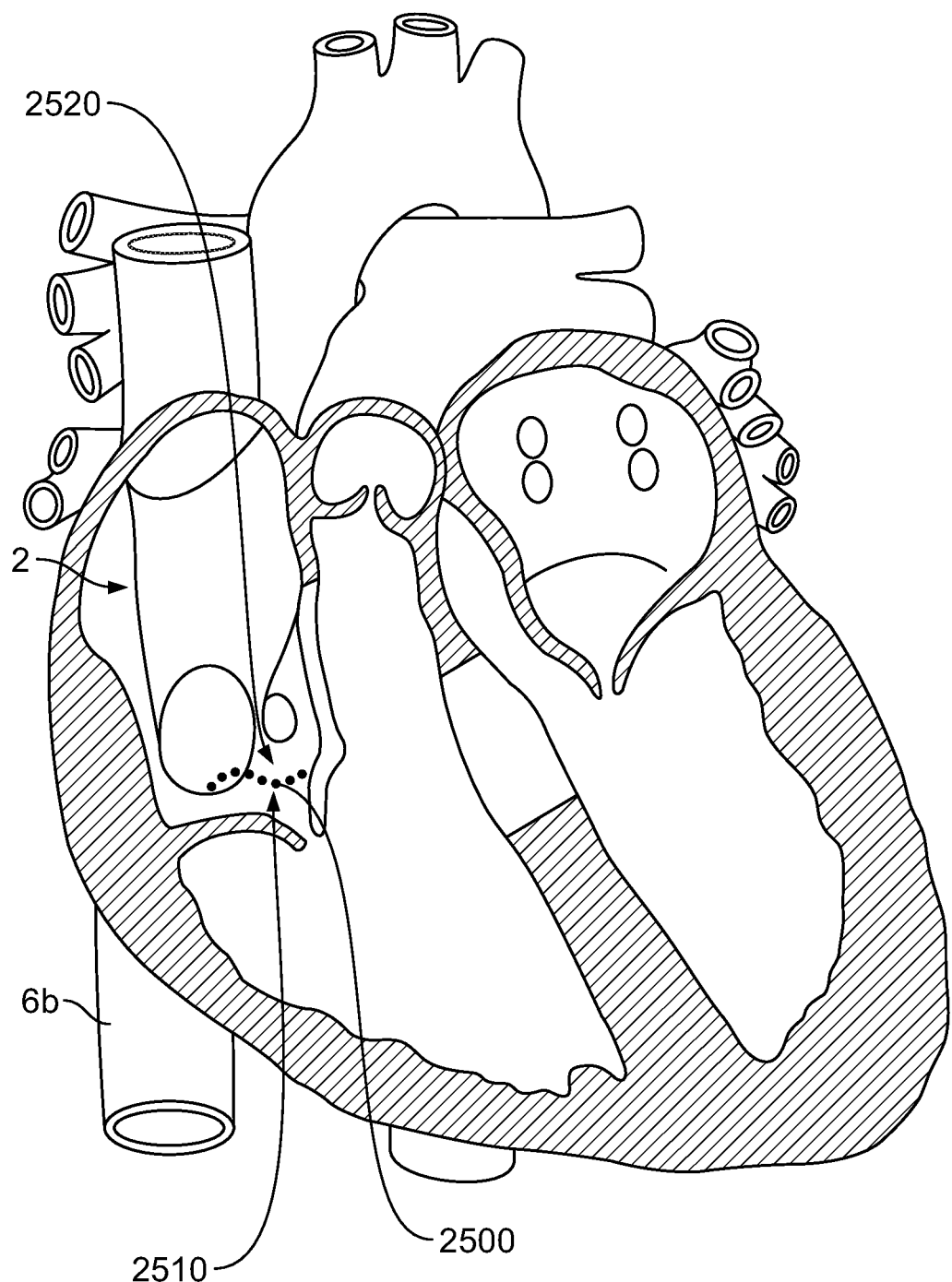
FIG. 36 depicts formation of a lesion to interrupt electrical activity in the right atrium, according to an embodiment of the invention.

In another embodiment, in some patients that suffer from persistent atrial fibrillation, a linear lesion in the right atrium 2 may be necessary. As depicted in FIG. 36, this linear lesion 2500 is created to connect the entrance of the Inferior Vena Cava (IVC) 6b and the annulus of the Tricuspid Valve (TV) 2510 and extends through the Cava Tricuspid Isthmus (CTI) 2520. This CTI lesion is used to prevent/interrupt the majority of potential re-entry circuits in the right atrium such as, for example, right atrial flutter and/or other arrhythmias that originate in the right atrium. This type of lesion is described in commonly assigned U.S. patent application Ser. No. 15/304,524, entitled "ENDOVASCULAR NEAR CRITICAL FLUID BASED CRYOABLATION CATHETER HAVING PLURALITY OF PREFORMED TREAT- MENT SHAPES," filed Oct. 15, 2016 by Alexei Babkin, et al., the contents of which is incorporated herein by reference in its entirety for all purposes.

In some embodiments, for certain patients, in addition to forming the lesions (901, 902, 903) discussed above with reference to FIGS. 30-32, it will be necessary to form the CTI lesion 2500 discussed above with reference to FIG. 36. It will be readily apparent to those skilled in the art that the steps used in the procedure for forming the left pulmonary vein lesion 901, the right pulmonary vein lesion 902, the posterior wall lesion 903 and the CTI lesion 2500 can be performed in any order as long as following the procedure, all the pulmonary vein entries are isolated and the majority of the potential re-entry circuits in the right atrium are interrupted/prevented.

In some embodiments, for certain patients, in addition to forming the lesions (901, 902, 903) discussed above with reference to FIGS. 30-32 and the mitral lesion 975 discussed above with reference to FIGS. 34A, 34B and 35, it will be necessary to form the CTI lesion 2500 discussed above with reference to FIG. 36. It will be readily apparent to those skilled in the art that the steps used in the procedure for forming the left pulmonary vein lesion 901, the right pulmonary vein lesion 902, the posterior wall lesion 903, the mitral lesion 975 and the CTI lesion 2500 can be performed in any order as long as following the procedure, all the pulmonary vein entries are isolated, the flow path of current 950 is interrupted and the majority of the potential re-entry circuits in the right atrium are interrupted/prevented.

Many modifications and variations of the present invention are possible in light of the above teachings. It is therefore to be understood that within the scope of the appended claims the invention may be practiced otherwise than as specifically described.

The invention claimed is:

1. A method of creating a lesion in cardiac tissue, the method comprising:
    deploying a distal treatment section of an ablation catheter into a heart chamber having a first side and a second side opposite the first side;
    manipulating the distal treatment section against cardiac tissue and into a curved shape that simultaneously encloses a plurality of vessel entries on the first side of the heart chamber and excludes vessel entries on the second side of the heart chamber, and wherein the plurality of vessel entries on the first side of the heart chamber comprise a superior vessel entry and an inferior vessel entry;
    commencing a first application of ablation energy from the distal treatment section to the cardiac tissue;
    halting the first application of ablation energy to the cardiac tissue, wherein the first application of ablation energy causes formation of a first continuous lesion in the cardiac tissue that encloses the plurality of vessel entries, wherein the first continuous lesion enclosing the plurality of vessel entries encloses a superior and an inferior pulmonary vein entry on a first side of a left atrium;
    manipulating the distal treatment section to a second side of the left atrium and into contact with cardiac tissue;
    applying a second application of ablation energy from the distal treatment section such that a second continuous lesion is formed enclosing the superior and inferior pulmonary vein entries on the second side of the left atrium.

2. The method of claim 1, further comprising manipulating the distal treatment section into contact with a posterior wall of the left atrium, and applying a third application of ablation energy from the distal treatment section such that a third continuous lesion is formed, the third continuous lesion overlapping with the first continuous lesion and the second continuous lesion, and extending from a roof to a floor of the posterior wall.

3. The method of claim 2, wherein the first, second, and third continuous lesions collectively form a box-like shaped lesion surrounding the superior and inferior left and right pulmonary vein entries of the left atrium.

4. The method of claim 1, further comprising detecting the position of the distal treatment section of the ablation catheter in the heart chamber, wherein the detecting is performed using electrodes present on the distal treatment section of the ablation catheter.

5. The method of claim 1, wherein the distal treatment section is deformable to a circular shape, causing the shape of lesions to be a closed circular shape.

6. The method of claim 1, wherein the first application of energy is application of cryoenergy.

7. The method of claim 6, wherein the application of cryoenergy comprises circulating a near critical fluid through at least one fluid delivery tube and at least one fluid return tube extending through the distal treatment section of the ablation catheter.

8. A method of performing an ablation procedure in a heart cavity, the method comprising the steps of:
    advancing an ablation catheter into the heart cavity;
    navigating a treatment section of the ablation catheter to a first area of interest in the heart cavity;
    manipulating the treatment section to form a loop-like shape to encircle cardiac tissue in the first area of interest in the heart cavity and to contact the cardiac tissue in the first area of interest in the heart cavity, wherein the first area of interest comprises an inferior and superior vessel entries and the loop-like shape encircles both vessel entries at the same time;
    performing at least one ablation cycle from the treatment section to create a first continuous lesion that encircles the cardiac tissue in the first area of interest in the heart cavity;
    navigating the treatment section of the ablation catheter to a second area of interest in the heart cavity;
    manipulating the treatment section to encircle and contact cardiac tissue in the second area of interest in the heart cavity; and
    performing at least one ablation cycle from the treatment section to create a second continuous lesion that encircles the cardiac tissue in the second area of interest in the heart cavity.

9. The method of claim 8, further comprising the steps of:
    navigating the treatment section of the ablation catheter to a third area of interest in the heart cavity;
    manipulating the treatment section to encircle and contact cardiac tissue in the third area of interest in the heart cavity; and
    performing at least one ablation cycle from the treatment section to create a third continuous lesion that encircles the cardiac tissue in the third area of interest in the heart cavity.

10. The method of claim 9, further comprising the steps of:
    navigating the treatment section of the ablation catheter to a fourth area of interest in the heart cavity;
    manipulating the treatment section to encircle and contact cardiac tissue in the fourth area of interest in the heart cavity; and performing at least one ablation cycle from the treatment section to create a fourth continuous lesion that encircles the cardiac tissue in the fourth area of interest in the heart cavity.

11. The method of claim 8, further comprising the step of verifying cardiac tissue contact prior to performing at least one ablation cycle from the treatment section.

12. The method of claim 8, further comprising the step of confirming that the at least one ablation cycle created the first continuous lesion.

13. The method of claim 12, further comprising the step of performing at least one ablation cycle from the treatment section.

14. The method of claim 8, wherein the at least one ablation cycle comprises application of cryoenergy.

15. The method of claim 14, wherein the application of cryoenergy comprises circulating a near critical fluid through at least one fluid delivery tube and at least one fluid return tube extending through the treatment section of the ablation catheter.

16. A method of performing an ablation procedure in a heart, the method comprising the steps of:
advancing an ablation catheter into a left atrium;
navigating a treatment section of the ablation catheter to a first side of the left atrium to an antrum of a first side of superior pulmonary vein entry and a first side of inferior pulmonary vein entry;
manipulating the treatment section to form a loop-like shape to simultaneously encircle the first side superior pulmonary vein entry and the first side inferior pulmonary vein entry and to contact cardiac tissue surrounding the first side superior pulmonary vein entry and the first side inferior pulmonary vein entry;
performing at least one ablation cycle from the treatment section to create a first continuous lesion that encircles the first side superior pulmonary vein entry and the first side inferior pulmonary vein entry;
navigating the treatment section of the ablation catheter to a second side of the left atrium to an antrum of a second side of superior pulmonary vein entry and a second side of inferior pulmonary vein entry;
manipulating the treatment section to encircle the second side superior pulmonary vein entry and the second side inferior pulmonary vein entry and to contact cardiac tissue surrounding the second side superior pulmonary vein entry and the second side inferior pulmonary vein entry;
performing at least one ablation cycle from the treatment section to create a second continuous lesion that encircles the second side superior pulmonary vein entry and the second side inferior pulmonary vein entry;
navigating the treatment section of the ablation catheter to a posterior wall of the left atrium;
manipulating the treatment section to form a loop that overlaps the first continuous lesion and the second continuous lesion and that contacts cardiac tissue at the posterior wall; and
performing at least one ablation cycle from the treatment section to create a third continuous lesion that overlaps the first continuous lesion and the second continuous lesion, wherein the first continuous lesion, the second continuous lesion and the third continuous lesion form a composite continuous lesion that encircles the first side superior pulmonary vein entry, the first side inferior pulmonary vein entry, the second side superior pulmonary vein entry and the second side inferior pulmonary vein entry.

17. The method of claim 16, further comprising the step of creating a lesion from the treatment section that extends from an area adjacent to a mitral valve annulus and intersects at least a portion of the composite continuous lesion.

18. The method of claim 16, further comprising the step of creating a lesion from the treatment section that extends from an area adjacent to a mitral valve annulus and intersects at least a portion of the first continuous lesion or the second continuous lesion or the third continuous lesion.

19. The method of claim 16, further comprising the steps of:
navigating the treatment section of the ablation catheter to a right atrium; and
creating a lesion from the treatment section that connects an entrance of an Inferior Vena Cava and an annulus of the Tricuspid Valve and extends through a Cava Tricuspid Isthmus.

20. The method of claim 16, further comprising the steps of:
creating a lesion from the treatment section that extends from an area adjacent to a mitral valve annulus and intersects at least a portion of the composite continuous lesion;
navigating the treatment section of the ablation catheter to a right atrium; and
creating a lesion from the treatment section that connects an entrance of an Inferior Vena Cava and an annulus of the Tricuspid Valve and extends through a Cava Tricuspid Isthmus.

21. The method of claim 16, wherein the at least one ablation cycle comprises application of cryoenergy.

22. The method of claim 21, wherein the application of cryoenergy comprises circulating a near critical fluid through at least one fluid delivery tube and at least one fluid return tube extending through the treatment section of the ablation catheter.

* * * * *